(12) United States Patent
Connor

(10) Patent No.: US 10,028,747 B2
(45) Date of Patent: Jul. 24, 2018

(54) COILS WITH A SERIES OF PROXIMALLY-AND-DISTALLY-CONNECTED LOOPS FOR OCCLUDING A CEREBRAL ANEURYSM

(71) Applicant: Robert A. Connor, Forest Lake, MN (US)

(72) Inventor: Robert A. Connor, Forest Lake, MN (US)

(73) Assignee: Aneuclose LLC, St. Paul, MN (US)

( * ) Notice: Subject to any disclaimer, the term of this patent is extended or adjusted under 35 U.S.C. 154(b) by 118 days.

(21) Appl. No.: 15/080,915

(22) Filed: Mar. 25, 2016

(65) Prior Publication Data

US 2016/0206320 A1      Jul. 21, 2016

Related U.S. Application Data

(63) Continuation-in-part of application No. 14/526,600, filed on Oct. 29, 2014, which is a continuation-in-part
(Continued)

(51) Int. Cl.
*A61M 29/00* (2006.01)
*A61B 17/12* (2006.01)

(52) U.S. Cl.
CPC .... *A61B 17/12113* (2013.01); *A61B 17/1215* (2013.01); *A61B 17/12168* (2013.01);
(Continued)

(58) Field of Classification Search
CPC ........ A61B 17/12022; A61B 17/12027; A61B 17/12031; A61B 17/12036; A61B 17/1204; A61B 17/12109; A61B 17/12113; A61B 17/12118; A61B 17/1214; A61B 17/12145; A61B 17/1215; A61B 17/12168; A61B 17/12172; A61B 17/12177; A61B 17/12154; A61B 17/12163; A61B 2017/1205; A61B 2017/12054; A61B 2017/12059; A61B 2017/12063; A61B 2017/12068; A61F 6/18; A61F 6/20; A61F 6/22; A61F 6/225; A61F 6/146; A61F 6/148
See application file for complete search history.

(56) References Cited

U.S. PATENT DOCUMENTS 4,364,392 A   12/1982   Strother et al.
4,994,069 A    2/1991   Ritchart et al.
(Continued)

FOREIGN PATENT DOCUMENTS

WO PCT/US/2009/002537      4/2009

OTHER PUBLICATIONS

U.S. Appl. No. 12/387,637, filed 2009, Connor et al.
U.S. Appl. No. 13/889,451, filed 2013, Connor et al.

*Primary Examiner* — Katrina Stransky
*Assistant Examiner* — Kankindi Rwego

(57) ABSTRACT

This invention can be embodied in a device for occluding a cerebral aneurysm comprising a series of proximally-and-distally-connected coil loops. This invention can further comprise a stretchable mesh which spans the interiors of these loops. These loops (and the stretchable mesh) overlap to create a coil-and-mesh mass within the aneurysm sac which occludes the aneurysm.

7 Claims, 2 Drawing Sheets

Related U.S. Application Data of application No. 12/989,048, filed on Oct. 21, 2010, now Pat. No. 8,974,487.

(60) Provisional application No. 61/126,047, filed on May 1, 2008, provisional application No. 61/126,027, filed on May 1, 2008, provisional application No. 61/897,245, filed on Oct. 30, 2013.

(52) U.S. Cl.
CPC . *A61B 17/12163* (2013.01); *A61B 2017/1205* (2013.01); *A61B 2017/12077* (2013.01)

(56) References Cited

U.S. PATENT DOCUMENTS

| | | |
|---|---|---|
| 5,226,889 A | 7/1993 | Sheiban |
| 5,304,132 A | 4/1994 | Jang |
| 5,334,210 A | 8/1994 | Gianturco |
| 5,350,397 A | 9/1994 | Palermo et al. |
| 5,370,691 A | 12/1994 | Samson |
| 5,382,259 A | 1/1995 | Phelps et al. |
| 5,405,379 A | 4/1995 | Lane |
| 5,411,549 A | 5/1995 | Peters |
| 5,423,829 A | 6/1995 | Pham et al. |
| 5,443,478 A | 8/1995 | Purdy |
| 5,522,822 A | 6/1996 | Phelps et al. |
| 5,536,252 A | 7/1996 | Imran et al. |
| 5,582,619 A | 12/1996 | Ken |
| 5,603,722 A | 2/1997 | Phan et al. |
| 5,624,449 A | 4/1997 | Pham et al. |
| 5,624,461 A | 4/1997 | Mariant |
| 5,624,685 A | 4/1997 | Takahashi et al. |
| 5,639,277 A | 6/1997 | Mariant et al. |
| 5,645,559 A | 7/1997 | Hachtman et al. |
| 5,649,949 A | 7/1997 | Wallace et al. |
| 5,690,666 A | 11/1997 | Berenstein et al. |
| 5,690,667 A | 11/1997 | Gia |
| 5,693,088 A | 12/1997 | Lazarus |
| 5,702,361 A | 12/1997 | Evans et al. |
| 5,718,711 A | 2/1998 | Berenstein et al. |
| 5,723,004 A | 3/1998 | Dereume et al. |
| 5,733,294 A | 3/1998 | Forber et al. |
| 5,733,329 A | 3/1998 | Wallace et al. |
| 5,743,905 A | 4/1998 | Eder et al. |
| 5,749,891 A | 5/1998 | Ken et al. |
| 5,749,894 A | 5/1998 | Engelson |
| 5,766,160 A | 6/1998 | Samson et al. |
| 5,766,219 A | 6/1998 | Horton |
| 5,769,882 A | 6/1998 | Fogarty et al. |
| 5,769,884 A | 6/1998 | Solovay |
| 5,776,097 A | 7/1998 | Massoud |
| 5,785,679 A | 7/1998 | Abolfathi et al. |
| 5,795,331 A | 8/1998 | Cragg et al. |
| 5,800,453 A | 9/1998 | Gia |
| 5,800,455 A | 9/1998 | Palermo et al. |
| 5,826,587 A | 10/1998 | Berenstein et al. |
| 5,833,657 A | 11/1998 | Reinhardt et al. |
| 5,833,705 A | 11/1998 | Ken et al. |
| 5,836,966 A | 11/1998 | St. Germain |
| 5,853,418 A | 12/1998 | Ken et al. |
| 5,868,780 A | 2/1999 | Lashinski et al. |
| 5,873,907 A | 2/1999 | Frantzen |
| 5,888,546 A | 3/1999 | Ji et al. |
| 5,891,130 A | 4/1999 | Palermo et al. |
| 5,894,022 A | 4/1999 | Ji et al. |
| 5,911,731 A | 6/1999 | Pham et al. |
| 5,916,235 A | 6/1999 | Guglielmi |
| 5,922,019 A | 7/1999 | Hankh et al. |
| 5,925,059 A | 7/1999 | Palermo et al. |
| 5,928,260 A | 7/1999 | Chin et al. |
| 5,935,145 A | 8/1999 | Villar et al. |
| 5,935,148 A | 8/1999 | Villar et al. |
| 5,938,697 A | 8/1999 | Killion et al. |
| 5,941,249 A | 8/1999 | Maynard |
| 5,941,888 A | 8/1999 | Wallace et al. |
| 5,948,018 A | 9/1999 | Dereume et al. |
| 5,951,599 A | 9/1999 | McCrory |
| 5,957,948 A | 9/1999 | Mariant |
| 5,957,975 A | 9/1999 | Lafont et al. |
| 5,964,797 A | 10/1999 | Ho |
| 5,980,514 A | 11/1999 | Kupiecki et al. |
| 6,004,338 A | 12/1999 | Ken et al. |
| 6,007,573 A | 12/1999 | Wallace et al. |
| 6,013,084 A | 1/2000 | Ken et al. |
| 6,015,424 A | 1/2000 | Rosenbluth et al. |
| 6,015,433 A | 1/2000 | Roth |
| 6,017,977 A | 1/2000 | Evans et al. |
| 6,024,754 A | 2/2000 | Engelson |
| 6,024,765 A | 2/2000 | Wallace et al. |
| 6,027,526 A | 2/2000 | Limon et al. |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,063,111 A | 5/2000 | Hieshima et al. |
| 6,071,298 A | 6/2000 | Lashinski et al. |
| 6,074,407 A | 6/2000 | Levine et al. |
| 6,086,610 A | 7/2000 | Duerig et al. |
| 6,093,199 A | 7/2000 | Brown et al. |
| 6,096,021 A | 8/2000 | Helm et al. |
| 6,096,034 A | 8/2000 | Kupiecki et al. |
| 6,096,175 A | 8/2000 | Roth |
| 6,099,546 A | 8/2000 | Gia |
| 6,099,559 A | 8/2000 | Nolting |
| 6,123,712 A | 9/2000 | Di Caprio et al. |
| 6,123,714 A | 9/2000 | Gia et al. |
| 6,136,011 A | 10/2000 | Stambaugh |
| 6,139,564 A | 10/2000 | Teoh |
| 6,140,452 A | 10/2000 | Felt et al. |
| 6,143,007 A | 11/2000 | Mariant et al. |
| 6,149,681 A | 11/2000 | Houser et al. |
| 6,159,165 A | 12/2000 | Ferrera et al. |
| 6,159,238 A | 12/2000 | Killion et al. |
| 6,165,193 A | 12/2000 | Greene et al. |
| 6,165,212 A | 12/2000 | Dereume et al. |
| 6,168,592 B1 | 1/2001 | Kupiecki et al. |
| 6,168,615 B1 | 1/2001 | Ken et al. |
| 6,168,622 B1 | 1/2001 | Mazzocchi |
| 6,187,027 B1 | 2/2001 | Mariant et al. |
| 6,190,406 B1 | 2/2001 | Duerig et al. |
| 6,193,728 B1 | 2/2001 | Ken et al. |
| 6,210,429 B1 | 4/2001 | Vardi et al. |
| 6,221,066 B1 | 4/2001 | Ferrera et al. |
| 6,231,586 B1 | 5/2001 | Mariant |
| 6,231,597 B1 | 5/2001 | Deem et al. |
| 6,238,403 B1 | 5/2001 | Greene et al. |
| 6,254,592 B1 | 7/2001 | Samson et al. |
| 6,258,115 B1 | 7/2001 | Dubrul |
| 6,258,117 B1 | 7/2001 | Camrud et al. |
| 6,270,523 B1 | 8/2001 | Herweck et al. |
| 6,273,910 B1 | 8/2001 | Limon |
| 6,273,911 B1 | 8/2001 | Cox et al. |
| 6,280,457 B1 | 8/2001 | Wallace et al. |
| 6,281,263 B1 | 8/2001 | Evans et al. |
| 6,287,318 B1 | 9/2001 | Villar et al. |
| 6,299,619 B1 | 10/2001 | Greene et al. |
| 6,306,177 B1 | 10/2001 | Felt et al. |
| 6,309,367 B1 | 10/2001 | Boock |
| 6,309,413 B1 | 10/2001 | Dereume et al. |
| 6,312,421 B1 | 11/2001 | Boock |
| 6,312,463 B1 | 11/2001 | Rourke et al. |
| 6,331,191 B1 | 12/2001 | Chobotov |
| 6,335,384 B1 | 1/2002 | Evans et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,371,972 B1 | 4/2002 | Wallace et al. |
| 6,375,668 B1 | 4/2002 | Gifford et al. |
| 6,375,669 B1 | 4/2002 | Rosenbluth et al. |
| 6,379,373 B1 | 4/2002 | Sawhney et al. |
| 6,383,174 B1 | 5/2002 | Eder |

(56) References Cited

U.S. PATENT DOCUMENTS

| | | |
|---|---|---|
| 6,391,037 B1 | 5/2002 | Greenhalgh |
| 6,395,018 B1 | 5/2002 | Castaneda |
| 6,398,803 B1 | 6/2002 | Layne et al. |
| 6,406,490 B1 | 6/2002 | Roth |
| 6,409,721 B1 | 6/2002 | Wheelock et al. |
| 6,409,749 B1 | 6/2002 | Maynard |
| 6,416,543 B1 | 7/2002 | Hilaire et al. |
| 6,419,685 B2 | 7/2002 | Di Caprio et al. |
| 6,423,085 B1 | 7/2002 | Murayama et al. |
| 6,428,558 B1 | 8/2002 | Jones et al. |
| 6,432,128 B1 | 8/2002 | Wallace et al. |
| 6,454,738 B1 | 9/2002 | Tran et al. |
| 6,454,780 B1 | 9/2002 | Wallace |
| 6,458,119 B1 | 10/2002 | Berenstein et al. |
| 6,463,317 B1 | 10/2002 | Kucharczyk et al. |
| 6,468,302 B2 | 10/2002 | Cox et al. |
| 6,471,672 B1 | 10/2002 | Brown et al. |
| 6,475,233 B2 | 11/2002 | Trozera |
| 6,475,236 B1 | 11/2002 | Roubin et al. |
| 6,485,509 B2 | 11/2002 | Killion et al. |
| 6,485,510 B1 | 11/2002 | Camrud et al. |
| 6,497,722 B1 | 12/2002 | Von Oepen et al. |
| 6,500,190 B2 | 12/2002 | Greene et al. |
| 6,506,201 B2 | 1/2003 | Di Caprio et al. |
| 6,506,204 B2 | 1/2003 | Mazzocchi |
| 6,511,468 B1 | 1/2003 | Cragg et al. |
| 6,511,505 B2 | 1/2003 | Cox et al. |
| 6,520,985 B1 | 2/2003 | Burpee et al. |
| 6,520,987 B1 | 2/2003 | Plante |
| 6,527,919 B1 | 3/2003 | Roth |
| 6,533,801 B2 | 3/2003 | Wallace et al. |
| 6,547,804 B2 | 4/2003 | Porter et al. |
| 6,551,305 B2 | 4/2003 | Ferrera et al. |
| 6,558,414 B2 | 5/2003 | Layne |
| 6,569,190 B2 | 5/2003 | Whalen et al. |
| 6,569,193 B1 | 5/2003 | Cox et al. |
| 6,579,305 B1 | 6/2003 | Lashinski |
| 6,579,314 B1 | 6/2003 | Lombardi et al. |
| 6,585,748 B1 | 7/2003 | Jeffree |
| 6,585,753 B2 | 7/2003 | Eder et al. |
| 6,585,758 B1 | 7/2003 | Chouinard et al. |
| 6,589,230 B2 | 7/2003 | Gia et al. |
| 6,599,316 B2 | 7/2003 | Vardi et al. |
| 6,602,261 B2 | 8/2003 | Greene et al. |
| 6,602,269 B2 | 8/2003 | Wallace et al. |
| 6,602,284 B2 | 8/2003 | Cox et al. |
| 6,603,994 B2 | 8/2003 | Wallace et al. |
| 6,605,056 B2 | 8/2003 | Eidenschink et al. |
| 6,605,101 B1 | 8/2003 | Schaefer et al. |
| 6,605,111 B2 | 8/2003 | Bose et al. |
| 6,613,074 B1 | 9/2003 | Mitelberg et al. |
| 6,616,617 B1 | 9/2003 | Ferrera et al. |
| 6,623,493 B2 | 9/2003 | Wallace et al. |
| 6,629,947 B1 | 10/2003 | Sahatjian et al. |
| 6,645,237 B2 | 11/2003 | Klumb et al. |
| 6,652,576 B1 | 11/2003 | Stalker |
| 6,656,214 B1 | 12/2003 | Fogarty et al. |
| 6,660,020 B2 | 12/2003 | Wallace et al. |
| 6,660,032 B2 | 12/2003 | Klumb et al. |
| 6,669,719 B2 | 12/2003 | Wallace et al. |
| 6,669,723 B2 | 12/2003 | Killion et al. |
| 6,673,103 B1 | 1/2004 | Golds et al. |
| 6,676,701 B2 | 1/2004 | Rourke et al. |
| 6,689,148 B2 | 2/2004 | Sawhney et al. |
| 6,699,277 B1 | 3/2004 | Freidberg et al. |
| 6,719,783 B2 | 4/2004 | Lentz et al. |
| 6,723,108 B1 | 4/2004 | Jones et al. |
| 6,746,468 B1 | 6/2004 | Sepetka et al. |
| 6,746,475 B1 | 6/2004 | Rivelli |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,796,997 B1 | 9/2004 | Penn et al. |
| 6,802,851 B2 | 10/2004 | Jones et al. |
| 6,811,560 B2 | 11/2004 | Jones et al. |
| 6,814,754 B2 | 11/2004 | Greenhalgh |
| 6,818,018 B1 | 11/2004 | Sawhney |
| 6,833,003 B2 | 12/2004 | Jones et al. |
| 6,835,203 B1 | 12/2004 | Vardi et al. |
| 6,855,153 B2 | 2/2005 | Saadat |
| 6,855,154 B2 | 2/2005 | Abdel-Gawwad |
| 6,860,899 B1 | 3/2005 | Rivelli |
| 6,899,730 B1 | 5/2005 | Rivelli |
| 6,913,618 B2 | 7/2005 | Denardo et al. |
| 6,916,337 B2 | 7/2005 | Roth |
| 6,929,658 B1 | 8/2005 | Freidberg et al. |
| 6,958,061 B2 | 10/2005 | Truckai et al. |
| 6,962,602 B2 | 11/2005 | Vardi et al. |
| 6,964,657 B2 | 11/2005 | Cragg et al. |
| 6,969,401 B1 | 11/2005 | Marotta et al. |
| 6,979,344 B2 | 12/2005 | Jones et al. |
| 6,984,240 B1 | 1/2006 | Ken et al. |
| 6,994,721 B2 | 2/2006 | Israel |
| 7,001,422 B2 | 2/2006 | Escamilla et al. |
| 7,014,645 B2 | 3/2006 | Greene et al. |
| 7,029,486 B2 | 4/2006 | Schaefer et al. |
| 7,029,487 B2 | 4/2006 | Greene et al. |
| 7,033,374 B2 | 4/2006 | Schaefer et al. |
| 7,033,385 B2 | 4/2006 | Eder et al. |
| 7,037,327 B2 | 5/2006 | Salmon et al. |
| 7,037,330 B1 | 5/2006 | Rivelli et al. |
| 7,041,129 B2 | 5/2006 | Rourke et al. |
| 7,052,510 B1 | 5/2006 | Richter |
| 7,052,513 B2 | 5/2006 | Thompson |
| 7,060,091 B2 | 6/2006 | Killion et al. |
| 7,070,609 B2 | 7/2006 | West |
| 7,081,129 B2 | 7/2006 | Chobotov |
| 7,083,632 B2 | 8/2006 | Avellanet et al. |
| 7,083,640 B2 | 8/2006 | Lombardi et al. |
| 7,083,643 B2 | 8/2006 | Whalen et al. |
| 7,112,216 B2 | 9/2006 | Gregorich |
| 7,118,656 B2 | 10/2006 | Roth |
| 7,128,736 B1 | 10/2006 | Abrams et al. |
| 7,137,993 B2 | 11/2006 | Acosta et al. |
| 7,141,063 B2 | 11/2006 | White et al. |
| 7,147,655 B2 | 12/2006 | Chermoni |
| 7,147,659 B2 | 12/2006 | Jones |
| 7,147,660 B2 | 12/2006 | Chobotov et al. |
| 7,147,661 B2 | 12/2006 | Chobotov et al. |
| 7,153,323 B1 | 12/2006 | Teoh et al. |
| 7,156,871 B2 | 1/2007 | Jones et al. |
| 7,182,744 B2 | 2/2007 | Yamasaki et al. |
| 7,186,263 B2 | 3/2007 | Golds et al. |
| 7,195,636 B2 | 3/2007 | Avellanet et al. |
| 7,195,648 B2 | 3/2007 | Jones et al. |
| 7,201,762 B2 | 4/2007 | Greene et al. |
| 7,211,109 B2 | 5/2007 | Thompson |
| 7,220,270 B2 | 5/2007 | Sawhney et al. |
| 7,226,475 B2 | 6/2007 | Lenz et al. |
| 7,229,461 B2 | 6/2007 | Chin et al. |
| 7,231,260 B2 | 6/2007 | Wallace et al. |
| 7,232,461 B2 | 6/2007 | Ramer |
| 7,235,098 B2 | 6/2007 | Palmaz |
| 7,238,194 B2 | 7/2007 | Monstadt et al. |
| 7,241,301 B2 | 7/2007 | Thramann et al. |
| 7,241,308 B2 | 7/2007 | Andreas et al. |
| 7,244,261 B2 | 7/2007 | Lorenzo et al. |
| 7,247,159 B2 | 7/2007 | Lorenzo et al. |
| 7,288,112 B2 | 10/2007 | Denardo et al. |
| 7,294,123 B2 | 11/2007 | Jones et al. |
| 7,294,137 B2 | 11/2007 | Rivelli et al. |
| 7,294,146 B2 | 11/2007 | Chew et al. |
| 7,300,459 B2 | 11/2007 | Heuser |
| 7,300,661 B2 | 11/2007 | Henson et al. |
| 7,306,598 B2 | 12/2007 | Truckai et al. |
| 7,306,622 B2 | 12/2007 | Jones et al. |
| 7,306,624 B2 | 12/2007 | Yodfat et al. |
| 7,309,351 B2 | 12/2007 | Escamilla et al. |
| 7,309,352 B2 | 12/2007 | Eder et al. |
| 7,311,861 B2 | 12/2007 | Lanphere et al. |
| 7,323,005 B2 | 1/2008 | Wallace et al. |
| 7,326,225 B2 | 2/2008 | Ferrera et al. |
| 7,326,236 B2 | 2/2008 | Andreas et al. |

(56) References Cited

U.S. PATENT DOCUMENTS

| | | |
|---|---|---|
| 7,331,974 B2 | 2/2008 | Schaefer et al. |
| 7,338,511 B2 | 3/2008 | Mirigian et al. |
| 7,361,367 B2 | 4/2008 | Henson et al. |
| 7,374,568 B2 | 5/2008 | Whalen et al. |
| 7,384,426 B2 | 6/2008 | Wallace et al. |
| 7,402,169 B2 | 7/2008 | Killion et al. |
| 7,410,482 B2 | 8/2008 | Murphy et al. |
| 7,413,573 B2 | 8/2008 | Hartley et al. |
| 7,414,038 B2 | 8/2008 | Kinugasa et al. |
| 7,442,382 B2 | 10/2008 | Henson et al. |
| 7,449,236 B2 | 11/2008 | Lanphere et al. |
| 7,455,753 B2 | 11/2008 | Roth |
| 7,481,821 B2 | 1/2009 | Fogarty et al. |
| 7,483,558 B2 | 1/2009 | Greene et al. |
| 7,485,123 B2 | 2/2009 | Porter |
| 7,491,214 B2 | 2/2009 | Greene et al. |
| 7,491,226 B2 | 2/2009 | Palmaz et al. |
| 7,491,229 B2 | 2/2009 | Eder et al. |
| 7,520,893 B2 | 4/2009 | Rivelli |
| 7,537,609 B2 | 5/2009 | Davidson et al. |
| 7,547,321 B2 | 6/2009 | Silvestri et al. |
| 7,563,270 B2 | 7/2009 | Gumm |
| 7,569,066 B2 | 8/2009 | Gerberding et al. |
| 7,572,288 B2 | 8/2009 | Cox |
| 7,572,290 B2 | 8/2009 | Yodfat et al. |
| 7,588,597 B2 | 9/2009 | Frid |
| 7,588,780 B2 | 9/2009 | Buiser et al. |
| 7,588,825 B2 | 9/2009 | Bell et al. |
| 7,608,088 B2 | 10/2009 | Jones et al. |
| 7,611,530 B2 | 11/2009 | Pomeranz et al. |
| 7,615,071 B2 | 11/2009 | Chobotov |
| 7,621,928 B2 | 11/2009 | Thramann et al. |
| 7,641,680 B2 | 1/2010 | Palmaz et al. |
| 7,645,298 B2 | 1/2010 | Hartley et al. |
| 7,651,525 B2 | 1/2010 | Dolan |
| 7,666,220 B2 | 2/2010 | Evans et al. |
| 7,666,333 B2 | 2/2010 | Lanphere et al. |
| 7,691,124 B2 | 4/2010 | Balgobin |
| 7,695,484 B2 | 4/2010 | Wallace et al. |
| 7,695,488 B2 | 4/2010 | Berenstein et al. |
| 7,695,507 B2 | 4/2010 | Rivelli et al. |
| 7,695,509 B2 | 4/2010 | Rourke et al. |
| 7,704,274 B2 | 4/2010 | Boyle et al. |
| 7,708,754 B2 | 5/2010 | Balgobin et al. |
| 7,708,755 B2 | 5/2010 | Davis et al. |
| 7,713,264 B2 | 5/2010 | Murphy et al. |
| 7,736,671 B2 | 6/2010 | DiCarlo et al. |
| 7,744,610 B2 | 6/2010 | Hausen |
| 7,744,652 B2 | 6/2010 | Morsi |
| 7,749,242 B2 | 7/2010 | Tran et al. |
| 7,758,892 B1 | 7/2010 | Chen et al. |
| 7,763,011 B2 | 7/2010 | Ortiz et al. |
| 7,766,933 B2 | 8/2010 | Davis et al. |
| 7,766,955 B2 | 8/2010 | Vardi et al. |
| 7,769,603 B2 | 8/2010 | Jung et al. |
| 7,776,079 B2 | 8/2010 | Gumm |
| 7,780,645 B2 | 8/2010 | Jones |
| 7,780,719 B2 | 8/2010 | Killion et al. |
| 7,799,047 B2 | 9/2010 | Greene et al. |
| 7,799,052 B2 | 9/2010 | Balgobin et al. |
| 7,803,179 B2 | 9/2010 | Denison |
| 7,803,180 B2 | 9/2010 | Burpee et al. |
| 7,811,300 B2 | 10/2010 | Feller et al. |
| 7,811,305 B2 | 10/2010 | Balgobin et al. |
| 7,818,084 B2 | 10/2010 | Boyden et al. |
| 7,819,891 B2 | 10/2010 | Balgobin et al. |
| 7,819,892 B2 | 10/2010 | Balgobin et al. |
| 7,842,054 B2 | 11/2010 | Greene et al. |
| 7,842,377 B2 | 11/2010 | Lanphere et al. |
| 7,850,725 B2 | 12/2010 | Vardi et al. |
| 7,857,843 B2 | 12/2010 | Henderson |
| 7,862,608 B2 | 1/2011 | Hogendijk et al. |
| 7,875,044 B2 | 1/2011 | Feller et al. |
| 7,883,526 B2 | 2/2011 | Jones et al. |
| 7,892,273 B2 | 2/2011 | George et al. |
| 7,892,279 B2 | 2/2011 | Davidson et al. |
| 7,896,899 B2 | 3/2011 | Patterson et al. |
| 7,901,445 B2 | 3/2011 | Wallace et al. |
| 7,905,913 B2 | 3/2011 | Chew et al. |
| 7,914,574 B2 | 3/2011 | Schmid et al. |
| 7,914,639 B2 | 3/2011 | Layne et al. |
| 7,918,881 B2 | 4/2011 | Andreas et al. |
| 7,922,755 B2 | 4/2011 | Acosta et al. |
| 7,935,142 B2 | 5/2011 | Gregorich |
| 7,938,845 B2 | 5/2011 | Aganon et al. |
| 7,942,925 B2 | 5/2011 | Yodfat et al. |
| 7,947,071 B2 | 5/2011 | Schmid et al. |
| 7,955,382 B2 | 6/2011 | Flanagan et al. |
| 7,959,662 B2 | 6/2011 | Erbel et al. |
| 7,963,987 B2 | 6/2011 | Melsheimer et al. |
| 7,976,527 B2 | 7/2011 | Cragg et al. |
| 7,976,823 B2 | 7/2011 | Lanphere et al. |
| 7,985,238 B2 | 7/2011 | Balgobin et al. |
| 7,988,721 B2 | 8/2011 | Morris et al. |
| 7,993,364 B2 | 8/2011 | Morsi |
| 8,002,789 B2 | 8/2011 | Ramzipoor et al. |
| 8,003,180 B2 | 8/2011 | Goffena et al. |
| 8,007,529 B2 | 8/2011 | Yan |
| 8,012,192 B2 | 9/2011 | Eidenschink et al. |
| 8,012,197 B2 | 9/2011 | Bashiri et al. |
| 8,016,853 B2 | 9/2011 | Griffen et al. |
| 8,016,870 B2 | 9/2011 | Chew et al. |
| 8,016,871 B2 | 9/2011 | Chew et al. |
| 8,016,876 B2 | 9/2011 | Gregorich et al. |
| 8,016,878 B2 | 9/2011 | Meyer et al. |
| 8,019,413 B2 | 9/2011 | Ferren et al. |
| 8,021,416 B2 | 9/2011 | Abrams |
| 8,024,036 B2 | 9/2011 | Ferren et al. |
| 8,034,073 B2 | 10/2011 | Davis et al. |
| 8,038,706 B2 | 10/2011 | Eidenschink et al. |
| 8,038,708 B2 | 10/2011 | Case et al. |
| 8,048,140 B2 | 11/2011 | Purdy |
| 8,052,736 B2 | 11/2011 | Doig et al. |
| 8,057,495 B2 | 11/2011 | Pal et al. |
| 8,062,379 B2 | 11/2011 | Morsi |
| 8,066,036 B2 | 11/2011 | Monetti et al. |
| 8,067,071 B2 | 11/2011 | Farnsworth et al. |
| 8,070,792 B2 | 12/2011 | Gregorich et al. |
| 8,075,585 B2 | 12/2011 | Lee et al. |
| 8,095,382 B2 | 1/2012 | Boyden et al. |
| 8,100,960 B2 | 1/2012 | Bruszewski |
| 8,133,256 B2 | 3/2012 | Wilson et al. |
| 8,142,456 B2 | 3/2012 | Rosqueta et al. |
| 8,147,534 B2 | 4/2012 | Berez et al. |
| 8,147,537 B2 | 4/2012 | Boyden et al. |
| 8,163,003 B2 | 4/2012 | Boyden et al. |
| 8,172,862 B2 | 5/2012 | Wallace et al. |
| 8,172,895 B2 | 5/2012 | Anderson et al. |
| 8,187,315 B1 | 5/2012 | Clauson et al. |
| 8,202,292 B2 | 6/2012 | Kellett |
| 8,211,141 B2 | 7/2012 | Davis et al. |
| 8,211,160 B2 | 7/2012 | Garrison et al. |
| 8,221,447 B2 | 7/2012 | Solar et al. |
| 8,226,660 B2 | 7/2012 | Teoh et al. |
| 8,226,706 B2 | 7/2012 | Hartley et al. |
| 8,236,042 B2 | 8/2012 | Berez et al. |
| 8,246,672 B2 | 8/2012 | Osborne |
| 8,252,040 B2 | 8/2012 | Cox |
| 8,257,421 B2 | 9/2012 | Berez et al. |
| 8,257,430 B2 | 9/2012 | Covalin et al. |
| 8,257,431 B2 | 9/2012 | Henderson et al. |
| 8,262,607 B2 | 9/2012 | Porter |
| 8,262,686 B2 | 9/2012 | Fogarty et al. |
| 8,267,923 B2 | 9/2012 | Murphy et al. |
| 8,267,955 B2 | 9/2012 | Patterson et al. |
| 8,267,985 B2 | 9/2012 | Garcia et al. |
| 8,267,986 B2 | 9/2012 | Berez et al. |
| 8,273,100 B2 | 9/2012 | Martinez |
| 8,273,101 B2 | 9/2012 | Garcia et al. |
| 8,277,500 B2 | 10/2012 | Schmid et al. |
| 8,282,679 B2 | 10/2012 | Denison |
| 8,292,914 B2 | 10/2012 | Morsi |
| 8,292,944 B2 | 10/2012 | Schmid et al. |
| 8,308,751 B2 | 11/2012 | Gerberding |

(56) References Cited

U.S. PATENT DOCUMENTS

| | | |
|---|---|---|
| 8,313,504 B2 | 11/2012 | Do et al. |
| 8,323,306 B2 | 12/2012 | Schaefer et al. |
| 8,328,860 B2 | 12/2012 | Strauss et al. |
| 8,353,943 B2 | 1/2013 | Kuppurathanam et al. |
| 8,357,178 B2 | 1/2013 | Grandfield et al. |
| 8,357,179 B2 | 1/2013 | Grandfield et al. |
| 8,357,180 B2 | 1/2013 | Feller et al. |
| 8,361,104 B2 | 1/2013 | Jones et al. |
| 8,361,106 B2 | 1/2013 | Solar et al. |
| 8,372,062 B2 | 2/2013 | Murphy et al. |
| 8,372,114 B2 | 2/2013 | Hines |
| 8,377,091 B2 | 2/2013 | Cruise et al. |
| 8,377,112 B2 | 2/2013 | Griffin et al. |
| 8,377,241 B2 | 2/2013 | Farnsworth et al. |
| 8,382,825 B2 | 2/2013 | Garcia et al. |
| 8,388,650 B2 | 3/2013 | Gerberding et al. |
| 8,388,677 B2 | 3/2013 | Herrmann |
| 8,394,136 B2 | 3/2013 | Hartley et al. |
| 8,398,670 B2 | 3/2013 | Amplatz et al. |
| 8,398,701 B2 | 3/2013 | Berez et al. |
| 8,409,267 B2 | 4/2013 | Berez et al. |
| 8,409,269 B2 | 4/2013 | Berez et al. |
| 8,414,637 B2 | 4/2013 | Chouinard |
| 8,419,787 B2 | 4/2013 | Yodfat et al. |
| 8,425,541 B2 | 4/2013 | Masters et al. |
| 8,425,542 B2 | 4/2013 | Moftakhar et al. |
| 8,425,548 B2 | 4/2013 | Connor |
| 8,430,922 B2 | 4/2013 | Jung et al. |
| 8,439,942 B2 | 5/2013 | Moran et al. |
| 8,444,667 B2 | 5/2013 | Porter |
| 8,444,668 B2 | 5/2013 | Jones et al. |
| 8,444,686 B2 | 5/2013 | Holman et al. |
| 8,449,532 B2 | 5/2013 | Murphy et al. |
| 8,449,592 B2 | 5/2013 | Wilson et al. |
| 8,454,649 B2 | 6/2013 | Cragg et al. |
| 8,460,240 B2 | 6/2013 | Towler |
| 8,470,013 B2 | 6/2013 | Duggal et al. |
| 8,470,035 B2 | 6/2013 | Cruise et al. |
| 8,473,030 B2 | 6/2013 | Greenan et al. |
| 8,475,517 B2 | 7/2013 | Jung et al. |
| 8,478,437 B2 | 7/2013 | Boyden et al. |
| 8,480,727 B2 | 7/2013 | Clarke |
| 8,486,101 B2 | 7/2013 | Tran et al. |
| 8,491,459 B2 | 7/2013 | Yun |
| 8,491,646 B2 | 7/2013 | Schreck |
| 8,500,788 B2 | 8/2013 | Berez et al. |
| 8,506,618 B2 | 8/2013 | Chouinard et al. |
| 8,506,619 B2 | 8/2013 | Ortiz et al. |
| 8,512,219 B2 | 8/2013 | Ferren et al. |
| 8,512,395 B2 | 8/2013 | Meyer et al. |
| 8,523,934 B2 | 9/2013 | Purdy |
| 8,529,556 B2 | 9/2013 | Murphy et al. |
| 8,529,596 B2 | 9/2013 | Grandfield et al. |
| 8,529,614 B2 | 9/2013 | Berez et al. |
| 8,529,616 B2 | 9/2013 | Boyle et al. |
| 8,529,619 B2 | 9/2013 | Abrams |
| 8,535,367 B2 | 9/2013 | Kim et al. |
| 8,535,590 B2 | 9/2013 | Milner et al. |
| 8,550,344 B2 | 10/2013 | Jung et al. |
| 8,551,155 B2 | 10/2013 | Jung et al. |
| 8,556,953 B2 | 10/2013 | Berez et al. |
| 8,562,636 B2 | 10/2013 | Fogarty et al. |
| 8,562,667 B2 | 10/2013 | Cox |
| 8,577,693 B2 | 11/2013 | Jung et al. |
| 8,597,320 B2 | 12/2013 | Sepetka et al. |
| 8,597,321 B2 | 12/2013 | Monstadt et al. |
| 8,597,323 B1 | 12/2013 | Plaza et al. |
| 8,597,342 B2 | 12/2013 | McKinsey et al. |
| 8,597,745 B2 | 12/2013 | Farnsworth et al. |
| 8,617,132 B2 | 12/2013 | Golzarian et al. |
| 8,623,071 B2 | 1/2014 | Lundkvist et al. |
| 8,636,760 B2 | 1/2014 | Garcia et al. |
| 8,647,377 B2 | 2/2014 | Kim et al. |
| 8,657,865 B2 | 2/2014 | Gumm |
| 8,663,309 B2 | 3/2014 | Chobotov |
| 8,668,716 B2 | 3/2014 | Hines |
| 8,668,717 B2 | 3/2014 | Hines |
| 8,671,815 B2 | 3/2014 | Hancock et al. |
| 8,696,701 B2 | 4/2014 | Becking et al. |
| 8,709,062 B2 | 4/2014 | Dusbabek et al. |
| 8,709,065 B2 | 4/2014 | Chobotov |
| 8,715,312 B2 | 5/2014 | Burke et al. |
| 8,715,317 B1 | 5/2014 | Janardhan et al. |
| 8,715,336 B2 | 5/2014 | Chu et al. |
| 8,721,706 B2 | 5/2014 | Jung et al. |
| 8,728,094 B2 | 5/2014 | Roorda et al. |
| 8,728,145 B2 | 5/2014 | Chuter et al. |
| 8,728,146 B2 | 5/2014 | Gregorich et al. |
| 8,734,502 B2 | 5/2014 | Orr |
| 8,740,966 B2 | 6/2014 | Brocker et al. |
| 8,747,430 B2 | 6/2014 | Porter |
| 8,747,432 B1 | 6/2014 | Janardhan et al. |
| 8,747,455 B2 | 6/2014 | Greenberg |
| 8,747,597 B2 | 6/2014 | Rosqueta et al. |
| 8,753,371 B1 | 6/2014 | Janardhan et al. |
| 8,764,788 B2 | 7/2014 | Martinez |
| 8,769,796 B2 | 7/2014 | Bourang et al. |
| 8,771,294 B2 | 7/2014 | Sepetka et al. |
| 8,771,341 B2 | 7/2014 | Strauss et al. |
| 8,771,342 B2 | 7/2014 | Vardi |
| 8,784,446 B1 | 7/2014 | Janardhan et al. |
| 8,784,475 B2 | 7/2014 | Martinson et al. |
| 8,784,477 B2 | 7/2014 | Bregulla et al. |
| 8,795,345 B2 | 8/2014 | Grandfield et al. |
| 8,795,346 B2 | 8/2014 | Alkhatib |
| 8,795,347 B2 | 8/2014 | Bourang et al. |
| 8,801,772 B2 | 8/2014 | Shobayashi et al. |
| 8,808,347 B2 | 8/2014 | Bourang et al. |
| 8,808,361 B2 | 8/2014 | Strauss et al. |
| 8,813,625 B1 | 8/2014 | Janardhan et al. |
| 8,821,564 B2 | 9/2014 | Schreck et al. |
| 8,828,071 B2 | 9/2014 | Bourang et al. |
| 8,840,867 B2 | 9/2014 | Sophie et al. |
| 8,845,679 B1 | 9/2014 | Janardhan et al. |
| 2001/0000797 A1 | 5/2001 | Mazzocchi |
| 2001/0001835 A1 | 5/2001 | Greene, Jr. et al. |
| 2001/0009996 A1 | 7/2001 | Ferrera et al. |
| 2001/0016766 A1 | 8/2001 | Vardi et al. |
| 2001/0037137 A1 | 11/2001 | Vardi et al. |
| 2001/0056281 A1 | 12/2001 | Wallace et al. |
| 2002/0002382 A1 | 1/2002 | Wallace et al. |
| 2002/0018752 A1 | 2/2002 | Krall et al. |
| 2002/0042628 A1 | 4/2002 | Chin et al. |
| 2002/0058962 A1 | 5/2002 | Wallace et al. |
| 2002/0082620 A1 | 6/2002 | Lee |
| 2002/0082636 A1 | 6/2002 | Sawhney et al. |
| 2002/0087077 A1 | 7/2002 | Wallace et al. |
| 2002/0107534 A1 | 8/2002 | Schaefer et al. |
| 2002/0116047 A1 | 8/2002 | Vardi et al. |
| 2002/0120276 A1 | 8/2002 | Greene et al. |
| 2002/0128671 A1 | 9/2002 | Wallace et al. |
| 2002/0133190 A1 | 9/2002 | Horton et al. |
| 2002/0143348 A1 | 10/2002 | Wallace et al. |
| 2002/0151926 A1 | 10/2002 | Wallace et al. |
| 2002/0151965 A1 | 10/2002 | Roth |
| 2002/0156516 A1 | 10/2002 | Vardi et al. |
| 2002/0169473 A1 | 11/2002 | Sepetka et al. |
| 2002/0177855 A1 | 11/2002 | Greene et al. |
| 2003/0014007 A1 | 1/2003 | Eidenschink et al. |
| 2003/0014075 A1 | 1/2003 | Rosenbluth et al. |
| 2003/0018294 A1 | 1/2003 | Cox |
| 2003/0018356 A1 | 1/2003 | Schaefer et al. |
| 2003/0065375 A1 | 4/2003 | Eskuri |
| 2003/0074049 A1 | 4/2003 | Hoganson et al. |
| 2003/0074056 A1 | 4/2003 | Killion et al. |
| 2003/0083676 A1 | 5/2003 | Wallace |
| 2003/0083737 A1 | 5/2003 | Greene et al. |
| 2003/0088311 A1 | 5/2003 | Greene et al. |
| 2003/0093097 A1 | 5/2003 | Avellanet et al. |
| 2003/0093108 A1 | 5/2003 | Avellanet et al. |
| 2003/0093111 A1 | 5/2003 | Ken et al. |
| 2003/0100945 A1 | 5/2003 | Yodfat et al. |
| 2003/0109917 A1 | 6/2003 | Rudin et al. |
| 2003/0130689 A1 | 7/2003 | Wallace et al. |

(56) References Cited

U.S. PATENT DOCUMENTS

| | | |
|---|---|---|
| 2003/0135264 A1 | 7/2003 | Whalen et al. |
| 2003/0139802 A1 | 7/2003 | Wulfman et al. |
| 2003/0159920 A1 | 8/2003 | Roth |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2003/0195606 A1 | 10/2003 | Davidson et al. |
| 2003/0223955 A1 | 12/2003 | Whalen et al. |
| 2004/0002752 A1 | 1/2004 | Griffin et al. |
| 2004/0015227 A1 | 1/2004 | Vardi et al. |
| 2004/0045554 A1 | 3/2004 | Schaefer et al. |
| 2004/0059370 A1 | 3/2004 | Greene et al. |
| 2004/0091543 A1 | 5/2004 | Bell et al. |
| 2004/0093014 A1 | 5/2004 | Ho et al. |
| 2004/0098027 A1 | 5/2004 | Teoh et al. |
| 2004/0098028 A1 | 5/2004 | Martinez |
| 2004/0111112 A1 | 6/2004 | Hoffmann |
| 2004/0111142 A1 | 6/2004 | Rourke et al. |
| 2004/0115164 A1 | 6/2004 | Pierce et al. |
| 2004/0158282 A1 | 8/2004 | Jones et al. |
| 2004/0161451 A1 | 8/2004 | Pierce et al. |
| 2004/0181253 A1 | 9/2004 | Sepetka et al. |
| 2004/0186551 A1 | 9/2004 | Kao et al. |
| 2004/0193246 A1 | 9/2004 | Ferrera |
| 2004/0210249 A1 | 10/2004 | Fogarty et al. |
| 2004/0215331 A1 | 10/2004 | Chew et al. |
| 2004/0220663 A1 | 11/2004 | Rivelli, Jr. |
| 2004/0243168 A1 | 12/2004 | Ferrera et al. |
| 2004/0243216 A1 | 12/2004 | Gregorich |
| 2004/0249435 A1 | 12/2004 | Andreas et al. |
| 2004/0249439 A1 | 12/2004 | Richter et al. |
| 2004/0260384 A1 | 12/2004 | Allen |
| 2005/0004660 A1 | 1/2005 | Rosenbluth et al. |
| 2005/0010281 A1 | 1/2005 | Yodfat et al. |
| 2005/0015110 A1 | 1/2005 | Fogarty et al. |
| 2005/0021077 A1 | 1/2005 | Chin et al. |
| 2005/0033349 A1 | 2/2005 | Jones et al. |
| 2005/0033350 A1 | 2/2005 | Ken et al. |
| 2005/0065592 A1 | 3/2005 | Holzer |
| 2005/0075405 A1 | 4/2005 | Wilson et al. |
| 2005/0080445 A1 | 4/2005 | Sawhney et al. |
| 2005/0090888 A1 | 4/2005 | Hines et al. |
| 2005/0095428 A1 | 5/2005 | Dicarlo et al. |
| 2005/0096728 A1 | 5/2005 | Ramer |
| 2005/0107863 A1 | 5/2005 | Brown |
| 2005/0119687 A1 | 6/2005 | Dacey et al. |
| 2005/0131516 A1 | 6/2005 | Greenhalgh |
| 2005/0131518 A1 | 6/2005 | Hartley et al. |
| 2005/0133046 A1 | 6/2005 | Becker et al. |
| 2005/0149159 A1 | 7/2005 | Andreas et al. |
| 2005/0149164 A1 | 7/2005 | Rivelli |
| 2005/0171572 A1 | 8/2005 | Martinez |
| 2005/0171597 A1 | 8/2005 | Boatman et al. |
| 2005/0192618 A1 | 9/2005 | Porter |
| 2005/0192621 A1 | 9/2005 | Wallace et al. |
| 2005/0192661 A1 | 9/2005 | Griffen et al. |
| 2005/0209674 A1 | 9/2005 | Kutscher et al. |
| 2005/0228434 A1 | 10/2005 | Amplatz et al. |
| 2005/0251247 A1 | 11/2005 | Roth |
| 2005/0267510 A1 | 12/2005 | Razack |
| 2005/0267568 A1 | 12/2005 | Berez et al. |
| 2005/0277978 A1 | 12/2005 | Greenhalgh |
| 2005/0283220 A1 | 12/2005 | Gobran et al. |
| 2006/0036045 A1 | 2/2006 | Wilson et al. |
| 2006/0036281 A1 | 2/2006 | Patterson et al. |
| 2006/0052816 A1 | 3/2006 | Bates et al. |
| 2006/0058834 A1 | 3/2006 | Do et al. |
| 2006/0079923 A1 | 4/2006 | Chhabra et al. |
| 2006/0085061 A1 | 4/2006 | Vardi et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0136033 A1 | 6/2006 | Hermann et al. |
| 2006/0149299 A1 | 7/2006 | Greene et al. |
| 2006/0155323 A1 | 7/2006 | Porter et al. |
| 2006/0184195 A1 | 8/2006 | Schaefer et al. |
| 2006/0184196 A1 | 8/2006 | Schaefer et al. |
| 2006/0206196 A1 | 9/2006 | Porter |
| 2006/0206200 A1 | 9/2006 | Garcia et al. |
| 2006/0206201 A1 | 9/2006 | Garcia et al. |
| 2006/0224230 A1 | 10/2006 | Rivelli et al. |
| 2006/0229714 A1 | 10/2006 | Lombardi et al. |
| 2006/0235464 A1 | 10/2006 | Avellanet et al. |
| 2006/0241690 A1 | 10/2006 | Amplatz et al. |
| 2006/0241740 A1 | 10/2006 | Vardi et al. |
| 2006/0251695 A1 | 11/2006 | Henson et al. |
| 2006/0251700 A1 | 11/2006 | Henson et al. |
| 2006/0271149 A1 | 11/2006 | Berez et al. |
| 2006/0271153 A1 | 11/2006 | Garcia et al. |
| 2006/0276831 A1 | 12/2006 | Porter et al. |
| 2006/0292206 A1 | 12/2006 | Kim et al. |
| 2007/0016233 A1 | 1/2007 | Ferrera et al. |
| 2007/0021816 A1 | 1/2007 | Rudin |
| 2007/0031584 A1 | 2/2007 | Roth |
| 2007/0032855 A1 | 2/2007 | Davidson et al. |
| 2007/0050008 A1 | 3/2007 | Kim et al. |
| 2007/0055355 A1 | 3/2007 | Kim et al. |
| 2007/0060994 A1 | 3/2007 | Gobran et al. |
| 2007/0061005 A1 | 3/2007 | Kim et al. |
| 2007/0067015 A1 | 3/2007 | Jones et al. |
| 2007/0083257 A1 | 4/2007 | Pal et al. |
| 2007/0088368 A1 | 4/2007 | Acosta et al. |
| 2007/0088387 A1 | 4/2007 | Eskridge et al. |
| 2007/0100301 A1 | 5/2007 | Gumm |
| 2007/0106311 A1 | 5/2007 | Wallace et al. |
| 2007/0129786 A1 | 6/2007 | Beach et al. |
| 2007/0135907 A1 | 6/2007 | Wilson et al. |
| 2007/0150041 A1 | 6/2007 | Evans et al. |
| 2007/0150045 A1 | 6/2007 | Ferrera |
| 2007/0167747 A1 | 7/2007 | Borgert et al. |
| 2007/0175536 A1 | 8/2007 | Monetti et al. |
| 2007/0176333 A1 | 8/2007 | Greene et al. |
| 2007/0207186 A1 | 9/2007 | Scanlon et al. |
| 2007/0219578 A1 | 9/2007 | Solar et al. |
| 2007/0219610 A1 | 9/2007 | Israel |
| 2007/0219619 A1 | 9/2007 | Dieck et al. |
| 2007/0225794 A1 | 9/2007 | Thramann et al. |
| 2007/0239261 A1 | 10/2007 | Bose et al. |
| 2007/0265656 A1 | 11/2007 | Amplatz et al. |
| 2007/0299464 A1 | 12/2007 | Cruise et al. |
| 2007/0299498 A1 | 12/2007 | Perez et al. |
| 2008/0004653 A1 | 1/2008 | Sherman et al. |
| 2008/0004692 A1 | 1/2008 | Henson et al. |
| 2008/0031919 A1 | 2/2008 | Henson et al. |
| 2008/0033341 A1 | 2/2008 | Grad |
| 2008/0033366 A1 | 2/2008 | Matson et al. |
| 2008/0039933 A1 | 2/2008 | Yodfat et al. |
| 2008/0097495 A1 | 4/2008 | Feller et al. |
| 2008/0103585 A1 | 5/2008 | Monstadt et al. |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0147100 A1 | 6/2008 | Wallace |
| 2008/0152686 A1 | 6/2008 | Henson et al. |
| 2008/0161936 A1 | 7/2008 | Feller et al. |
| 2008/0195137 A1 | 8/2008 | Alleyne et al. |
| 2008/0200945 A1 | 8/2008 | Amplatz et al. |
| 2008/0221600 A1 | 9/2008 | Dieck et al. |
| 2008/0249608 A1 | 10/2008 | Dave |
| 2008/0281350 A1 | 11/2008 | Sepetka et al. |
| 2008/0312732 A1 | 12/2008 | Hartley et al. |
| 2008/0319521 A1 | 12/2008 | Norris et al. |
| 2008/0319525 A1 | 12/2008 | Tieu et al. |
| 2008/0319533 A1 | 12/2008 | Lehe |
| 2009/0062834 A1 | 3/2009 | Moftakhar et al. |
| 2009/0062841 A1 | 3/2009 | Amplatz et al. |
| 2009/0069880 A1 | 3/2009 | Vonderwalde et al. |
| 2009/0082846 A1 | 3/2009 | Chobotov |
| 2009/0088832 A1 | 4/2009 | Chew et al. |
| 2009/0105748 A1 | 4/2009 | Fogarty et al. |
| 2009/0112249 A1 | 4/2009 | Miles et al. |
| 2009/0112250 A1 | 4/2009 | Greene et al. |
| 2009/0118761 A1 | 5/2009 | Masters et al. |
| 2009/0125053 A1 | 5/2009 | Ferrera et al. |

(56) References Cited

U.S. PATENT DOCUMENTS

| | | |
|---|---|---|
| 2009/0132028 A1 | 5/2009 | Vardi et al. |
| 2009/0149864 A1 | 6/2009 | Porter |
| 2009/0164013 A1 | 6/2009 | Cruise et al. |
| 2009/0171437 A1 | 7/2009 | Brocker et al. |
| 2009/0177268 A1 | 7/2009 | Lundkvist et al. |
| 2009/0192536 A1 | 7/2009 | Berez et al. |
| 2009/0198318 A1 | 8/2009 | Berez et al. |
| 2009/0227976 A1 | 9/2009 | Calabria et al. |
| 2009/0228029 A1 | 9/2009 | Lee |
| 2009/0232869 A1 | 9/2009 | Greene et al. |
| 2009/0248135 A1 | 10/2009 | Bruszewski et al. |
| 2009/0254111 A1 | 10/2009 | Monstadt et al. |
| 2009/0270970 A1 | 10/2009 | Yodfat et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0292348 A1 | 11/2009 | Berez et al. |
| 2009/0297582 A1 | 12/2009 | Meyer et al. |
| 2009/0299326 A1 | 12/2009 | Morsi |
| 2009/0299390 A1 | 12/2009 | Dehnad |
| 2009/0299448 A1 | 12/2009 | Timko et al. |
| 2009/0318941 A1 | 12/2009 | Sepetka et al. |
| 2009/0318947 A1 | 12/2009 | Garcia et al. |
| 2009/0318948 A1 | 12/2009 | Linder et al. |
| 2009/0318949 A1 | 12/2009 | Ganpath et al. |
| 2009/0319017 A1 | 12/2009 | Berez et al. |
| 2009/0319023 A1 | 12/2009 | Hildebrand et al. |
| 2010/0004671 A1 | 1/2010 | Gerberding et al. |
| 2010/0004726 A1 | 1/2010 | Hancock et al. |
| 2010/0010624 A1 | 1/2010 | Berez et al. |
| 2010/0016833 A1 | 1/2010 | Ogle et al. |
| 2010/0023105 A1 | 1/2010 | Levy et al. |
| 2010/0036412 A1 | 2/2010 | Porter et al. |
| 2010/0042200 A1 | 2/2010 | Richter et al. |
| 2010/0063472 A1 | 3/2010 | Becker et al. |
| 2010/0063531 A1 | 3/2010 | Rudakov et al. |
| 2010/0069948 A1 | 3/2010 | Veznedaroglu et al. |
| 2010/0082091 A1 | 4/2010 | Berez et al. |
| 2010/0094335 A1 | 4/2010 | Gerberding et al. |
| 2010/0106240 A1 | 4/2010 | Duggal et al. |
| 2010/0114302 A1 | 5/2010 | Tzafriri et al. |
| 2010/0131002 A1 | 5/2010 | Connor et al. |
| 2010/0152828 A1 | 6/2010 | Pakbaz et al. |
| 2010/0152834 A1 | 6/2010 | Hannes et al. |
| 2010/0152837 A1 | 6/2010 | Lundkvist et al. |
| 2010/0168781 A1 | 7/2010 | Berenstein et al. |
| 2010/0174301 A1 | 7/2010 | Wallace et al. |
| 2010/0179640 A1 | 7/2010 | Reith |
| 2010/0179645 A1 | 7/2010 | Chen et al. |
| 2010/0198250 A1 | 8/2010 | Ricci et al. |
| 2010/0198334 A1 | 8/2010 | Yodfat et al. |
| 2010/0222804 A1 | 9/2010 | Murphy et al. |
| 2010/0222864 A1 | 9/2010 | Rivelli et al. |
| 2010/0274276 A1 | 10/2010 | Chow et al. |
| 2010/0274346 A1 | 10/2010 | Chouinard et al. |
| 2010/0280452 A1 | 11/2010 | Chen et al. |
| 2010/0305681 A1 | 12/2010 | Gumm |
| 2010/0312326 A1 | 12/2010 | Chuter et al. |
| 2010/0318173 A1 | 12/2010 | Kolandaivelu et al. |
| 2010/0324660 A1 | 12/2010 | Denison |
| 2011/0004294 A1 | 1/2011 | Bialas |
| 2011/0005062 A1 | 1/2011 | Greene et al. |
| 2011/0009940 A1 | 1/2011 | Grandfield et al. |
| 2011/0009941 A1 | 1/2011 | Grandfield et al. |
| 2011/0009950 A1 | 1/2011 | Grandfield et al. |
| 2011/0022149 A1 | 1/2011 | Cox et al. |
| 2011/0039967 A1 | 2/2011 | Wilson et al. |
| 2011/0046658 A1 | 2/2011 | Connor et al. |
| 2011/0046716 A1 | 2/2011 | Parkinson et al. |
| 2011/0054511 A1 | 3/2011 | Henson et al. |
| 2011/0054589 A1 | 3/2011 | Bashiri et al. |
| 2011/0066221 A1 | 3/2011 | White et al. |
| 2011/0082427 A1 | 4/2011 | Golzarian et al. |
| 2011/0082491 A1 | 4/2011 | Sepetka et al. |
| 2011/0082533 A1 | 4/2011 | Vardi et al. |
| 2011/0089592 A1 | 4/2011 | Farnsworth et al. |
| 2011/0092997 A1 | 4/2011 | Kang |
| 2011/0098814 A1 | 4/2011 | Monstadt et al. |
| 2011/0118777 A1 | 5/2011 | Patterson et al. |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0144686 A1 | 6/2011 | Wilson et al. |
| 2011/0144740 A1 | 6/2011 | Molaei et al. |
| 2011/0152993 A1 | 6/2011 | Marchand et al. |
| 2011/0152996 A1 | 6/2011 | Acosta et al. |
| 2011/0152998 A1 | 6/2011 | Berez et al. |
| 2011/0166588 A1 | 7/2011 | Connor et al. |
| 2011/0166592 A1 | 7/2011 | Garcia et al. |
| 2011/0166641 A1 | 7/2011 | Bales et al. |
| 2011/0182998 A1 | 7/2011 | Reb et al. |
| 2011/0184451 A1 | 7/2011 | Sahl |
| 2011/0184452 A1 | 7/2011 | Huynh et al. |
| 2011/0184453 A1 | 7/2011 | Levy et al. |
| 2011/0184454 A1 | 7/2011 | Barry et al. |
| 2011/0184455 A1 | 7/2011 | Keeley et al. |
| 2011/0184456 A1 | 7/2011 | Grandfield et al. |
| 2011/0196413 A1 | 8/2011 | Wallace et al. |
| 2011/0202085 A1 | 8/2011 | Loganathan et al. |
| 2011/0208227 A1 | 8/2011 | Becking |
| 2011/0213406 A1 | 9/2011 | Aganon et al. |
| 2011/0224776 A1 | 9/2011 | Sepetka et al. |
| 2011/0230957 A1 | 9/2011 | Bonsignore et al. |
| 2011/0238105 A1 | 9/2011 | Gelbart et al. |
| 2011/0245862 A1 | 10/2011 | Dieck et al. |
| 2011/0245863 A1 | 10/2011 | Martinez |
| 2011/0264192 A1 | 10/2011 | Hartley et al. |
| 2011/0265943 A1 | 11/2011 | Rosqueta et al. |
| 2011/0276071 A1 | 11/2011 | Connor et al. |
| 2011/0282378 A1 | 11/2011 | Murphy et al. |
| 2011/0286925 A1 | 11/2011 | Lerouge et al. |
| 2011/0288627 A1 | 11/2011 | Hartley et al. |
| 2011/0307044 A1 | 12/2011 | Bourang et al. |
| 2011/0307045 A1 | 12/2011 | Bourang et al. |
| 2011/0307046 A1 | 12/2011 | Bourang et al. |
| 2011/0307052 A1 | 12/2011 | Bourang et al. |
| 2011/0313443 A1 | 12/2011 | Lorenzo et al. |
| 2011/0313512 A1 | 12/2011 | Hartley et al. |
| 2011/0319926 A1 | 12/2011 | Becking et al. |
| 2011/0319928 A1 | 12/2011 | Griffin et al. |
| 2012/0004682 A1 | 1/2012 | Connor |
| 2012/0004719 A1 | 1/2012 | Gregorich et al. |
| 2012/0016462 A1 | 1/2012 | Gregorich et al. |
| 2012/0041540 A1 | 2/2012 | Shobayashi |
| 2012/0046676 A1 | 2/2012 | Morsi |
| 2012/0053670 A1 | 3/2012 | Purdy |
| 2012/0055614 A1 | 3/2012 | Hancock et al. |
| 2012/0071911 A1 | 3/2012 | Sadasivan et al. |
| 2012/0078285 A1 | 3/2012 | Griffin |
| 2012/0089174 A1 | 4/2012 | Chen et al. |
| 2012/0116352 A1 | 5/2012 | Rangi |
| 2012/0116441 A1 | 5/2012 | Yamanaka et al. |
| 2012/0116442 A1 | 5/2012 | Monstadt et al. |
| 2012/0130479 A1 | 5/2012 | Chuter et al. |
| 2012/0143237 A1 | 6/2012 | Cam et al. |
| 2012/0143317 A1 | 6/2012 | Cam et al. |
| 2012/0165919 A1 | 6/2012 | Cox et al. |
| 2012/0165920 A1 | 6/2012 | Meyer et al. |
| 2012/0172921 A1 | 7/2012 | Yamanaka et al. |
| 2012/0172972 A1 | 7/2012 | Meyer et al. |
| 2012/0172977 A1 | 7/2012 | Bregulla et al. |
| 2012/0179192 A1 | 7/2012 | Fogarty et al. |
| 2012/0197283 A1 | 8/2012 | Marchand et al. |
| 2012/0209309 A1 | 8/2012 | Chen et al. |
| 2012/0209311 A1 | 8/2012 | Grandfield et al. |
| 2012/0215250 A1 | 8/2012 | Grandfield et al. |
| 2012/0221095 A1 | 8/2012 | Berez et al. |
| 2012/0238644 A1 | 9/2012 | Gong et al. |
| 2012/0239074 A1 | 9/2012 | Aboytes et al. |
| 2012/0245674 A1 | 9/2012 | Molaei et al. |

(56) References Cited

U.S. PATENT DOCUMENTS

| | | |
|---|---|---|
| 2012/0245675 A1 | 9/2012 | Molaei et al. |
| 2012/0253369 A1 | 10/2012 | Morsi |
| 2012/0253377 A1 | 10/2012 | Slazas et al. |
| 2012/0253448 A1 | 10/2012 | Hartley et al. |
| 2012/0259354 A1 | 10/2012 | Kellett |
| 2012/0259404 A1 | 10/2012 | Tieu et al. |
| 2012/0265287 A1 | 10/2012 | Sharma et al. |
| 2012/0271200 A1 | 10/2012 | Martinson et al. |
| 2012/0271399 A1 | 10/2012 | Perkins et al. |
| 2012/0277784 A1 | 11/2012 | Berez et al. |
| 2012/0283764 A1 | 11/2012 | Solar et al. |
| 2012/0283765 A1 | 11/2012 | Berez et al. |
| 2012/0283768 A1 | 11/2012 | Cox et al. |
| 2012/0283769 A1 | 11/2012 | Cruise et al. |
| 2012/0283815 A1 | 11/2012 | Berez et al. |
| 2012/0289995 A1 | 11/2012 | Constant et al. |
| 2012/0296361 A1 | 11/2012 | Cam et al. |
| 2012/0296362 A1 | 11/2012 | Cam et al. |
| 2012/0303052 A1 | 11/2012 | Connor |
| 2012/0303108 A1 | 11/2012 | Fogarty et al. |
| 2012/0303112 A1 | 11/2012 | Armstrong et al. |
| 2012/0310270 A1 | 12/2012 | Murphy et al. |
| 2012/0310271 A1 | 12/2012 | Kwon |
| 2012/0310611 A1 | 12/2012 | Sadasivan et al. |
| 2012/0316598 A1 | 12/2012 | Becking et al. |
| 2012/0316632 A1 | 12/2012 | Gao |
| 2012/0316638 A1 | 12/2012 | Grad et al. |
| 2012/0323268 A1 | 12/2012 | Martinez |
| 2012/0323309 A1 | 12/2012 | Cattaneo |
| 2012/0323547 A1 | 12/2012 | Baloch et al. |
| 2012/0330341 A1 | 12/2012 | Becking et al. |
| 2012/0330343 A1 | 12/2012 | Kim et al. |
| 2012/0330347 A1 | 12/2012 | Becking et al. |
| 2012/0330402 A1 | 12/2012 | Vad et al. |
| 2013/0012979 A1 | 1/2013 | Amplatz et al. |
| 2013/0018220 A1 | 1/2013 | Vad et al. |
| 2013/0018409 A1 | 1/2013 | Le et al. |
| 2013/0023903 A1 | 1/2013 | Roorda et al. |
| 2013/0035712 A1 | 2/2013 | Theobald et al. |
| 2013/0041454 A1 | 2/2013 | Dobson et al. |
| 2013/0045182 A1 | 2/2013 | Gong et al. |
| 2013/0046371 A1 | 2/2013 | Greenberg et al. |
| 2013/0053872 A1 | 2/2013 | Hansen |
| 2013/0053944 A1 | 2/2013 | Welch |
| 2013/0060317 A1 | 3/2013 | Dusbabek et al. |
| 2013/0060322 A1 | 3/2013 | Leynov et al. |
| 2013/0066357 A1 | 3/2013 | Aboytes et al. |
| 2013/0066359 A1 | 3/2013 | Murphy et al. |
| 2013/0066360 A1 | 3/2013 | Becking et al. |
| 2013/0066413 A1 | 3/2013 | Jin et al. |
| 2013/0066415 A1 | 3/2013 | Hocking |
| 2013/0072959 A1 | 3/2013 | Wu et al. |
| 2013/0085518 A1 | 4/2013 | Trommeter et al. |
| 2013/0085522 A1 | 4/2013 | Becking et al. |
| 2013/0089576 A1 | 4/2013 | Maitland et al. |
| 2013/0090682 A1 | 4/2013 | Bachman et al. |
| 2013/0090719 A1 | 4/2013 | Bales et al. |
| 2013/0090721 A1 | 4/2013 | Bales et al. |
| 2013/0095087 A1 | 4/2013 | Shalaby et al. |
| 2013/0103074 A1 | 4/2013 | Riina et al. |
| 2013/0103135 A1 | 4/2013 | Vinluan |
| 2013/0108574 A1 | 5/2013 | Chevalier et al. |
| 2013/0116659 A1 | 5/2013 | Porter |
| 2013/0116722 A1 | 5/2013 | Aboytes et al. |
| 2013/0116774 A1 | 5/2013 | Strauss et al. |
| 2013/0123830 A1 | 5/2013 | Becking et al. |
| 2013/0123899 A1 | 5/2013 | Leopold et al. |
| 2013/0123901 A1 | 5/2013 | Connor et al. |
| 2013/0131711 A1 | 5/2013 | Bowman |
| 2013/0131716 A1 | 5/2013 | Cruise et al. |
| 2013/0131780 A1 | 5/2013 | Armstrong et al. |
| 2013/0131786 A1 | 5/2013 | Chobotov |
| 2013/0146173 A1 | 6/2013 | Krivoruchko et al. |
| 2013/0150946 A1 | 6/2013 | Hartley et al. |
| 2013/0166010 A1 | 6/2013 | Vad |
| 2013/0166017 A1 | 6/2013 | Cartledge et al. |
| 2013/0172925 A1 | 7/2013 | Garcia et al. |
| 2013/0172975 A1 | 7/2013 | Berez et al. |
| 2013/0172976 A1 | 7/2013 | Garcia et al. |
| 2013/0190795 A1 | 7/2013 | Matson et al. |
| 2013/0190800 A1 | 7/2013 | Murphy et al. |
| 2013/0190805 A1 | 7/2013 | Slazas et al. |
| 2013/0197547 A1 | 8/2013 | Fukuoka et al. |
| 2013/0197570 A1 | 8/2013 | Ebata et al. |
| 2013/0197617 A1 | 8/2013 | Armstrong et al. |
| 2013/0197624 A1 | 8/2013 | Armstrong et al. |
| 2013/0204288 A1 | 8/2013 | Johnson et al. |
| 2013/0204289 A1 | 8/2013 | Dasnurkar et al. |
| 2013/0204290 A1 | 8/2013 | Clarke et al. |
| 2013/0204347 A1 | 8/2013 | Armstrong et al. |
| 2013/0204351 A1 | 8/2013 | Cox et al. |
| 2013/0204354 A1 | 8/2013 | Adams |
| 2013/0211443 A1 | 8/2013 | Cragg et al. |
| 2013/0211492 A1 | 8/2013 | Schneider et al. |
| 2013/0211497 A1 | 8/2013 | Charlebois et al. |
| 2013/0211498 A1 | 8/2013 | Buckley et al. |
| 2013/0211505 A1 | 8/2013 | Robison |
| 2013/0211507 A1 | 8/2013 | LaDuca et al. |
| 2013/0218191 A1 | 8/2013 | Heltai |
| 2013/0226276 A1 | 8/2013 | Newell et al. |
| 2013/0226278 A1 | 8/2013 | Newell et al. |
| 2013/0231695 A1 | 9/2013 | Malek |
| 2013/0231732 A1 | 9/2013 | Vonderwalde et al. |
| 2013/0238083 A1 | 9/2013 | Duggal et al. |
| 2013/0245606 A1 | 9/2013 | Stam et al. |
| 2013/0245667 A1 | 9/2013 | Marchand et al. |
| 2013/0245745 A1 | 9/2013 | Vong et al. |
| 2013/0252900 A1 | 9/2013 | Reb et al. |
| 2013/0253086 A1 | 9/2013 | Wilson et al. |
| 2013/0253572 A1 | 9/2013 | Molaei et al. |
| 2013/0253631 A1 | 9/2013 | Schmid et al. |
| 2013/0253634 A1 | 9/2013 | Wilson et al. |
| 2013/0261728 A1 | 10/2013 | Perkins et al. |
| 2013/0261730 A1 | 10/2013 | Bose et al. |
| 2013/0261732 A1 | 10/2013 | Perkins et al. |
| 2013/0267986 A1 | 10/2013 | Hines |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0282096 A1 | 10/2013 | Berez et al. |
| 2013/0289690 A1 | 10/2013 | Thapliyal |
| 2013/0289713 A1 | 10/2013 | Pearson et al. |
| 2013/0289714 A1 | 10/2013 | Strauss et al. |
| 2013/0302251 A1 | 11/2013 | Constant et al. |
| 2013/0304109 A1 | 11/2013 | Abrams et al. |
| 2013/0310687 A1 | 11/2013 | Takizawa et al. |
| 2013/0325053 A1 | 12/2013 | Porter et al. |
| 2013/0331883 A1 | 12/2013 | Strauss et al. |
| 2013/0338688 A1 | 12/2013 | Rehman et al. |
| 2013/0344159 A1 | 12/2013 | Moine et al. |
| 2013/0345738 A1 | 12/2013 | Eskridge |
| 2013/0345785 A1 | 12/2013 | Hartley et al. |
| 2014/0005698 A1 | 1/2014 | Eskridge |
| 2014/0012303 A1 | 1/2014 | Heipl |
| 2014/0012307 A1 | 1/2014 | Franano et al. |
| 2014/0012363 A1 | 1/2014 | Franano et al. |
| 2014/0018843 A1 | 1/2014 | Berez et al. |
| 2014/0018902 A1 | 1/2014 | Myr |
| 2014/0025151 A1 | 1/2014 | Gao |
| 2014/0025154 A1 | 1/2014 | Liang et al. |
| 2014/0031858 A1 | 1/2014 | Bhagchandani et al. |
| 2014/0031918 A1 | 1/2014 | Newell et al. |
| 2014/0031920 A1 | 1/2014 | Malek |
| 2014/0039536 A1 | 2/2014 | Cully et al. |
| 2014/0039606 A1 | 2/2014 | Rudakov et al. |
| 2014/0046338 A1 | 2/2014 | Grandfield et al. |
| 2014/0047694 A1 | 2/2014 | Monstadt et al. |
| 2014/0052168 A1 | 2/2014 | Sawhney |
| 2014/0052233 A1 | 2/2014 | Cox et al. |
| 2014/0058420 A1 | 2/2014 | Hannes et al. |
| 2014/0058436 A1 | 2/2014 | Rosenbluth et al. |

(56) References Cited

U.S. PATENT DOCUMENTS

| | | |
|---|---|---|
| 2014/0058498 A1 | 2/2014 | Hannes et al. |
| 2014/0058500 A1 | 2/2014 | Lundkvist et al. |
| 2014/0074149 A1 | 3/2014 | Garcia et al. |
| 2014/0081313 A1 | 3/2014 | Elliott |
| 2014/0081374 A1 | 3/2014 | Kim et al. |
| 2014/0082924 A1 | 3/2014 | Lundkvist et al. |
| 2014/0083969 A1 | 3/2014 | Porter |
| 2014/0088690 A1 | 3/2014 | Fogarty et al. |
| 2014/0094896 A1 | 4/2014 | Berez et al. |
| 2014/0099374 A1 | 4/2014 | Golzarian et al. |
| 2014/0100647 A1 | 4/2014 | Bourang |
| 2014/0114342 A1 | 4/2014 | Berez et al. |
| 2014/0114343 A1 | 4/2014 | Lee et al. |
| 2014/0121744 A1 | 5/2014 | Kusleika |
| 2014/0121745 A1 | 5/2014 | Kusleika et al. |
| 2014/0121746 A1 | 5/2014 | Kusleika et al. |
| 2014/0121752 A1 | 5/2014 | Losordo et al. |
| 2014/0128901 A1 | 5/2014 | Kang et al. |
| 2014/0128907 A1 | 5/2014 | Hui et al. |
| 2014/0128957 A1 | 5/2014 | Losordo et al. |
| 2014/0130965 A1 | 5/2014 | Banks et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0142611 A1 | 5/2014 | Plaza et al. |
| 2014/0163604 A1 | 6/2014 | Monstadt |
| 2014/0172001 A1 | 6/2014 | Becking et al. |
| 2014/0172067 A1 | 6/2014 | Brown et al. |
| 2014/0172071 A1 | 6/2014 | Berez et al. |
| 2014/0180377 A1 | 6/2014 | Bose et al. |
| 2014/0180387 A1 | 6/2014 | Khenansho et al. |
| 2014/0180397 A1 | 6/2014 | Gerberding et al. |
| 2014/0188208 A1 | 7/2014 | Hancock et al. |
| 2014/0194973 A1 | 7/2014 | Chobotov |
| 2014/0200607 A1 | 7/2014 | Sepetka et al. |
| 2014/0200648 A1 | 7/2014 | Newell et al. |
| 2014/0207162 A1 | 7/2014 | Tran et al. |
| 2014/0207180 A1 | 7/2014 | Ferrera |
| 2014/0214071 A1 | 7/2014 | Thomas |
| 2014/0222128 A1 | 8/2014 | Dusbabek et al. |
| 2014/0222130 A1 | 8/2014 | Kusleika |
| 2014/0236216 A1 | 8/2014 | Gerberding |
| 2014/0243951 A1 | 8/2014 | Orr |
| 2014/0249614 A1 | 9/2014 | Levi et al. |
| 2014/0249616 A1 | 9/2014 | Strauss et al. |
| 2014/0249620 A1 | 9/2014 | Carman et al. |
| 2014/0260928 A1 | 9/2014 | Janardhan et al. |
| 2014/0265096 A1 | 9/2014 | Janardhan et al. |
| 2014/0277100 A1 | 9/2014 | Kang |
| 2014/0277361 A1 | 9/2014 | Farhat et al. |
| 2014/0277370 A1 | 9/2014 | Brocker et al. |
| 2014/0277391 A1 | 9/2014 | Layman et al. |
| 2014/0288633 A1 | 9/2014 | Burke et al. |
| 2014/0296358 A1 | 10/2014 | Maitland et al. |
| 2015/0005807 A1* | 1/2015 | Lagodzki ............ A61F 2/01 606/200 |

* cited by examiner

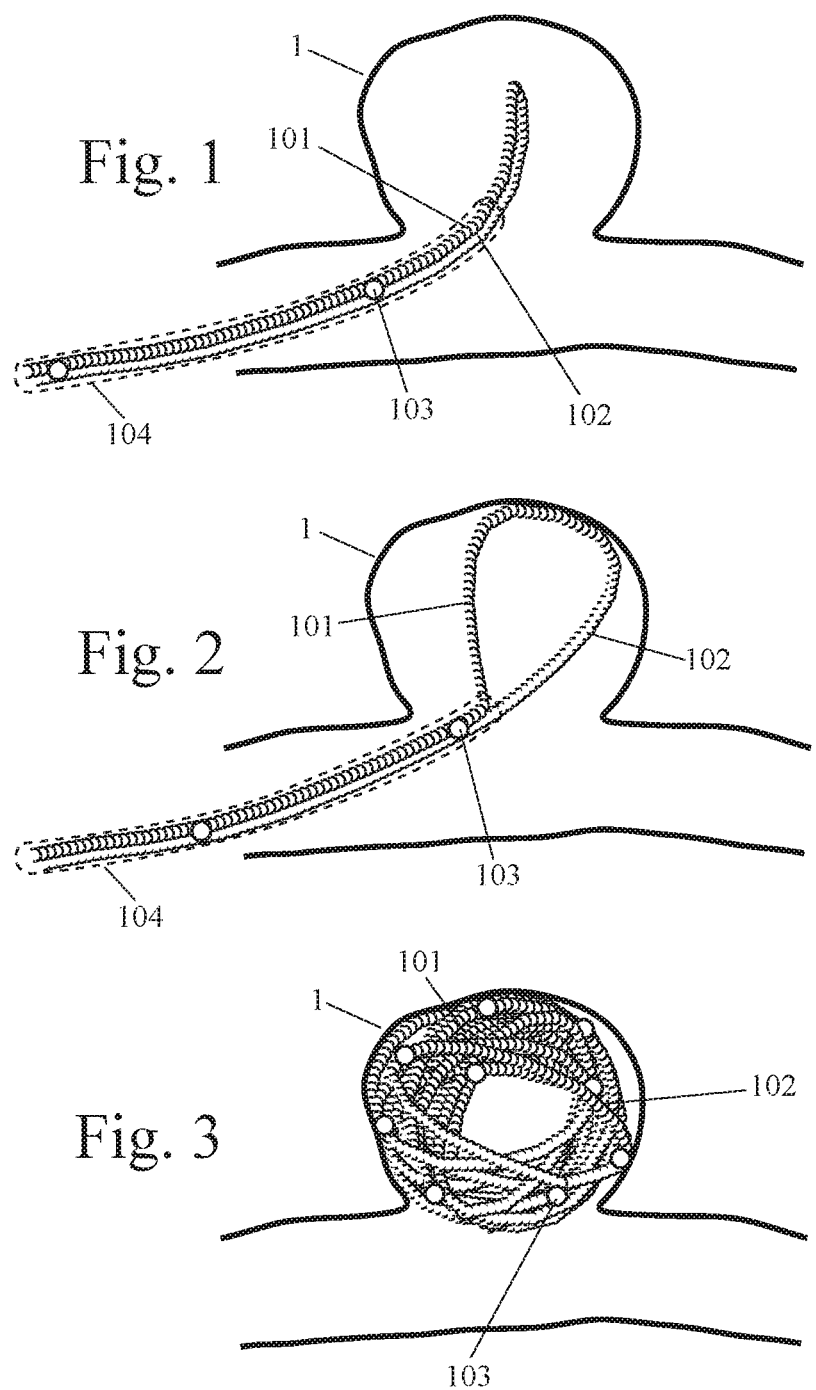

COILS WITH A SERIES OF PROXIMALLY-AND-DISTALLY-CONNECTED LOOPS FOR OCCLUDING A CEREBRAL ANEURYSM

CROSS-REFERENCE TO RELATED APPLICATIONS

This patent application is a continuation in part of U.S. patent application Ser. No. 14/526,600 entitled "Devices and Methods for Occluding a Cerebral Aneurysm" by Robert A. Connor which was filed on Oct. 29, 2014 which, in turn:

(a) is being petitioned to be a continuation in part of U.S. patent application Ser. No. 12/989,048 entitled "Aneurysm Occlusion Device" by Robert A. Connor and Muhammad Tariq Janjua which has a 371 date of Oct. 21, 2010, a filing date of Apr. 24, 2009, and a priority date of May 1, 2008 which is the U.S. national phase filing of PCT/US 2009/002537 entitled "Aneurysm Occlusion Device" by Robert A. Connor and Muhammad Tariq Janjua filed on Apr. 24, 2009 which claimed the priority benefit of U.S. Provisional Patent Application No. 61/126,047 entitled "Flow of Soft Members into a Net to Embolize an Aneurysm" by Robert A. Connor which received a filing date of May 1, 2008 and claimed the priority benefit of U.S. Provisional Patent Application No. 61/126,027 entitled "Net Filled with Soft Members to Embolize an Aneurysm" by Robert A. Connor which received a filing date of May 1, 2008; and (b) is being petitioned to claim the priority benefit of U.S. Provisional Patent Application No. 61/897,245 entitled "Devices and Methods for Occluding a Cerebral Aneurysm" by Robert A. Connor filed on Oct. 30, 2013.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for occluding a blood vessel aneurysm.

INTRODUCTION TO CEREBRAL ANEURYSMS

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain.

Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function.

CATEGORIZATION AND REVIEW OF THE PRIOR ART

It can be challenging trying to classify prior art into discrete categories. This is the certainly the case in the field of devices and methods for treating aneurysms. There are numerous examples of potentially-relevant prior art. However, classification of the prior art into categories, even if imperfect, can be an invaluable tool for reviewing the relevant prior art. Towards this end, I herein identify 38 categories of relevant prior art and provide examples of prior art in each category (including patent or patent application number, inventor, publication date, and title). Some examples of prior art disclose multiple concepts and thus appear in more than one category. This review primarily focuses on structural endovascular approaches to treating aneurysms and does not include extravascular aneurysm clips or the many different pharmaceutical coatings for aneurysm treatment devices.

The 38 categories of prior art which are used for this review are as follows: (1) stent with circumferential variation in wall porosity in parent vessel; (2) stent with longitudinal variation in wall porosity in parent vessel; (3) stent with longitudinal or cross-sectional variation in size and/or flexibility in parent vessel; (4) stent in branching parent vessel; (5) stent with helical structure in parent vessel; (6) stent with special structure or flexibility in parent vessel; (7) stent with multiple layers in parent vessel; (8) stent with non-porous walls in parent vessel; (9) stent with integrated actuators and/or sensors in parent vessel; (10) stent with other complex structure in parent vessel; (11) stent in parent vessel to contain embolics within aneurysm sac; (12) multiple stents in parent vessel; (13) temporary balloon in parent vessel; (14) multi-balloon device; (15) aneurysm neck bridge or saddle in relatively-straight parent vessel; (16) aneurysm neck bridge or saddle in parent vessel with three-way junction; (17) aneurysm neck bridge or saddle with spherical structure in parent vessel; (18) localized aneurysm neck bridge in parent vessel; (19) aneurysm neck bridge spanning aneurysm sac and parent vessel; (20) aneurysm neck bridge inside aneurysm sac with radial protrusions; (21) aneurysm neck bridge inside aneurysm sac with convex shape; (22) single-chamber woven/mesh structure in aneurysm sac; (23) multi-chamber woven/mesh structure in aneurysm sac; (24) embolic coils with relatively-traditional structures in aneurysm sac; (25) embolic coils with complex structures in aneurysm sac; (26) embolic coils with interconnecting members in aneurysm sac; (27) embolic coils with special coatings in aneurysm sac; (28) polymer or hydrogel longitudinal embolic members in aneurysm sac; (29) longitudinal embolic members with string-of-pearls structure in aneurysm sac; (30) accumulation of mass in aneurysm sac by spooling and/or axial rotation; (31) liner or balloon with non-porous walls in aneurysm sac; (32) liner, balloon, net, or mesh with porous walls in aneurysm sac; (33) liquid embolic composition into aneurysm sac; (34) gelatinous embolic composition into aneurysm sac; (35) embolic spheres and/or particles into aneurysm sac; (36) customized pre-molded member into aneurysm sac; (37) extravascular sleeve around aneurysm sac and parent vessel; and (38) other devices for aneurysm treatment.

1. Stent with Circumferential Variation in Wall Porosity in Parent Vessel:

The prior art discloses devices and methods for treating aneurysms comprising generally-cylindrical stents with circumferential variation in wall porosity which are implanted within the parent vessel of an aneurysm. In an example, a less porous portion of such a stent can comprise a "patch" which covers the aneurysm neck. In an example, a less-porous section of such a stent can be located so as to span an aneurysm neck and reduce blood flow to the aneurysm, while a more-porous section of the stent can be located so as to allow continued blood flow to a nearby (small) branching vessel. Prior art which appears to be within this category includes U.S. Pat. No. 5,951,599 (McCrory, Sep. 14, 1999, "Occlusion System for Endovascular Treatment of an Aneurysm"); U.S. Pat. No. 6,605,111 (Bose et al., Aug. 12, 2003, "Endovascular Thin Film Devices and Methods for Treating and Preventing Stroke"); U.S. Pat. No. 6,746,468 (Sepetka et al., Jun. 8, 2004, "Devices and Methods for Treating Vascular Malformations"); U.S. Pat. No. 6,969,401 (Marotta et al., Nov. 29, 2005, "Endovascular Prosthesis"); U.S. Pat. No. 7,147,659 (Jones, Dec. 12, 2006, "Expandable Stent Having a Dissolvable Portion"); U.S. Pat. No. 7,156,871 (Jones et al., Jan. 2, 2007, "Expandable Stent Having a Stabilized Portion"); U.S. Pat. No. 7,491,226 (Palmaz et al., Feb. 17, 2009, "Endoluminal Implantable Stent-Grafts"); U.S. Pat. No. 7,572,288 (Cox, Aug. 11, 2009, "Aneurysm Treatment Device and Method of Use"); U.S. Pat. No. 7,611,530 (Pomeranz et al., Nov. 3, 2009, "Expandable Stent Having Removable Slat Members"); U.S. Pat. No. 7,641,680 (Palmaz et al., Jan. 5, 2010, "Endoluminal Implantable Stent-Grafts"); and U.S. Pat. No. 7,769,603 (Jung et al., Aug. 3, 2010, "Stent Customization System and Method").

Prior art which appears to be within this category also includes U.S. Pat. No. 7,780,645 (Jones, Aug. 24, 2010, "Method of Delivering Embolic Particles to an Aneurysm"); U.S. Pat. No. 8,038,706 (Eidenschink et al., Oct. 18, 2011, "Crown Stent Assembly"); U.S. Pat. No. 8,252,040 (Cox, Aug. 28, 2012, "Aneurysm Treatment Device and Method of Use"); U.S. Pat. No. 8,267,986 (Berez et al., Sep. 18, 2012, "Vascular Stenting for Aneurysms"); U.S. Pat. No. 8,353,943 (Kuppurathanam et al., Jan. 15, 2013, "Variable Weave Graft with Metal Strand Reinforcement for In Situ Fenestration"); U.S. Pat. No. 8,382,825 (Garcia et al., Feb. 26, 2013, "Flexible Vascular Occluding Device"); U.S. Pat. No. 8,398,701 (Berez et al., Mar. 19, 2013, "Flexible Vascular Occluding Device"); U.S. Pat. No. 8,409,267 (Berez et al., Apr. 2, 2013, "Vascular Stenting for Aneurysms"); U.S. Pat. No. 8,409,269 (Berez et al., Apr. 2, 2013, "Procedures for Vascular Occlusion"); U.S. Pat. No. 8,425,548 (Connor, Apr. 23, 2013, "Occluding Member Expansion and then Stent Expansion for Aneurysm Treatment"); U.S. Pat. No. 8,430,922 (Jung et al., Apr. 30, 2013, "Stent Customization System and Method"); U.S. Pat. No. 8,470,013 (Duggal et al., Jun. 25, 2013, "Systems and Methods for Aneurysm Treatment and Vessel Occlusion"); U.S. Pat. No. 8,475,517 (Jung et al., Jul. 2, 2013, "Stent Customization System and Method"); U.S. Pat. No. 8,500,788 (Berez et al., Aug. 6, 2013, "Vascular Stenting and Other Procedures"); U.S. Pat. No. 8,529,614 (Berez et al., Sep. 10, 2013, "Vascular Stenting and Other Procedures"); U.S. Pat. No. 8,529,614 (Berez et al., Sep. 10, 2013, "Vascular Stenting and Other Procedures"); U.S. Pat. No. 8,550,344 (Jung et al., Oct. 8, 2013, "Specialty Stents with Flow Control Features or the Like"); U.S. Pat. No. 8,551,155 (Jung et al., Oct. 8, 2013, "Stent Customization System and Method"); and U.S. Pat. No. 8,556,953 (Berez et al., Oct. 15, 2013, "Vascular Stenting for Aneurysms").

Prior art which appears to be within this category also includes U.S. Pat. No. 8,562,667 (Cox, Oct. 22, 2013, "Aneurysm Treatment Device and Method of Use"); U.S. Pat. No. 8,577,693 (Jung et al., Nov. 5, 2013, "Specialty Stents with Flow Control Features or the Like"); U.S. Pat. No. 8,597,320 (Sepetka et al., Dec. 3, 2013, "Devices and Methods for Treating Vascular Malformations"); U.S. Pat. No. 8,597,342 (McKinsey et al., Dec. 3, 2013, "Textile Graft for In Situ Fenestration"); U.S. Pat. No. 8,715,312 (Burke et al., May 6, 2014, "Aneurysm Treatment Device and Method of Use"); U.S. Pat. No. 8,715,317 (Janardhan et al., May 6, 2014, "Flow Diverting Devices"); U.S. Pat. No. 8,721,706 (Jung et al., May 13, 2014, "Specialty Stents with Flow Control Features or the Like"); U.S. Pat. No. 8,747,432 (Janardhan et al., Jun. 10, 2014, "Woven Vascular Treatment Devices"); U.S. Pat. No. 8,753,371 (Janardhan et al., Jun. 17, 2014, "Woven Vascular Treatment Systems"); U.S. Pat. No. 8,784,446 (Janardhan et al., Jul. 22, 2014, "Circumferentially Offset Variable Porosity Devices"); U.S. Pat. No. 8,813,625 (Janardhan et al., Aug. 26, 2014, "Methods of Manufacturing Variable Porosity Flow Diverting Devices"); and U.S. Pat. No. 8,845,679 (Janardhan et al., Sep. 30, 2014, "Variable Porosity Flow Diverting Devices").

Prior art which appears to be within this category also includes U.S. patent applications: 20020169473 (Sepetka et al., Nov. 14, 2002, "Devices and Methods for Treating Vascular Malformations"); 20030018294 (Cox, Jan. 23, 2003, "Aneurysm Treatment Device and Method of Use"); 20030109917 (Rudin et al., Jun. 12, 2003, "Stent Vascular Intervention Device and Method"); 20030139802 (Wulfman et al., Jul. 24, 2003, "Medical Device"); 20040181253 (Sepetka et al., Sep. 16, 2004, "Devices and Methods for Treating Vascular Malformations"); 20050267568 (Berez et al., Dec. 1, 2005, "Flexible Vascular Occluding Device"); 20060206200 (Garcia et al., Sep. 14, 2006, "Flexible Vascular Occluding Device"); 20060206201 (Garcia et al., Sep. 14, 2006, "Flexible Vascular Occluding Device"); 20070021816 (Rudin, Jan. 25, 2007, "Stent Vascular Intervention Device and Methods for Treating Aneurysms"); 20070067015 (Jones et al., Mar. 22, 2007, "Expandable Stent Having a Stabilized Portion"); and 20070239261 (Bose et al., Oct. 11, 2007, "Aneurysm Occlusion System and Method").

Prior art which appears to be within this category also includes U.S. patent applications: 20080114391 (Dieck et al., May 15, 2008, "Aneurysm Covering Devices and Delivery Devices"); 20080114436 (Dieck et al., May 15, 2008, "Aneurysm Covering Devices and Delivery Devices"); 20090069880 (Vonderwalde et al., Mar. 12, 2009, "Implantable Graft Assembly and Aneurysm Treatment");

20090270974 (Berez et al., Oct. 29, 2009, "Vascular Stenting for Aneurysms"); 20090287241 (Berez et al., Nov. 19, 2009, "Methods and Apparatus for Luminal Stenting"); 20090287288 (Berez et al., Nov. 19, 2009, "Methods and Apparatus for Luminal Stenting"); 20090292348 (Berez et al., Nov. 26, 2009, "Vascular Stenting and Other Procedures"); 20090319017 (Berez et al., Dec. 24, 2009, "Vascular Stenting for Aneurysms"); 20100010624 (Berez et al., Jan. 14, 2010, "Vascular Stenting for Aneurysms"); 20100082091 (Berez et al., Apr. 1, 2010, "Vascular Stenting and Other Procedures"); and 20100106240 (Duggal et al., Apr. 29, 2010, "Systems and Methods for Aneurysm Treatment and Vessel Occlusion").

Prior art which appears to be within this category also includes U.S. patent applications: 20100274276 (Chow et al., Oct. 28, 2010, "Aneurysm Treatment System, Device and Method"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); 20110152998 (Berez et al., Jun. 23, 2011, "Procedures for Vascular Occlusion"); 20110166592 (Garcia et al., Jul. 7, 2011, "Flexible Vascular Occluding Device"); 20110224776 (Sepetka et al., Sep. 15, 2011, "Devices and Methods for Treating Vascular Malformations"); 20120004682 (Connor, Jan. 5, 2012, "Occluding Member Expansion and Then Stent Expansion for Aneurysm Treatment"); 20130123901 (Connor et al., May 16, 2013, "Stent with In Situ Determination of Wall Areas with Differences in Porosity"); 20130172975 (Berez et al., Jul. 4, 2013, "Methods and Apparatus for Luminal Stenting"); 20130204288 (Johnson et al., Aug. 8, 2013, "Modifiable Occlusion Device"); 20130204288 (Johnson et al., Aug. 8, 2013, "Modifiable Occlusion Device"); and 20130231732 (Vonderwalde et al., Sep. 5, 2013, "Implantable Graft Assembly and Aneurysm Treatment").

Prior art which appears to be within this category also includes U.S. patent applications: 20130238083 (Duggal et al., Sep. 12, 2013, "Systems and Methods for Aneurysm Treatment and Vessel Occlusion"); 20130282096 (Berez et al., Oct. 24, 2013, "Procedures for Vascular Occlusion"); 20140018843 (Berez et al., Jan. 16, 2014, "Methods and Apparatus for Luminal Stenting"); 20140039606 (Rudakov et al., Feb. 6, 2014, "Medical Device"); 20140074149 (Garcia et al., Mar. 13, 2014, "Flexible Vascular Occluding Device"); 20140094896 (Berez et al., Apr. 3, 2014, "Vascular Stenting for Aneurysms"); 20140114342 (Berez et al., Apr. 24, 2014, "Flexible Vascular Occluding Device"); 20140128901 (Kang et al., May 8, 2014, "Implant for Aneurysm Treatment"); 20140172071 (Berez et al., Jun. 19, 2014, "Vascular Stenting for Aneurysms"); 20140260928 (Janardhan et al., Sep. 18, 2014, "Methods of Using Non-Cylindrical Mandrels"); 20140265096 (Janardhan et al., Sep. 18, 2014, "Non-Cylindrical Mandrels"); and 20140288633 (Burke et al., Sep. 25, 2014, "Aneurysm Treatment Device and Method of Use"); and Yet unpublished U.S. patent application Ser. No. 13/889,451 (Connor et al., 2013, "Method of Radially-Asymmetric Stent Expansion").

2. Stent with Longitudinal Variation in Wall Porosity in Parent Vessel:

The prior art also discloses devices and methods for treating aneurysms comprising generally-cylindrical stents with longitudinal variation in wall porosity which are implanted within the parent vessel of an aneurysm. In an example, a less-porous section of such a stent can be located so as to span an aneurysm neck and reduce blood flow to the aneurysm, while a more-porous section of the stent can be located so as to allow continued blood flow to a nearby (small) branching vessel. Prior art which appears to be within this category includes U.S. Pat. No. 5,693,088 (Lazarus, Dec. 2, 1997, "Intraluminal Vascular Graft"); U.S. Pat. No. 5,769,884 (Solovay, Jun. 23, 1998, "Controlled Porosity Endovascular Implant"); U.S. Pat. No. 5,951,599 (McCrory, Sep. 14, 1999, "Occlusion System for Endovascular Treatment of an Aneurysm"); U.S. Pat. No. 6,093,199 (Brown et al., Jul. 25, 2000, "Intra-Luminal Device for Treatment of Body Cavities and Lumens and Method of Use"); U.S. Pat. No. 6,258,115 (Dubrul, Jul. 10, 2001, "Bifurcated Stent and Distal Protection System"); U.S. Pat. No. 6,312,463 (Rourke et al., Nov. 6, 2001, "Micro-Porous Mesh Stent with Hybrid Structure"); U.S. Pat. No. 6,585,758 (Chouinard et al., Jul. 1, 2003, "Multi-Section Filamentary Endoluminal Stent"); U.S. Pat. No. 6,676,701 (Rourke et al., Jan. 13, 2004, "Micro-Porous Mesh Stent with Hybrid Structure"); U.S. Pat. No. 6,746,468 (Sepetka et al., Jun. 8, 2004, "Devices and Methods for Treating Vascular Malformations"); U.S. Pat. No. 6,913,618 (Denardo et al., Jul. 5, 2005, "Intravascular Flow Modifier and Reinforcement Device"); U.S. Pat. No. 7,041,129 (Rourke et al., May 9, 2006, "Micro-Porous Mesh Stent with Hybrid Structure"); U.S. Pat. No. 7,288,112 (Denardo et al., Oct. 30, 2007, "Intravascular Flow Modifier and Reinforcement Device"); and U.S. Pat. No. 7,306,624 (Yodfat et al., Dec. 11, 2007, "Implantable Intraluminal Device and Method of Using Same in Treating Aneurysms").

Prior art which appears to be within this category also includes U.S. Pat. No. 7,491,226 (Palmaz et al., Feb. 17, 2009, "Endoluminal Implantable Stent-Grafts"); U.S. Pat. No. 7,572,290 (Yodfat et al., Aug. 11, 2009, "Implantable Intraluminal Device and Method of Using Same in Treating Aneurysms"); U.S. Pat. No. 7,641,680 (Palmaz et al., Jan. 5, 2010, "Endoluminal Implantable Stent-Grafts"); U.S. Pat. No. 7,695,509 (Rourke et al., Apr. 13, 2010, "Micro-Porous Mesh Stent with Hybrid Structure"); U.S. Pat. No. 7,763,011 (Ortiz et al., Jul. 27, 2010, "Variable Density Braid Stent"); U.S. Pat. No. 7,769,603 (Jung et al., Aug. 3, 2010, "Stent Customization System and Method"); U.S. Pat. No. 7,811,300 (Feller et al., Oct. 12, 2010, "Thin Film Devices for Temporary or Permanent Occlusion of a Vessel"); U.S. Pat. No. 7,857,843 (Henderson, Dec. 28, 2010, "Differentially Expanded Vascular Graft"); U.S. Pat. No. 7,862,608 (Hogendijk et al., Jan. 4, 2011, "Vascular Prosthesis and Methods of Use"); U.S. Pat. No. 7,942,925 (Yodfat et al., May 17, 2011, "Implantable Intraluminal Device and Method of Using Same in Treating Aneurysms"); U.S. Pat. No. 8,007,529 (Yan, Aug. 30, 2011, "Medicated Porous Metal Prosthesis"); U.S. Pat. No. 8,267,986 (Berez et al., Sep. 18, 2012, "Vascular Stenting for Aneurysms"); and U.S. Pat. No. 8,353,943 (Kuppurathanam et al., Jan. 15, 2013, "Variable Weave Graft with Metal Strand Reinforcement for In Situ Fenestration").

Prior art which appears to be within this category also includes U.S. Pat. No. 8,409,267 (Berez et al., Apr. 2, 2013, "Vascular Stenting for Aneurysms"); U.S. Pat. No. 8,409,269 (Berez et al., Apr. 2, 2013, "Procedures for Vascular Occlusion"); U.S. Pat. No. 8,419,787 (Yodfat et al., Apr. 16, 2013, "Implantable Intraluminal Device and Method of Using Same in Treating Aneurysms"); U.S. Pat. No. 8,430,922 (Jung et al., Apr. 30, 2013, "Stent Customization System and Method"); U.S. Pat. No. 8,470,013 (Duggal et al., Jun. 25, 2013, "Systems and Methods for Aneurysm Treatment and Vessel Occlusion"); U.S. Pat. No. 8,475,517 (Jung et al., Jul. 2, 2013, "Stent Customization System and Method");

U.S. Pat. No. 8,491,646 (Schreck, Jul. 23, 2013, "Stent Graft"); U.S. Pat. No. 8,500,788 (Berez et al., Aug. 6, 2013, "Vascular Stenting and Other Procedures"); U.S. Pat. No. 8,506,618 (Chouinard et al., Aug. 13, 2013, "Multi-Section Filamentary Endoluminal Stent"); U.S. Pat. No. 8,506,619 (Ortiz et al., Aug. 13, 2013, "Variable Density Braid Stent"); U.S. Pat. No. 8,529,614 (Berez et al., Sep. 10, 2013, "Vascular Stenting and Other Procedures"); U.S. Pat. No. 8,529,614 (Berez et al., Sep. 10, 2013, "Vascular Stenting and Other Procedures"); U.S. Pat. No. 8,535,590 (Milner et al., Sep. 17, 2013, "Spray System and Method of Making Phase Separated Polymer Membrane Structures"); and U.S. Pat. No. 8,550,344 (Jung et al., Oct. 8, 2013, "Specialty Stents with Flow Control Features or the Like").

Prior art which appears to be within this category also includes U.S. Pat. No. 8,551,155 (Jung et al., Oct. 8, 2013, "Stent Customization System and Method"); U.S. Pat. No. 8,556,953 (Berez et al., Oct. 15, 2013, "Vascular Stenting for Aneurysms"); U.S. Pat. No. 8,577,693 (Jung et al., Nov. 5, 2013, "Specialty Stents with Flow Control Features or the Like"); U.S. Pat. No. 8,597,320 (Sepetka et al., Dec. 3, 2013, "Devices and Methods for Treating Vascular Malformations"); U.S. Pat. No. 8,715,317 (Janardhan et al., May 6, 2014, "Flow Diverting Devices"); U.S. Pat. No. 8,721,706 (Jung et al., May 13, 2014, "Specialty Stents with Flow Control Features or the Like"); U.S. Pat. No. 8,747,432 (Janardhan et al., Jun. 10, 2014, "Woven Vascular Treatment Devices"); U.S. Pat. No. 8,753,371 (Janardhan et al., Jun. 17, 2014, "Woven Vascular Treatment Systems"); U.S. Pat. No. 8,784,446 (Janardhan et al., Jul. 22, 2014, "Circumferentially Offset Variable Porosity Devices"); U.S. Pat. No. 8,813,625 (Janardhan et al., Aug. 26, 2014, "Methods of Manufacturing Variable Porosity Flow Diverting Devices"); and U.S. Pat. No. 8,845,679 (Janardhan et al., Sep. 30, 2014, "Variable Porosity Flow Diverting Devices").

Prior art which appears to be within this category also includes U.S. patent applications: 20020169473 (Sepetka et al., Nov. 14, 2002, "Devices and Methods for Treating Vascular Malformations"); 20030074049 (Hoganson et al., Apr. 17, 2003, "Covered Stents and Systems for Deploying Covered Stents"); 20030100945 (Yodfat et al., May 29, 2003, "Implantable Intraluminal Device and Method of Using Same in Treating Aneurysms"); 20030195606 (Davidson et al., Oct. 16, 2003, "Bifurcation Stent System and Method"); 20040111142 (Rourke et al., Jun. 10, 2004, "Micro-Porous Mesh Stent with Hybrid Structure"); 20040181253 (Sepetka et al., Sep. 16, 2004, "Devices and Methods for Treating Vascular Malformations"); 20040193246 (Ferrera, Sep. 30, 2004, "Methods and Apparatus for Treating Aneurysms and Other Vascular Defects"); 20050010281 (Yodfat et al., Jan. 13, 2005, "Implantable Intraluminal Device and Method of Using Same in Treating Aneurysms"); and 20050090888 (Hines et al., Apr. 28, 2005, "Pleated Stent Assembly").

Prior art which appears to be within this category also includes U.S. patent applications: 20050283220 (Gobran et al., Dec. 22, 2005, "Blood Flow Diverters for the Treatment of Intracranial Aneurysms"); 20070032855 (Davidson et al., Feb. 8, 2007, "Extendible Stent Apparatus"); 20070060994 (Gobran et al., Mar. 15, 2007, "Blood Flow Diverters for the Treatment of Intracranial Aneurysms"); 20070150045 (Ferrera, Jun. 28, 2007, "Methods and Apparatus for Treating Aneurysms and Other Vascular Defects"); 20070219619 (Dieck et al., Sep. 20, 2007, "Partially Covered Stent Devices and Methods of Use"); 20080004653 (Sherman et al., Jan. 3, 2008, "Thin Film Devices for Occlusion of a Vessel"); 20080039933 (Yodfat et al., Feb. 14, 2008, "Implantable Intraluminal Device and Method of Using Same in Treating Aneurysms"); 20090069880 (Vonderwalde et al., Mar. 12, 2009, "Implantable Graft Assembly and Aneurysm Treatment"); 20090270970 (Yodfat et al., Oct. 29, 2009, "Implantable Intraluminal Device and Method of Using Same in Treating Aneurysms"); 20090270974 (Berez et al., Oct. 29, 2009, "Vascular Stenting for Aneurysms"); and 20090287241 (Berez et al., Nov. 19, 2009, "Methods and Apparatus for Luminal Stenting").

Prior art which appears to be within this category also includes U.S. patent applications: 20090287288 (Berez et al., Nov. 19, 2009, "Methods and Apparatus for Luminal Stenting"); 20090292348 (Berez et al., Nov. 26, 2009, "Vascular Stenting and Other Procedures"); 20090319017 (Berez et al., Dec. 24, 2009, "Vascular Stenting for Aneurysms"); 20090319023 (Hildebrand et al., Dec. 24, 2009, "Stents and Stent Grafts"); 20100010624 (Berez et al., Jan. 14, 2010, "Vascular Stenting for Aneurysms"); 20100082091 (Berez et al., Apr. 1, 2010, "Vascular Stenting and Other Procedures"); 20100106240 (Duggal et al., Apr. 29, 2010, "Systems and Methods for Aneurysm Treatment and Vessel Occlusion"); 20100152834 (Hannes et al., Jun. 17, 2010, "Implant for Influencing Blood Flow"); 20100198334 (Yodfat et al., Aug. 5, 2010, "Implantable Intraluminal Device and Method of Using Same in Treating Aneurysms"); 20100274346 (Chouinard et al., Oct. 28, 2010, "Multi-Section Filamentary Endoluminal Stent"); 20110046716 (Parkinson et al., Feb. 24, 2011, "Stent"); 20110054589 (Bashiri et al., Mar. 3, 2011, "Stent with Variable Cross Section Braiding Filament and Method for Making Same"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); and 20110152998 (Berez et al., Jun. 23, 2011, "Procedures for Vascular Occlusion").

Prior art which appears to be within this category also includes U.S. patent applications: 20110224776 (Sepetka et al., Sep. 15, 2011, "Devices and Methods for Treating Vascular Malformations"); 20120253377 (Slazas et al., Oct. 4, 2012, "Modifiable Occlusion Device"); 20120271399 (Perkins et al., Oct. 25, 2012, "High Metal to Vessel Ratio Landing Zone Stent-Graft and Method"); 20120303112 (Armstrong et al., Nov. 29, 2012, "Stent"); 20130123901 (Connor et al., May 16, 2013, "Stent with In Situ Determination of Wall Areas with Differences in Porosity"); 20130131780 (Armstrong et al., May 23, 2013, "Lattice"); 20130172975 (Berez et al., Jul. 4, 2013, "Methods and Apparatus for Luminal Stenting"); 20130190805 (Slazas et al., Jul. 25, 2013, "Method of Fabricating Modifiable Occlusion Device"); 20130197617 (Armstrong et al., Aug. 1, 2013, "Stent"); 20130197624 (Armstrong et al., Aug. 1, 2013, "Stent"); 20130204347 (Armstrong et al., Aug. 8, 2013, "Lattice"); 20130204351 (Cox et al., Aug. 8, 2013, "Aneurysm Graft Devices and Methods"); 20130211497 (Charlebois et al., Aug. 15, 2013, "Medical Prostheses Having Bundled and Non-Bundled Regions"); and 20130226276 (Newell et al., Aug. 29, 2013, "Methods and Apparatus for Luminal Stenting").

Prior art which appears to be within this category also includes U.S. patent applications: 20130226278 (Newell et al., Aug. 29, 2013, "Methods and Apparatus for Luminal Stenting"); 20130231732 (Vonderwalde et al., Sep. 5, 2013, "Implantable Graft Assembly and Aneurysm Treatment"); 20130238083 (Duggal et al., Sep. 12, 2013, "Systems and Methods for Aneurysm Treatment and Vessel Occlusion"); 20130245745 (Vong et al., Sep. 19, 2013, "Stent and Stent Delivery Device"); 20130261728 (Perkins et al., Oct. 3, 2013, "High Metal to Vessel Ratio Stent and Method"); 20130261732 (Perkins et al., Oct. 3, 2013, "Integrated Mesh High Metal to Vessel Ratio Stent and Method"); 20130282096 (Berez et al., Oct. 24, 2013, "Procedures for Vascular Occlusion"); 20140018843 (Berez et al., Jan. 16, 2014, "Methods and Apparatus for Luminal Stenting"); 20140025151 (Gao, Jan. 23, 2014, "Retrievable Stent for Intracranial Aneurysms"); 20140039606 (Rudakov et al., Feb. 6, 2014, "Medical Device"); 20140058498 (Hannes et al., Feb. 27, 2014, "Implant Comprising a Non-Woven Fabric"); 20140083969 (Porter, Mar. 27, 2014, "Method of Manufacturing a Variably Reinforced Elongate Medical Device"); and 20140094896 (Berez et al., Apr. 3, 2014, "Vascular Stenting for Aneurysms").

Prior art which appears to be within this category also includes U.S. patent applications: 20140121744 (Kusleika, May 1, 2014, "Methods and Systems for Increasing a Density of a Region of a Vascular Device"); 20140121745 (Kusleika et al., May 1, 2014, "Systems for Attaining a Predetermined Porosity of a Vascular Device"); 20140121746 (Kusleika et al., May 1, 2014, "Methods for Attaining a Predetermined Porosity of a Vascular Device"); 20140128901 (Kang et al., May 8, 2014, "Implant for Aneurysm Treatment"); 20140172071 (Berez et al., Jun. 19, 2014, "Vascular Stenting for Aneurysms"); 20140200648 (Newell et al., Jul. 17, 2014, "Methods and Apparatus for Luminal Stenting"); 20140249620 (Carman et al., Sep. 4, 2014, "Ultra-Low Fractional Area Coverage Flow Diverter for Treating Aneurysms and Vascular Diseases"); 20140260928 (Janardhan et al., Sep. 18, 2014, "Methods of Using Non-Cylindrical Mandrels"); and 20140265096 (Janardhan et al., Sep. 18, 2014, "Non-Cylindrical Mandrels").

3. Stent with Longitudinal or Cross-Sectional Variation in Size and/or Flexibility in Parent Vessel:

The prior art also discloses devices and methods for treating aneurysms comprising generally-cylindrical stents with longitudinal or cross-sectional variation in their size and/or flexibility which are implanted within the parent vessel of an aneurysm. Prior art which appears to be within this category includes U.S. Pat. No. 5,836,966 (St. Germain, Nov. 17, 1998, "Variable Expansion Force Stent"); U.S. Pat. No. 5,868,780 (Lashinski et al., Feb. 9, 1999, "Stents for Supporting Lumens in Living Tissue"); U.S. Pat. No. 5,922,019 (Hankh et al., Jul. 13, 1999, "Conical Stent"); U.S. Pat. No. 5,938,697 (Killion et al., Aug. 17, 1999, "Stent Having Variable Properties"); U.S. Pat. No. 5,957,975 (Lafont et al., Sep. 28, 1999, "Stent Having a Programmed Pattern of In Vivo Degradation"); U.S. Pat. No. 5,980,514 (Kupiecki et al., Nov. 9, 1999, "Aneurysm Closure Device Assembly"); U.S. Pat. No. 6,027,526 (Limon et al., Feb. 22, 2000, "Stent Having Varied Amounts of Structural Strength Along its Length"); U.S. Pat. No. 6,071,298 (Lashinski et al., Jun. 6, 2000, "Stents for Supporting Lumens in Living Tissue"); U.S. Pat. No. 6,096,034 (Kupiecki et al., Aug. 1, 2000, "Aneurysm Closure Device Assembly"); U.S. Pat. No. 6,099,559 (Nolting, Aug. 8, 2000, "Endoluminal Support Assembly with Capped Ends"); U.S. Pat. No. 6,159,238 (Killion et al., Dec. 12, 2000, "Stent Having Variable Properties and Method of Its Use"); U.S. Pat. No. 6,168,592 (Kupiecki et al., Jan. 2, 2001, "Aneurysm Closure Device Assembly"); U.S. Pat. No. 6,273,910 (Limon, Aug. 14, 2001, "Stent with Varying Strut Geometry"); U.S. Pat. No. 6,273,911 (Cox et al., Aug. 14, 2001, "Variable Strength Stent"); and U.S. Pat. No. 6,344,041 (Kupiecki et al., Feb. 5, 2002, "Aneurysm Closure Device Assembly").

Prior art which appears to be within this category also includes U.S. Pat. No. 6,468,302 (Cox et al., Oct. 22, 2002, "Variable Strength Stent"); U.S. Pat. No. 6,475,233 (Trozera, Nov. 5, 2002, "Stent Having Tapered Struts"); U.S. Pat. No. 6,475,236 (Roubin et al., Nov. 5, 2002, "Non-Foreshortening Intraluminal Prosthesis"); U.S. Pat. No. 6,485,509 (Killion et al., Nov. 26, 2002, "Stent Having Variable Properties and Method of its Use"); U.S. Pat. No. 6,497,722 (Von Oepen et al., Dec. 24, 2002, "Methods and Apparatus for In-Vivo Tailored Stents Indicated for Use in Tortuous Anatomy"); U.S. Pat. No. 6,511,505 (Cox et al., Jan. 28, 2003, "Variable Strength Stent"); U.S. Pat. No. 6,569,193 (Cox et al., May 27, 2003, "Tapered Self-Expanding Stent"); U.S. Pat. No. 6,585,758 (Chouinard et al., Jul. 1, 2003, "Multi-Section Filamentary Endoluminal Stent"); U.S. Pat. No. 6,602,284 (Cox et al., Aug. 5, 2003, "Variable Strength Stent"); U.S. Pat. No. 6,645,237 (Klumb et al., Nov. 11, 2003, "Expandable Coiled Endoluminal Prosthesis"); U.S. Pat. No. 6,652,576 (Stalker, Nov. 25, 2003, "Variable Stiffness Stent"); U.S. Pat. No. 6,660,032 (Klumb et al., Dec. 9, 2003, "Expandable Coil Endoluminal Prosthesis"); U.S. Pat. No. 6,669,723 (Killion et al., Dec. 30, 2003, "Stent Having Variable Properties and Method of its Use"); U.S. Pat. No. 6,746,475 (Rivelli, Jun. 8, 2004, "Stent with Variable Stiffness"); and U.S. Pat. No. 6,796,997 (Penn et al., Sep. 28, 2004, "Expandable Stent").

Prior art which appears to be within this category also includes U.S. Pat. No. 6,814,754 (Greenhalgh, Nov. 9, 2004, "Woven Tubular Graft with Regions of Varying Flexibility"); U.S. Pat. No. 6,860,899 (Rivelli, Mar. 1, 2005, "Method for Treating Neurovascular Aneurysms"); U.S. Pat. No. 6,899,730 (Rivelli, May 31, 2005, "Catheter-Stent Device"); U.S. Pat. No. 7,001,422 (Escamilla et al., Feb. 21, 2006, "Expandable Stent and Delivery System"); U.S. Pat. No. 7,060,091 (Killion et al., Jun. 13, 2006, "Stent Having Variable Properties and Method of Its Use"); U.S. Pat. No. 7,112,216 (Gregorich, Sep. 26, 2006, "Stent with Tapered Flexibility"); U.S. Pat. No. 7,226,475 (Lenz et al., Jun. 5, 2007, "Stent with Variable Properties"); U.S. Pat. No. 7,241,308 (Andreas et al., Jul. 10, 2007, "Stent Deployment Systems and Methods"); U.S. Pat. No. 7,309,351 (Escamilla et al., Dec. 18, 2007, "Expandable Stent with Markers and Stent Delivery System"); U.S. Pat. No. 7,326,236 (Andreas et al., Feb. 5, 2008, "Devices and Methods for Controlling and Indicating the Length of an Interventional Element"); U.S. Pat. No. 7,402,169 (Killion et al., Jul. 22, 2008, "Stent Having Variable Properties and Method of its Use"); U.S. Pat. No. 7,520,893 (Rivelli, Apr. 21, 2009, "Method for Treating Neurovascular Aneurysms"); U.S. Pat. No. 7,780,719 (Killion et al., Aug. 24, 2010, "Stent Having Variable Properties and Method of its Use"); U.S. Pat. No. 7,892,273 (George et al., Feb. 22, 2011, "Custom Length Stent Apparatus"); U.S. Pat. No. 7,918,881 (Andreas et al., Apr. 5, 2011, "Stent Deployment Systems and Methods"); and U.S. Pat. No. 7,935,142 (Gregorich, May 3, 2011, "Stent with Tapered Flexibility"); U.S. Pat. No. 7,959,662 (Erbel et al., Jun. 14, 2011, "Endovascular Prosthesis").

Prior art which appears to be within this category also includes U.S. Pat. No. 8,357,178 (Grandfield et al., Jan. 22, 2013, "Vascular and Bodily Duct Treatment Devices and Methods"); U.S. Pat. No. 8,357,179 (Grandfield et al., Jan. 22, 2013, "Vascular and Bodily Duct Treatment Devices and Methods"); U.S. Pat. No. 8,506,618 (Chouinard et al., Aug. 13, 2013, "Multi-Section Filamentary Endoluminal Stent"); U.S. Pat. No. 8,529,596 (Grandfield et al., Sep. 10, 2013, "Vascular and Bodily Duct Treatment Devices and Methods"); U.S. Pat. No. 8,715,317 (Janardhan et al., May 6, 2014, "Flow Diverting Devices"); U.S. Pat. No. 8,734,502 (Orr, May 27, 2014, "Tapered Stent and Flexible Prosthesis"); U.S. Pat. No. 8,747,432 (Janardhan et al., Jun. 10, 2014, "Woven Vascular Treatment Devices"); U.S. Pat. No. 8,753,371 (Janardhan et al., Jun. 17, 2014, "Woven Vascular Treatment Systems"); U.S. Pat. No. 8,771,341 (Strauss et al., Jul. 8, 2014, "Protuberant Aneurysm Bridging Device and Method of Use"); U.S. Pat. No. 8,784,446 (Janardhan et al., Jul. 22, 2014, "Circumferentially Offset Variable Porosity Devices"); U.S. Pat. No. 8,795,345 (Grandfield et al., Aug. 5, 2014, "Vascular and Bodily Duct Treatment Devices and Methods"); U.S. Pat. No. 8,808,361 (Strauss et al., Aug. 19, 2014, "Protuberant Aneurysm Bridging Device and Method of Use"); U.S. Pat. No. 8,813,625 (Janardhan et al., Aug. 26, 2014, "Methods of Manufacturing Variable Porosity Flow Diverting Devices"); and U.S. Pat. No. 8,845,679 (Janardhan et al., Sep. 30, 2014, "Variable Porosity Flow Diverting Devices").

Prior art which appears to be within this category also includes U.S. patent applications: 20030074056 (Killion et al., Apr. 17, 2003, "Stent Having Variable Properties and Method of its Use"); 20040220663 (Rivelli, J R., Nov. 4, 2004, "Stent with Variable Stiffness"); 20040243216 (Gregorich, Dec. 2, 2004, "Stent with Tapered Flexibility"); 20040249439 (Richter et al., Dec. 9, 2004, "Method and Apparatus for Stenting"); 20050149159 (Andreas et al., Jul. 7, 2005, "Devices and Methods for Controlling and Indicating the Length of an Interventional Element"); 20050149164 (Rivelli, Jul. 7, 2005, "Method for Treating Neurovascular Aneurysms"); 20080319525 (Tieu et al., Dec. 25, 2008, "Self-Expanding Prosthesis"); 20100016833 (Ogle et al., Jan. 21, 2010, "Devices for the Treatment of Vascular Aneurysm"); 20100042200 (Richter et al., Feb. 18, 2010, "Method and Apparatus for Stenting"); 20100114302 (Tzafriri et al., May 6, 2010, "Endovascular Devices with Axial Perturbations"); and 20100274346 (Chouinard et al., Oct. 28, 2010, "Multi-Section Filamentary Endoluminal Stent").

Prior art which appears to be within this category also includes U.S. patent applications: 20110009940 (Grandfield et al., Jan. 13, 2011, "Vascular and Bodily Duct Treatment Devices and Methods"); 20110009941 (Grandfield et al., Jan. 13, 2011, "Vascular and Bodily Duct Treatment Devices and Methods"); 20110009950 (Grandfield et al., Jan. 13, 2011, "Vascular and Bodily Duct Treatment Devices and Methods"); 20110184456 (Grandfield et al., Jul. 28, 2011, "Vascular and Bodily Duct Treatment Devices and Methods"); 20120209311 (Grandfield et al., Aug. 16, 2012, "Vascular and Bodily Duct Treatment Devices and Methods"); 20120215250 (Grandfield et al., Aug. 23, 2012, "Vascular and Bodily Duct Treatment Devices and Methods"); 20130066415 (Hocking, Mar. 14, 2013, "Stent"); and 20130116774 (Strauss et al., May 9, 2013, "Protuberant Aneurysm Bridging Device and Method of Use").

Prior art which appears to be within this category also includes U.S. patent applications: 20130211498 (Buckley et al., Aug. 15, 2013, "Endoprosthesis with Varying Compressibility and Methods of Use"); 20130226276 (Newell et al., Aug. 29, 2013, "Methods and Apparatus for Luminal Stenting"); 20130226278 (Newell et al., Aug. 29, 2013, "Methods and Apparatus for Luminal Stenting"); 20130289714 (Strauss et al., Oct. 31, 2013, "Protuberant Aneurysm Bridging Device and Method of Use"); 20140025154 (Liang et al., Jan. 23, 2014, "Methods and Apparatus for Luminal Stenting"); 20140031918 (Newell et al., Jan. 30, 2014, "Luminal Stenting"); 20140046338 (Grandfield et al., Feb. 13, 2014, "Vascular and Bodily Duct Treatment Devices and Methods"); 20140058436 (Rosenbluth et al., Feb. 27, 2014, "Blood Flow Disruption Devices and Methods for the Treatment of Vascular Defects"); 20140083969 (Porter, Mar. 27, 2014, "Method of Manufacturing a Variably Reinforced Elongate Medical Device"); and 20140114343 (Lee et al., Apr. 24, 2014, "Stent for the Coil Embolization of a Cerebral Aneurysm").

Prior art which appears to be within this category also includes U.S. patent applications: 20140128957 (Losordo et al., May 8, 2014, "Shaped Occluding Devices and Methods of Using the Same"); 20140200648 (Newell et al., Jul. 17, 2014, "Methods and Apparatus for Luminal Stenting"); 20140243951 (Orr, Aug. 28, 2014, "Tapered Stent and Flexible Prosthesis"); 20140249616 (Strauss et al., Sep. 4, 2014, "Protuberant Aneurysm Bridging Device Deployment Method"); 20140260928 (Janardhan et al., Sep. 18, 2014, "Methods of Using Non-Cylindrical Mandrels"); and 20140265096 (Janardhan et al., Sep. 18, 2014, "Non-Cylindrical Mandrels").

4. Stent in Branching Parent Vessel:

The prior art also discloses devices and methods for treating aneurysms comprising stents which are specifically designed for implantation within a branching parent vessel. Some of the examples in this category were originally focused on aortic aneurysms rather than cerebral aneurysms, but are included herein because of the generalizability of some of their features. Prior art which appears to be within this category includes U.S. Pat. No. 5,723,004 (Dereume et al., Mar. 3, 1998, "Expandable Supportive Endoluminal Grafts"); U.S. Pat. No. 5,948,018 (Dereume et al., Sep. 7, 1999, "Expandable Supportive Endoluminal Grafts"); U.S. Pat. No. 6,165,212 (Dereume et al., Dec. 26, 2000, "Expandable Supportive Endoluminal Grafts"); U.S. Pat. No. 6,210,429 (Vardi et al., Apr. 3, 2001, "Extendible Stent Apparatus"); U.S. Pat. No. 6,309,413 (Dereume et al., Oct. 30, 2001, "Expandable Supportive Endoluminal Grafts"); U.S. Pat. No. 6,395,018 (Castaneda, May 28, 2002, "Endovascular Graft and Process for Bridging a Defect in a Main Vessel Near One of More Branch Vessels"); U.S. Pat. No. 6,599,316 (Vardi et al., Jul. 29, 2003, "Extendible Stent Apparatus"); U.S. Pat. No. 6,835,203 (Vardi et al., Dec. 28, 2004, "Extendible Stent Apparatus"); U.S. Pat. No. 6,962,602 (Vardi et al., Nov. 8, 2005, "Method for Employing an Extendible Stent Apparatus"); U.S. Pat. No. 6,994,721 (Israel, Feb. 7, 2006, "Stent Assembly"); U.S. Pat. No. 7,306,624 (Yodfat et al., Dec. 11, 2007, "Implantable Intraluminal Device and Method of Using Same in Treating Aneurysms"); U.S. Pat. No. 7,413,573 (Hartley et al., Aug. 19, 2008, "Fenestrated Stent Grafts"); U.S. Pat. No. 7,537,609 (Davidson et al., May 26, 2009, "Extendible Stent Apparatus"); and U.S. Pat. No. 7,572,290 (Yodfat et al., Aug. 11, 2009, "Implantable Intraluminal Device and Method of Using Same in Treating Aneurysms").

Prior art which appears to be within this category also includes U.S. Pat. No. 7,645,298 (Hartley et al., Jan. 12, 2010, "Stent Graft Fenestration"); U.S. Pat. No. 7,766,955 (Vardi et al., Aug. 3, 2010, "Extendible Stent Apparatus"); U.S. Pat. No. 7,769,603 (Jung et al., Aug. 3, 2010, "Stent Customization System and Method"); U.S. Pat. No. 7,776,079 (Gumm, Aug. 17, 2010, "Conical Balloon for Deployment into Side Branch"); U.S. Pat. No. 7,850,725 (Vardi et al., Dec. 14, 2010, "Extendible Stent Apparatus"); U.S. Pat. No. 7,892,279 (Davidson et al., Feb. 22, 2011, "Extendible Stent Apparatus"); U.S. Pat. No. 7,942,925 (Yodfat et al., May 17, 2011, "Implantable Intraluminal Device and Method of Using Same in Treating Aneurysms"); U.S. Pat. No. 8,012,192 (Eidenschink et al., Sep. 6, 2011, "Multi- Stent Delivery System"); U.S. Pat. No. 8,016,878 (Meyer et al., Sep. 13, 2011, "Bifurcation Stent Pattern"); U.S. Pat. No. 8,048,140 (Purdy, Nov. 1, 2011, "Fenestrated Intraluminal Stent System"); U.S. Pat. No. 8,052,736 (Doig et al., Nov. 8, 2011, "Universal Modular Stent Graft Assembly to Accommodate Flow to Collateral Branches"); U.S. Pat. No. 8,100,960 (Bruszewski, Jan. 24, 2012, "Bloused Stent-Graft and Fenestration Method"); U.S. Pat. No. 8,172,895 (Anderson et al., May 8, 2012, "Design and Assembly of Fenestrated Stent Grafts"); U.S. Pat. No. 8,226,706 (Hartley et al., Jul. 24, 2012, "Stent Graft with Integral Side Arm"); U.S. Pat. No. 8,257,430 (Covalin et al., Sep. 4, 2012, "Interconnected Leg Extensions for an Endoluminal Prosthesis"); U.S. Pat. No. 8,257,431 (Henderson et al., Sep. 4, 2012, "Multi-Furcated ePTFE Grafts and Stent-Graft Prostheses and Methods of Making the Same"); U.S. Pat. No. 8,394,136 (Hartley et al., Mar. 12, 2013, "Stent Graft with Internal Tube"); and U.S. Pat. No. 8,419,787 (Yodfat et al., Apr. 16, 2013, "Implantable Intraluminal Device and Method of Using Same in Treating Aneurysms").

Prior art which appears to be within this category also includes U.S. Pat. No. 8,430,922 (Jung et al., Apr. 30, 2013, "Stent Customization System and Method"); U.S. Pat. No. 8,475,517 (Jung et al., Jul. 2, 2013, "Stent Customization System and Method"); U.S. Pat. No. 8,523,934 (Purdy, Sep. 3, 2013, "Fenestrated Intraluminal Stent System"); U.S. Pat. No. 8,550,344 (Jung et al., Oct. 8, 2013, "Specialty Stents with Flow Control Features or the Like"); U.S. Pat. No. 8,551,155 (Jung et al., Oct. 8, 2013, "Stent Customization System and Method"); U.S. Pat. No. 8,577,693 (Jung et al., Nov. 5, 2013, "Specialty Stents with Flow Control Features or the Like"); U.S. Pat. No. 8,657,865 (Gumm, Feb. 25, 2014, "Conical Balloon for Deployment Into Side Branch"); U.S. Pat. No. 8,715,336 (Chu et al., May 6, 2014, "Methods and Apparatus for Treatment of Aneurysms Adjacent to Branch Arteries"); U.S. Pat. No. 8,721,706 (Jung et al., May 13, 2014, "Specialty Stents with Flow Control Features or the Like"); U.S. Pat. No. 8,728,145 (Chuter et al., May 20, 2014, "Low Profile Non-Symmetrical Stents and Stent-Grafts"); U.S. Pat. No. 8,747,455 (Greenberg, Jun. 10, 2014, "Branched Stent Graft System"); U.S. Pat. No. 8,769,796 (Bourang et al., Jul. 8, 2014, "Selective Stent Crimping"); U.S. Pat. No. 8,771,342 (Vardi, Jul. 8, 2014, "Methods for Deploying Stents in Bifurcations"); U.S. Pat. No. 8,795,347 (Bourang et al., Aug. 5, 2014, "Methods and Systems for Treating a Bifurcation with Provisional Side Branch Stenting"); U.S. Pat. No. 8,808,347 (Bourang et al., Aug. 19, 2014, "Stent Alignment During Treatment of a Bifurcation"); U.S. Pat. No. 8,821,564 (Schreck et al., Sep. 2, 2014, "Stent Graft"); and U.S. Pat. No. 8,828,071 (Bourang et al., Sep. 9, 2014, "Methods and Systems for Ostial Stenting of a Bifurcation").

Prior art which appears to be within this category also includes U.S. patent applications: 20010016766 (Vardi et al., Aug. 23, 2001, "Extendible Stent Apparatus"); 20010037137 (Vardi et al., Nov. 1, 2001, "Extendible Stent Apparatus"); 20020116047 (Vardi et al., Aug. 22, 2002, "Extendible Stent Apparatus and Method for Deploying the Same"); 20020156516 (Vardi et al., Oct. 24, 2002, "Method for Employing an Extendible Stent Apparatus"); 20030074049 (Hoganson et al., Apr. 17, 2003, "Covered Stents and Systems for Deploying Covered Stents"); 20030100945 (Yodfat et al., May 29, 2003, "Implantable Intraluminal Device and Method of Using Same in Treating Aneurysms"); 20030195606 (Davidson et al., Oct. 16, 2003, "Bifurcation Stent System and Method"); 20040015227 (Vardi et al., Jan. 22, 2004, "Extendible Stent Apparatus"); 20050010281 (Yodfat et al., Jan. 13, 2005, "Implantable Intraluminal Device and Method of Using Same in Treating Aneurysms"); and 20050131518 (Hartley et al., Jun. 16, 2005, "Fenestrated Stent Grafts").

Prior art which appears to be within this category also includes U.S. patent applications: 20060085061 (Vardi et al., Apr. 20, 2006, "Extendible Stent Apparatus and Method for Deploying the Same"); 20060241740 (Vardi et al., Oct. 26, 2006, "Extendible Stent Apparatus"); 20070032855 (Davidson et al., Feb. 8, 2007, "Extendible Stent Apparatus"); 20070100301 (Gumm, May 3, 2007, "Conical Balloon for Deployment into Side Branch"); 20070299498 (Perez et al., Dec. 27, 2007, "Methods and Devices for Aiding In Situ Assembly of Repair Devices"); 20080039933 (Yodfat et al., Feb. 14, 2008, "Implantable Intraluminal Device and Method of Using Same in Treating Aneurysms"); 20080312732 (Hartley et al., Dec. 18, 2008, "Fenestrated Stent Grafts"); 20090132028 (Vardi et al., May 21, 2009, "Extendible Stent Apparatus and Method for Deploying the Same"); 20090248135 (Bruszewski et al., Oct. 1, 2009, "Eversible Branch Stent-Graft and Deployment Method"); 20090270970 (Yodfat et al., Oct. 29, 2009, "Implantable Intraluminal Device and Method of Using Same in Treating Aneurysms"); and 20100198334 (Yodfat et al., Aug. 5, 2010, "Implantable Intraluminal Device and Method of Using Same in Treating Aneurysms").

Prior art which appears to be within this category also includes U.S. patent applications: 20100305681 (Gumm, Dec. 2, 2010, "Conical Balloon for Deployment into Side Branch"); 20100312326 (Chuter et al., Dec. 9, 2010, "Apparatus and Methods for Deployment of a Modular Stent-Graft System"); 20110082533 (Vardi et al., Apr. 7, 2011, "Extendible Stent Apparatus"); 20110288627 (Hartley et al., Nov. 24, 2011, "Stent Graft with Integral Side Arm"); 20110307044 (Bourang et al., Dec. 15, 2011, "Methods and Systems for Ostial Stenting of a Bifurcation"); 20110307045 (Bourang et al., Dec. 15, 2011, "Methods and Systems for Treating a Bifurcation with Provisional Side Branch Stenting"); 20110307046 (Bourang et al., Dec. 15, 2011, "Selective Stent Crimping"); 20110307052 (Bourang et al., Dec. 15, 2011, "Stent Alignment During Treatment of a Bifurcation"); 20110313512 (Hartley et al., Dec. 22, 2011, "Side Branch Stent Graft"); 20120053670 (Purdy, Mar. 1, 2012, "Fenestrated Intraluminal Stent System"); and 20120130479 (Chuter et al., May 24, 2012, "Low Profile Non-Symmetrical Stents and Stent-Grafts").

Prior art which appears to be within this category also includes U.S. patent applications: 20120143237 (Cam et al., Jun. 7, 2012, "Vascular Remodeling Device"); 20120143317 (Cam et al., Jun. 7, 2012, "Vascular Remodeling Device"); 20120253448 (Hartley et al., Oct. 4, 2012, "Stent Graft with Integral Side Arm"); 20120296361 (Cam et al., Nov. 22, 2012, "Vascular Remodeling Device"); 20120296362 (Cam et al., Nov. 22, 2012, "Vascular Remodeling Device"); 20130046371 (Greenberg et al., Feb. 21, 2013, "Endoluminal Prosthesis Having Multiple Branches or Fenestrations and Methods of Deployment"); 20130053944 (Fogarty et al., Mar. 7, 2013, "Endoluminal Prosthesis Assembly"); 20130150946 (Hartley et al., Jun. 13, 2013, "Fenestrated Stent Grafts"); 20130204351 (Cox et al., Aug. 8, 2013, "Aneurysm Graft Devices and Methods"); 20130204354 (Adams, O., Aug. 8, 2013, "Branched Stent/Graft and Method of Fabrication"); and 20130211505 (Robison, Aug. 15, 2013, "Devices and Methods for Approximating the Cross-Sectional Profile of Vasculature Having Branches").

Prior art which appears to be within this category also includes U.S. patent applications: 20130211507 (LaDuca et al., Aug. 15, 2013, "Apparatus and Method for Deploying an Implantable Device Within the Body"); 20130345785 (Hartley et al., Dec. 26, 2013, "Fenestrated Stent Grafts"); 20140100647 (Bourang, Apr. 10, 2014, "System and Methods for Treating a Bifurcation with a Fully Crimped Stent"); and 20140222130 (Kusleika, S., Aug. 7, 2014, "Vascular Device for Aneurysm Treatment and Providing Blood Flow into a Perforator Vessel").

5. Stent with Helical Structure in Parent Vessel:

The prior art also discloses devices and methods for treating aneurysms comprising stents with one or more helical structures which are implanted within the parent vessel of an aneurysm. Prior art which appears to be within this category includes U.S. Pat. No. 5,980,514 (Kupiecki et al., Nov. 9, 1999, "Aneurysm Closure Device Assembly"); U.S. Pat. No. 6,063,111 (Hieshima et al., May 16, 2000, "Stent Aneurysm Treatment System and Method"); U.S. Pat. No. 6,096,034 (Kupiecki et al., Aug. 1, 2000, "Aneurysm Closure Device Assembly"); U.S. Pat. No. 6,168,592 (Kupiecki et al., Jan. 2, 2001, "Aneurysm Closure Device Assembly"); U.S. Pat. No. 6,344,041 (Kupiecki et al., Feb. 5, 2002, "Aneurysm Closure Device Assembly"); U.S. Pat. No. 6,645,237 (Klumb et al., Nov. 11, 2003, "Expandable Coiled Endoluminal Prosthesis"); U.S. Pat. No. 6,660,032 (Klumb et al., Dec. 9, 2003, "Expandable Coil Endoluminal Prosthesis"); U.S. Pat. No. 6,746,468 (Sepetka et al., Jun. 8, 2004, "Devices and Methods for Treating Vascular Malformations"); U.S. Pat. No. 6,746,475 (Rivelli, Jun. 8, 2004, "Stent with Variable Stiffness"); U.S. Pat. No. 6,860,899 (Rivelli, Mar. 1, 2005, "Method for Treating Neurovascular Aneurysms"); U.S. Pat. No. 6,899,730 (Rivelli, May 31, 2005, "Catheter-Stent Device"); U.S. Pat. No. 7,481,821 (Fogarty et al., Jan. 27, 2009, "Embolization Device and a Method of Using the Same"); and U.S. Pat. No. 7,520,893 (Rivelli, Apr. 21, 2009, "Method for Treating Neurovascular Aneurysms").

Prior art which appears to be within this category also includes U.S. Pat. No. 7,572,288 (Cox, Aug. 11, 2009, "Aneurysm Treatment Device and Method of Use"); U.S. Pat. No. 7,803,180 (Burpee et al., Sep. 28, 2010, "Flexible Stent"); U.S. Pat. No. 7,862,608 (Hogendijk et al., Jan. 4, 2011, "Vascular Prosthesis and Methods of Use"); U.S. Pat. No. 8,057,495 (Pal et al., Nov. 15, 2011, "Aneurysm Occlusion Device"); U.S. Pat. No. 8,252,040 (Cox, Aug. 28, 2012, "Aneurysm Treatment Device and Method of Use"); U.S. Pat. No. 8,262,686 (Fogarty et al., Sep. 11, 2012, "Embolization Device and a Method of Using the Same"); U.S. Pat. No. 8,562,636 (Fogarty et al., Oct. 22, 2013, "Embolization Device and a Method of Using the Same"); U.S. Pat. No. 8,562,667 (Cox, Oct. 22, 2013, "Aneurysm Treatment Device and Method of Use"); U.S. Pat. No. 8,597,320 (Sepetka et al., Dec. 3, 2013, "Devices and Methods for Treating Vascular Malformations"); and U.S. Pat. No. 8,715,312 (Burke et al., May 6, 2014, "Aneurysm Treatment Device and Method of Use").

Prior art which appears to be within this category also includes U.S. patent applications: 20020133190 (Horton et al., Sep. 19, 2002, "In Situ Formable and Self-Forming Intravascular Flow Modifier (IFM), Catheter and IFM Assembly, and Method for Deployment of Same"); 20020169473 (Sepetka et al., Nov. 14, 2002, "Devices and Methods for Treating Vascular Malformations"); 20030018294 (Cox, Jan. 23, 2003, "Aneurysm Treatment Device and Method of Use"); 20040181253 (Sepetka et al., Sep. 16, 2004, "Devices and Methods for Treating Vascular Malformations"); 20040193246 (Ferrera, Sep. 30, 2004, "Methods and Apparatus for Treating Aneurysms and Other Vascular Defects"); 20040210249 (Fogarty et al., Oct. 21, 2004, "Embolization Device and a Method of Using the Same"); and 20040220663 (Rivelli, J R., Nov. 4, 2004, "Stent with Variable Stiffness").

Prior art which appears to be within this category also includes U.S. patent applications: 20040260384 (Allen, Dec. 23, 2004, "Superelastic Coiled Stent"); 20050015110 (Fogarty et al., Jan. 20, 2005, "Embolization Device and a Method of Using the Same"); 20050149164 (Rivelli, Jul. 7, 2005, "Method for Treating Neurovascular Aneurysms"); 20050171597 (Boatman et al., Aug. 4, 2005, "Helical Stent for Branched Vessel Prosthesis"); 20060136033 (Hermann et al., Jun. 22, 2006, "Coiled Stent Delivery System and Method"); 20070083257 (Pal et al., Apr. 12, 2007, "Aneurysm Occlusion Device"); 20070129786 (Beach et al., Jun. 7, 2007, "Helical Stent"); 20070150045 (Ferrera, Jun. 28, 2007, "Methods and Apparatus for Treating Aneurysms and Other Vascular Defects"); 20080114391 (Dieck et al., May 15, 2008, "Aneurysm Covering Devices and Delivery Devices"); 20080114436 (Dieck et al., May 15, 2008, "Aneurysm Covering Devices and Delivery Devices"); 20090105748 (Fogarty et al., Apr. 23, 2009, "Embolization Device and a Method of Using the Same"); 20110082491 (Sepetka et al., Apr. 7, 2011, "Devices and Methods for Treating Vascular Malformations"); and 20110137332 (Sepetka et al., Jun. 9, 2011, "Devices and Methods for Treating Vascular Malformations").

Prior art which appears to be within this category also includes U.S. patent applications: 20110166641 (Bales et al., Jul. 7, 2011, "Highly Flexible Stent and Method of Manufacture"); 20110224776 (Sepetka et al., Sep. 15, 2011, "Devices and Methods for Treating Vascular Malformations"); 20120179192 (Fogarty et al., Jul. 12, 2012, "Embolization Device and a Method of Using the Same"); 20120303108 (Fogarty et al., Nov. 29, 2012, "Embolization Device and a Method of Using the Same"); 20120330402 (Vad et al., Dec. 27, 2012, "Helical Stent"); 20130090719 (Bales et al., Apr. 11, 2013, "Highly Flexible Stent and Method of Manufacture"); 20130090721 (Bales et al., Apr. 11, 2013, "Highly Flexible Stent and Method of Manufacture"); 20130116659 (Porter, May 9, 2013, "Medical Device with Bi-Component Polymer Fiber Sleeve"); 20130123899 (Leopold et al., May 16, 2013, "Vascular Prosthesis and Methods of Use"); 20140031920 (Malek, Jan. 30, 2014, "Endovascular Stent"); 20140088690 (Fogarty et al., Mar. 27, 2014, "Embolization Device and a Method of Using the Same"); and 20140288633 (Burke et al., Sep. 25, 2014, "Aneurysm Treatment Device and Method of Use").

6. Stent with Special Structure or Flexibility in Parent Vessel:

The prior art also discloses devices and methods for treating aneurysms comprising stents with special structure or flexibility (which is not specified in one of the other categories herein) which are implanted within the parent vessel of an aneurysm. Prior art which appears to be within this category includes U.S. Pat. No. 5,411,549 (Peters, May 2, 1995, "Selectively Expandable, Retractable and Removable Stent"); U.S. Pat. No. 5,603,722 (Phan et al., Feb. 18, 1997, "Intravascular Stent"); U.S. Pat. No. 5,964,797 (Ho, Oct. 12, 1999, "Electrolytically Deployable Braided Vaso-Occlusion Device"); U.S. Pat. No. 6,190,406 (Duerig et al., Feb. 20, 2001, "Intravascular Stent Having Tapered Struts"); U.S. Pat. No. 6,258,117 (Camrud et al., Jul. 10, 2001, "Multi-Section Stent"); U.S. Pat. No. 6,342,068 (Thompson, Jan. 29, 2002, "Three-Dimensional Braided Stent"); U.S. Pat. No. 6,416,543 (Hilaire et al., Jul. 9, 2002, "Expandable Stent with Variable Thickness"); U.S. Pat. No. 6,485,510

(Camrud et al., Nov. 26, 2002, "Multi-Section Stent"); U.S. Pat. No. 6,520,985 (Burpee et al., Feb. 18, 2003, "Stent with Reduced Shortening"); U.S. Pat. No. 6,520,987 (Plante, Feb. 18, 2003, "Expandable Intravascular Stent"); U.S. Pat. No. 6,585,753 (Eder et al., Jul. 1, 2003, "Expandable Coil Stent"); U.S. Pat. No. 6,833,003 (Jones et al., Dec. 21, 2004, "Expandable Stent and Delivery System"); U.S. Pat. No. 7,033,385 (Eder et al., Apr. 25, 2006, "Expandable Coil Stent"); U.S. Pat. No. 7,037,330 (Rivelli et al., May 2, 2006, "Neurovascular Stent and Method"); U.S. Pat. No. 7,052,513 (Thompson, May 30, 2006, "Three-Dimensional Braided Covered Stent"); U.S. Pat. No. 7,195,648 (Jones et al., Mar. 27, 2007, "Intravascular Stent Device"); and U.S. Pat. No. 7,211,109 (Thompson, May 1, 2007, "Braided Composite Prosthesis").

Prior art which appears to be within this category also includes U.S. Pat. No. 7,309,352 (Eder et al., Dec. 18, 2007, "Expandable Coil Stent"); U.S. Pat. No. 7,491,229 (Eder et al., Feb. 17, 2009, "Expandable Coil Stent"); U.S. Pat. No. 7,695,507 (Rivelli et al., Apr. 13, 2010, "Neurovascular Stent and Method"); U.S. Pat. No. 7,803,179 (Denison, Sep. 28, 2010, "Intravascular Stents"); U.S. Pat. No. 7,955,382 (Flanagan et al., Jun. 7, 2011, "Endoprosthesis with Adjustable Surface Features"); U.S. Pat. No. 7,988,721 (Morris et al., Aug. 2, 2011, "Axially-Radially Nested Expandable Device"); U.S. Pat. No. 8,012,197 (Bashiri et al., Sep. 6, 2011, "Hybrid Balloon Expandable/Self-Expanding Stent"); U.S. Pat. No. 8,016,876 (Gregorich et al., Sep. 13, 2011, "Stent Configurations"); U.S. Pat. No. 8,070,792 (Gregorich et al., Dec. 6, 2011, "Stent"); U.S. Pat. No. 8,282,679 (Denison, Oct. 9, 2012, "Intravascular Stents"); U.S. Pat. No. 8,414,637 (Chouinard, Apr. 9, 2013, "Stent"); U.S. Pat. No. 8,512,395 (Meyer et al., Aug. 20, 2013, "Stent with Horseshoe Shaped Bridges"); U.S. Pat. No. 8,529,616 (Boyle et al., Sep. 10, 2013, "Implantable Expandable Medical Devices Having Regions of Differential Mechanical Properties and Methods of Making Same"); U.S. Pat. No. 8,623,071 (Lundkvist et al., Jan. 7, 2014, "Radiopaque Super-Elastic Intravascular Stent"); U.S. Pat. No. 8,663,309 (Chobotov, Mar. 4, 2014, "Asymmetric Stent Apparatus and Method"); U.S. Pat. No. 8,671,815 (Hancock et al., Mar. 18, 2014, "Self-Expanding Pseudo-Braided Intravascular Device"); U.S. Pat. No. 8,671,815 (Hancock et al., Mar. 18, 2014, "Self-Expanding Pseudo-Braided Intravascular Device"); U.S. Pat. No. 8,728,146 (Gregorich et al., May 20, 2014, "Stent Configurations"); U.S. Pat. No. 8,740,966 (Brocker et al., Jun. 3, 2014, "Low Profile Non-Symmetrical Stent"); and U.S. Pat. No. 8,801,772 (Shobayashi et al., Aug. 12, 2014, "Stent to Be Used in Tubular Organ In Vivo").

Prior art which appears to be within this category also includes U.S. patent applications: 20040186551 (Kao et al., Sep. 23, 2004, "Multiple Independent Nested Stent Structures and Methods for Their Preparation and Deployment"); 20060224230 (Rivelli et al., Oct. 5, 2006, "Neurovascular Stent and Method"); 20090082846 (Chobotov, Mar. 26, 2009, "Asymmetric Stent Apparatus and Method"); 20090171437 (Brocker et al., Jul. 2, 2009, "Low Profile Non-Symmetrical Stent"); 20090177268 (Lundkvist et al., Jul. 9, 2009, "Radiopaque Super-Elastic Intravascular Stent"); 20090299390 (Dehnad, Dec. 3, 2009, "Multistrand Coil for Interventional Therapy"); 20100004726 (Hancock et al., Jan. 7, 2010, "Self-Expanding Pseudo-Braided Intravascular Device"); 20100152837 (Lundkvist et al., Jun. 17, 2010, "Radiopaque Super-Elastic Intravascular Stent"); 20100222864 (Rivelli et al., Sep. 2, 2010, "Neurovascular Stent and Method"); 20100324660 (Denison, Dec. 23, 2010, "Intravascular Stents"); and 20110264192 (Hartley et al., Oct. 27, 2011, "Curve Forming Stent Graft").

Prior art which appears to be within this category also includes U.S. patent applications: 20120004719 (Gregorich et al., Jan. 5, 2012, "Stent Configurations"); 20120016462 (Gregorich et al., Jan. 19, 2012, "Stent"); 20120041540 (Shobayashi, Feb. 16, 2012, "Stent to be Used in Tubular Organ In Vivo"); 20120055614 (Hancock et al., Mar. 8, 2012, "Self-Expanding Pseudo-Braided Intravascular Device"); 20120165920 (Meyer et al., Jun. 28, 2012, "Stent"); 20120172972 (Meyer et al., Jul. 5, 2012, "Multi Stage Opening Stent Designs"); 20120323309 (Cattaneo, Dec. 20, 2012, "Stent with Flaps"); 20130060322 (Leynov et al., Mar. 7, 2013, "Expandable Framework with Overlapping Connectors"); 20130066413 (Jin et al., Mar. 14, 2013, "Surgical Apparatus for Aneurysms"); 20130146173 (Krivoruchko et al., Jun. 13, 2013, "Stent With Improved Flexibility and Method for Making Same"); 20140058500 (Lundkvist et al., Feb. 27, 2014, "Radiopaque Super-Elastic Intravascular Stent"); 20140082924 (Lundkvist et al., Mar. 27, 2014, "Radiopaque Super-Elastic Intravascular Stent"); 20140188208 (Hancock et al., Jul. 3, 2014, "Self-Expanding Pseudo-Braided Intravascular Device"); and 20140277370 (Brocker et al., Sep. 18, 2014, "Low Profile Non-Symmetrical Stent").

7. Stent with Multiple Layers in Parent Vessel:

The prior art also discloses devices and methods for treating aneurysms comprising stents with multiple layers which are implanted within the parent vessel of an aneurysm. In an example, a first layer of such a stent can be porous, but provide structural support, while a second layer can be non-porous. In another example, embolic members or compositions can be inserted between two stent layers. Prior art which appears to be within this category includes U.S. Pat. No. 5,645,559 (Hachtman et al., Jul. 8, 1997, "Multiple Layer Stent"); U.S. Pat. No. 5,769,882 (Fogarty et al., Jun. 23, 1998, "Methods and apparatus for conformably sealing prostheses within body lumens"); U.S. Pat. No. 6,086,610 (Duerig et al., Jul. 11, 2000, "Composite Self Expanding Stent Device Having a Restraining Element"); U.S. Pat. No. 6,149,681 (Houser et al., Nov. 21, 2000, "Radially Expanding Prostheses and Systems for Their Deployment"); U.S. Pat. No. 6,270,523 (Herweck et al., Aug. 7, 2001, "Expandable Shielded Vessel Support"); U.S. Pat. No. 6,331,191 (Chobotov, Dec. 18, 2001, "Layered endovascular graft"); U.S. Pat. No. 6,398,803 (Layne et al., Jun. 4, 2002, "Partial Encapsulation of Stents"); U.S. Pat. No. 6,558,414 (Layne, May 6, 2003, "Partial Encapsulation of Stents Using Strips and Bands"); U.S. Pat. No. 6,579,314 (Lombardi et al., Jun. 17, 2003, "Covered Stent with Encapsulated Ends"); U.S. Pat. No. 6,656,214 (Fogarty et al., Dec. 2, 2003, "Methods and apparatus for conformably sealing prostheses within body lumens"); U.S. Pat. No. 6,673,103 (Golds et al., Jan. 6, 2004, "Mesh and Stent for Increased Flexibility"); U.S. Pat. No. 6,699,277 (Freidberg et al., Mar. 2, 2004, "Stent with Cover Connectors"); U.S. Pat. No. 6,719,783 (Lentz et al., Apr. 13, 2004, "PTFE Vascular Graft and Method of Manufacture"); U.S. Pat. No. 6,770,087 (Layne et al., Aug. 3, 2004, "Partial Encapsulation of Stents"); U.S. Pat. No. 6,786,920 (Shannon et al., Sep. 7, 2004, "Stented Radially Expandable Tubular PTFE Grafts"); and U.S. Pat. No. 6,790,225 (Shannon et al., Sep. 14, 2004, "Stented Radially Expandable Tubular PTFE Grafts").

Prior art which appears to be within this category also includes U.S. Pat. No. 6,929,658 (Freidberg et al., Aug. 16, 2005, "Stent with Cover Connectors"); U.S. Pat. No. 7,081,129 (Chobotov, Jul. 25, 2006, "Endovascular Graft"); U.S.

Pat. No. 7,083,640 (Lombardi et al., Aug. 1, 2006, "Covered Stent with Encapsulated Ends"); U.S. Pat. No. 7,186,263 (Golds et al., Mar. 6, 2007, "Mesh Graft and Stent for Increased Flexibility"); U.S. Pat. No. 7,588,597 (Frid, Sep. 15, 2009, "Three-Dimensional Braided Structure Stent"); U.S. Pat. No. 7,615,071 (Chobotov, Nov. 10, 2009, "Endovascular Graft"); U.S. Pat. No. 7,666,220 (Evans et al., Feb. 23, 2010, "System and Methods for Endovascular Aneurysm Treatment"); U.S. Pat. No. 7,704,274 (Boyle et al., Apr. 27, 2010, "Implantable Graft and Methods of Making Same"); U.S. Pat. No. 7,758,892 (Chen et al., Jul. 20, 2010, "Medical Devices Having Multiple Layers"); U.S. Pat. No. 7,914,639 (Layne et al., Mar. 29, 2011, "Partial Encapsulation of Stents"); U.S. Pat. No. 8,211,160 (Garrison et al., Jul. 3, 2012, "Stent Graft Assembly and Method"); U.S. Pat. No. 8,388,677 (Herrmann, Mar. 5, 2013, "Anti-Thrombogenic and Anti-Restenotic Vascular Medical Devices"); U.S. Pat. No. 8,535,367 (Kim et al., Sep. 17, 2013, "Devices and Methods for Treatment of Vascular Aneurysms"); U.S. Pat. No. 8,647,377 (Kim et al., Feb. 11, 2014, "Devices and Methods for Treatment of Vascular Aneurysms"); and U.S. Pat. No. 8,784,477 (Bregulla et al., Jul. 22, 2014, "Stent Graft with Two Layer ePTFE Layer System with High Plasticity and High Rigidity").

Prior art which appears to be within this category also includes U.S. patent applications: 20030074049 (Hoganson et al., Apr. 17, 2003, "Covered Stents and Systems for Deploying Covered Stents"); 20050107863 (Brown, May 19, 2005, "Micro Structure Stent Configurations"); 20060229714 (Lombardi et al., Oct. 12, 2006, "Covered Stent with Encapsulated Ends"); 20060292206 (Kim et al., Dec. 28, 2006, "Devices and Methods for Treatment of Vascular Aneurysms"); 20070050008 (Kim et al., Mar. 1, 2007, "Devices and Methods for Treatment of Vascular Aneurysms"); 20070055355 (Kim et al., Mar. 8, 2007, "Devices and Methods for Treatment of Vascular Aneurysms"); 20070061005 (Kim et al., Mar. 15, 2007, "Devices and Methods for Treatment of Vascular Aneurysms"); and 20070207186 (Scanlon et al., Sep. 6, 2007, "Tear and Abrasion Resistant Expanded Material and Reinforcement").

Prior art which appears to be within this category also includes U.S. patent applications: 20080125852 (Garrison et al., May 29, 2008, "Stent Graft Assembly and Method"); 20090318949 (Ganpath et al., Dec. 24, 2009, "Sealing Apparatus and Methods of Use"); 20100131002 (Connor et al., May 27, 2010, "Stent with a Net Layer to Embolize an Aneurysm"); 20100179645 (Chen et al., Jul. 15, 2010, "Medical Devices Having Multiple Layers"); 20100280452 (Chen et al., Nov. 4, 2010, "Medical Devices Having Multiple Layers"); 20120172977 (Bregulla et al., Jul. 5, 2012, "Stent Graft with Two Layer ePTFE Layer System with High Plasticity and High Rigidity"); 20120259404 (Tieu et al., Oct. 11, 2012, "Stent"); 20120303112 (Armstrong et al., Nov. 29, 2012, "Stent"); 20120330343 (Kim et al., Dec. 27, 2012, "Devices and Methods for Treatment of Vascular Aneurysms"); 20130018220 (Vad et al., Jan. 17, 2013, "Method for Electrospinning a Graft Layer"); 20130103135 (Vinluan, Apr. 25, 2013, "Fenestrated Inflatable Graft"); and 20130131780 (Armstrong et al., May 23, 2013, "Lattice").

Prior art which appears to be within this category also includes U.S. patent applications: 20130131786 (Chobotov, May 23, 2013, "Endovascular Graft"); 20130197617 (Armstrong et al., Aug. 1, 2013, "Stent"); 20130197624 (Armstrong et al., Aug. 1, 2013, "Stent"); 20130204347 (Armstrong et al., Aug. 8, 2013, "Lattice"); 20130245745 (Vong et al., Sep. 19, 2013, "Stent and Stent Delivery Device"); 20140058436 (Rosenbluth et al., Feb. 27, 2014, "Blood Flow Disruption Devices and Methods for the Treatment of Vascular Defects"); 20140081374 (Kim et al., Mar. 20, 2014, "Devices and Methods for Treatment of Vascular Aneurysms"); 20140130965 (Banks et al., May 15, 2014, "Method of Manufacturing a Stent-Graft Prosthesis with Two Layers of Expanded Polytetrafluoroethylene"); and 20140180397 (Gerberding et al., Jun. 26, 2014, "Multilayer Stent").

8. Stent with Non-Porous Walls in Parent Vessel:

The prior art also discloses devices and methods for treating aneurysms comprising stents with non-porous walls which are implanted within the parent vessel of an aneurysm. Prior art which appears to be within this category includes U.S. Pat. No. 5,405,379 (Lane, Apr. 11, 1995, "Self Expanding Vascular Endoprosthesis for Aneurysms"); U.S. Pat. No. 5,723,004 (Dereume et al., Mar. 3, 1998, "Expandable Supportive Endoluminal Grafts"); U.S. Pat. No. 5,948,018 (Dereume et al., Sep. 7, 1999, "Expandable Supportive Endoluminal Grafts"); U.S. Pat. No. 6,165,212 (Dereume et al., Dec. 26, 2000, "Expandable Supportive Endoluminal Grafts"); U.S. Pat. No. 6,309,413 (Dereume et al., Oct. 30, 2001, "Expandable Supportive Endoluminal Grafts"); U.S. Pat. No. 8,003,180 (Goffena et al., Aug. 23, 2011, "Thin-Wall Polytetrafluoroethylene Tube"); U.S. Pat. No. 8,480,727 (Clarke, Jul. 9, 2013, "Endovascular Implant Having an Integral Graft Component and Method of Manufacture"); and U.S. Pat. No. 8,715,336 (Chu et al., May 6, 2014, "Methods and Apparatus for Treatment of Aneurysms Adjacent to Branch Arteries").

Prior art which appears to be within this category also includes U.S. patent applications: 20050131516 (Greenhalgh, Jun. 16, 2005, "Integral Support Stent Graft Assembly"); 20050171597 (Boatman et al., Aug. 4, 2005, "Helical Stent for Branched Vessel Prosthesis"); 20080195137 (Alleyne et al., Aug. 14, 2008, "Devices and Methods for Aneurysm Treatment"); 20130053872 (Hansen, Feb. 28, 2013, "Device and Method for Preventing Blood Flow into an Aneurysm"); 20130116659 (Porter, May 9, 2013, "Medical Device with Bi-Component Polymer Fiber Sleeve"); 20130289713 (Pearson et al., Oct. 31, 2013, "Circumferentially Constraining Sutures for a Stent-Graft"); 20140130965 (Banks et al., May 15, 2014, "Method of Manufacturing a Stent-Graft Prosthesis with Two Layers of Expanded Polytetrafluoroethylene"); and 20140194973 (Chobotov, Jul. 10, 2014, "Sac Liner for Aneurysm Repair").

9. Stent with Integrated Actuators and/or Sensors in Parent Vessel:

Although not yet common, the prior art also discloses devices and methods for treating aneurysms which could be called smart stents—featuring integrated microscale actuators (such as MEMS) for controlled expansion and/or sensors to collect biological data. In an example, such smart stents can be implanted within the parent vessel of an aneurysm. Prior art which appears to be within this category includes U.S. Pat. No. 7,235,098 (Palmaz, Jun. 26, 2007, "Medical Devices Having MEMS Functionality and Methods of Making Same"); U.S. Pat. No. 8,019,413 (Ferren et al., Sep. 13, 2011, "Lumen-Traveling Biological Interface Device and Method of Use"); U.S. Pat. No. 8,024,036 (Ferren et al., Sep. 20, 2011, "Lumen-Traveling Biological Interface Device and Method of Use"); U.S. Pat. No. 8,512,219 (Ferren et al., Aug. 20, 2013, "BioelectroMagnetic Interface System"); and U.S. Pat. No. 8,784,475 (Martinson et al., Jul. 22, 2014, "Instrumented Implantable Stents, Vascular Grafts and Other Medical Devices").

Prior art which appears to be within this category also includes U.S. patent applications: 20050065592 (Holzer, Mar. 24, 2005, "System and Method of Aneurism Monitoring and Treatment"); 20080004692 (Henson et al., Jan. 3, 2008, "Dynamically Adjustable Vascular Stent"); 20120271200 (Martinson et al., Oct. 25, 2012, "Instrumented Implantable Stents, Vascular Grafts and Other Medical Devices"); 20130041454 (Dobson et al., Feb. 14, 2013, "Sensor Actuated Stent"); and 20130166017 (Cartledge et al., Jun. 27, 2013, "Actively Controllable Stent, Stent Graft, Heart Valve and Method of Controlling Same"); and Yet unpublished U.S. patent application Ser. No. 12/387,637 (Connor et al., 2009, "Stent with Two-Stage Expansion to Reduce Restenosis").

10. Stent with Other Complex Structure in Parent Vessel:

The prior art also discloses devices and methods for treating aneurysms comprising stents with other complex structures which are implanted within the parent vessel of an aneurysm. Prior art which appears to be within this category includes U.S. Pat. No. 5,370,691 (Samson, Dec. 6, 1994, "Intravascular Inflatable Stent"); U.S. Pat. No. 5,873,907 (Frantzen, Feb. 23, 1999, "Electrolytic Stent Delivery System and Methods of Use"); U.S. Pat. No. 6,007,573 (Wallace et al., Dec. 28, 1999, "Intracranial Stent and Method of Use"); U.S. Pat. No. 6,015,433 (Roth, Jan. 18, 2000, "Rolled Stent with Waveform Perforation Pattern"); U.S. Pat. No. 6,096,175 (Roth, Aug. 1, 2000, "Thin Film Stent"); U.S. Pat. No. 6,406,490 (Roth, Jun. 18, 2002, "Rolled Stent with Waveform Perforation Pattern"); U.S. Pat. No. 6,432,128 (Wallace et al., Aug. 13, 2002, "Intracranial Stent and Method of Use"); U.S. Pat. No. 6,527,919 (Roth, Mar. 4, 2003, "Thin Film Stent"); U.S. Pat. No. 6,579,305 (Lashinski, Jun. 17, 2003, "Method and Apparatus for Delivery Deployment and Retrieval of a Stent Comprising Shape-Memory Material"); U.S. Pat. No. 6,669,719 (Wallace et al., Dec. 30, 2003, "Intracranial Stent and Method of Use"); U.S. Pat. No. 6,916,337 (Roth, Jul. 12, 2005, "Rolled Stent with Waveform Perforation Pattern"); U.S. Pat. No. 7,037,327 (Salmon et al., May 2, 2006, "Stent with Self-Expanding End Sections"); U.S. Pat. No. 7,118,656 (Roth, Oct. 10, 2006, "Thin Film Stent"); U.S. Pat. No. 7,141,063 (White et al., Nov. 28, 2006, "Stent with Micro-Latching Hinge Joints"); and U.S. Pat. No. 7,147,660 (Chobotov et al., Dec. 12, 2006, "Advanced Endovascular Graft").

Prior art which appears to be within this category also includes U.S. Pat. No. 7,147,661 (Chobotov et al., Dec. 12, 2006, "Radially Expandable Stent"); U.S. Pat. No. 7,294,137 (Rivelli et al., Nov. 13, 2007, "Device for Multi-Modal Treatment of Vascular Lesions"); U.S. Pat. No. 7,306,598 (Truckai et al., Dec. 11, 2007, "Polymer Matrix Devices for Treatment of Vascular Malformations"); U.S. Pat. No. 7,323,005 (Wallace et al., Jan. 29, 2008, "Intracranial Stent and Method of Use"); U.S. Pat. No. 7,384,426 (Wallace et al., Jun. 10, 2008, "Intracranial Stent and Method of Use"); U.S. Pat. No. 7,455,753 (Roth, Nov. 25, 2008, "Thin Film Stent"); U.S. Pat. No. 7,547,321 (Silvestri et al., Jun. 16, 2009, "Removable Stent and Method of Using the Same"); U.S. Pat. No. 7,651,525 (Dolan, Jan. 26, 2010, "Intraluminal Stent Assembly and Method of Deploying the Same"); U.S. Pat. No. 7,901,445 (Wallace et al., Mar. 8, 2011, "Intracranial Stent and Method of Use"); U.S. Pat. No. 7,914,574 (Schmid et al., Mar. 29, 2011, "Axially Nested Slide and Lock Expandable Device"); U.S. Pat. No. 7,947,071 (Schmid et al., May 24, 2011, "Expandable Slide and Lock Stent"); U.S. Pat. No. 8,016,853 (Griffen et al., Sep. 13, 2011, "Sacrificial Anode Stent System"); U.S. Pat. No. 8,038,708 (Case et al., Oct. 18, 2011, "Implantable Device with Remodelable Material and Covering Material"); and U.S. Pat. No. 8,147,534 (Berez et al., Apr. 3, 2012, "System and Method for Delivering and Deploying an Occluding Device within a Vessel").

Prior art which appears to be within this category also includes U.S. Pat. No. 8,236,042 (Berez et al., Aug. 7, 2012, "System and Method for Delivering and Deploying an Occluding Device within a Vessel"); U.S. Pat. No. 8,257,421 (Berez et al., Sep. 4, 2012, "System and Method for Delivering and Deploying an Occluding Device within a Vessel"); U.S. Pat. No. 8,267,985 (Garcia et al., Sep. 18, 2012, "System and Method for Delivering and Deploying an Occluding Device within a Vessel"); U.S. Pat. No. 8,273,101 (Garcia et al., Sep. 25, 2012, "System and Method for Delivering and Deploying an Occluding Device within a Vessel"); U.S. Pat. No. 8,277,500 (Schmid et al., Oct. 2, 2012, "Slide-And-Lock Stent"); U.S. Pat. No. 8,292,944 (Schmid et al., Oct. 23, 2012, "Slide-And-Lock Stent"); U.S. Pat. No. 8,377,112 (Griffin et al., Feb. 19, 2013, "Sacrificial Anode Stent System"); U.S. Pat. No. 8,444,686 (Holman et al., May 21, 2013, "Catheter with Removable Balloon Protector and Stent Delivery System with Removable Stent Protector"); U.S. Pat. No. 8,636,760 (Garcia et al., Jan. 28, 2014, "System and Method for Delivering and Deploying an Occluding Device Within a Vessel"); U.S. Pat. No. 8,709,065 (Chobotov, Apr. 29, 2014, "Advanced Endovascular Graft"); and U.S. Pat. No. 8,795,346 (Alkhatib, Aug. 5, 2014, "Semi Rigid Edge Protection Design for Stent Delivery System").

Prior art which appears to be within this category also includes U.S. patent applications: 20020151965 (Roth, Oct. 17, 2002, "Rolled Stent with Waveform Perforation Pattern"); 20030159920 (Roth, Aug. 28, 2003, "Thin Film Stent"); 20040002752 (Griffin et al., Jan. 1, 2004, "Sacrificial Anode Stent System"); 20050192661 (Griffen et al., Sep. 1, 2005, "Sacrificial Anode Stent System"); 20050251247 (Roth, Nov. 10, 2005, "Rolled Stent with Waveform Perforation Pattern"); 20060271149 (Berez et al., Nov. 30, 2006, "System and Method for Delivering and Deploying an Occluding Device within a Vessel"); 20060271153 (Garcia et al., Nov. 30, 2006, "System and Method for Delivering and Deploying an Occluding Device within a Vessel"); 20070031584 (Roth, Feb. 8, 2007, "Thin Film Stent"); and 20080319521 (Norris et al., Dec. 25, 2008, "Compressible Resilient Fabric Devices and Methods").

Prior art which appears to be within this category also includes U.S. patent applications: 20090192536 (Berez et al., Jul. 30, 2009, "System and Method for Delivering and Deploying an Occluding Device Within a Vessel"); 20090198318 (Berez et al., Aug. 6, 2009, "System and Method for Delivering and Deploying an Occluding Device Within a Vessel"); 20090287292 (Becking et al., Nov. 19, 2009, "Braid Implant Delivery Systems"); 20090318947 (Garcia et al., Dec. 24, 2009, "System and Method for Delivering and Deploying an Occluding Device Within a Vessel"); 20100152828 (Pakbaz et al., Jun. 17, 2010, "Devices and Methods for Accessing and Treating an Aneurysm"); 20100179640 (Reith, Jul. 15, 2010, "Radially Expandable System for Use in Body Tubes"); 20110004294 (Bialas, R., Jan. 6, 2011, "Fatigue-Resistant Stent"); 20110066221 (White et al., Mar. 17, 2011, "Hybrid Intraluminal Device"); 20110144740 (Molaei et al., Jun. 6, 2011, "Medical Devices Including Metallic Film and at Least One Filament"); and 20110230957 (Bonsignore et al., Sep. 22, 2011, "Alternating Circumferential Bridge Stent Design and Methods for Use Thereof").

Prior art which appears to be within this category also includes U.S. patent applications: 20110319928 (Griffin et al., Dec. 29, 2011, "Sacrificial Anode Stent System"); 20120221095 (Berez et al., Aug. 30, 2012, "System and Method for Delivering and Deploying an Occluding Device within a Vessel"); 20120277784 (Berez et al., Nov. 1, 2012, "System and Method for Delivering and Deploying an Occluding Device within a Vessel"); 20120283765 (Berez et al., Nov. 8, 2012, "System and Method for Delivering and Deploying an Occluding Device within a Vessel"); 20120283815 (Berez et al., Nov. 8, 2012, "System and Method for Delivering and Deploying an Occluding Device within a Vessel"); 20120316638 (Grad et al., Dec. 13, 2012, "Method and Device for Treating Cerebrovascular Pathologies and Delivery System Therefor"); 20120323547 (Baloch et al., Dec. 20, 2012, "Method for Intracranial Aneurysm Analysis and Endovascular Intervention Planning"); and 20130053872 (Hansen, Feb. 28, 2013, "Device and Method for Preventing Blood Flow into an Aneurysm").

Prior art which appears to be within this category also includes U.S. patent applications: 20130166010 (Vad, Jun. 27, 2013, "Hybrid Balloon-Expandable/Self-Expanding Prosthesis for Deployment in a Body Vessel and Method of Making"); 20130172925 (Garcia et al., Jul. 4, 2013, "System and Method for Delivering and Deploying an Occluding Device within a Vessel"); 20130172976 (Garcia et al., Jul. 4, 2013, "System and Method for Delivering and Deploying an Occluding Device within a Vessel"); 20130211492 (Schneider et al., Aug. 15, 2013, "Implant for Influencing the Blood Flow in Arteriovenous Defects"); 20130253631 (Schmid et al., Sep. 26, 2013, "Slide-And-Lock Stent"); 20130261730 (Bose et al., Oct. 3, 2013, "Aneurysm Occlusion System and Method"); 20130289713 (Pearson et al., Oct. 31, 2013, "Circumferentially Constraining Sutures for a Stent-Graft"); 20140172067 (Brown et al., Jun. 19, 2014, "Luminal Stenting"); 20140180387 (Khenansho et al., Jun. 26, 2014, "Stent Delivery System"); 20140214071 (Thomas, Jul. 31, 2014, "Embolic Coil Delivery System and Method of Using Same"); 20140249614 (Levi et al., Sep. 4, 2014, "Thin Film Vascular Stent and Biocompatible Surface Treatment"); and 20140277391 (Layman et al., Sep. 18, 2014, "Stent and Method of Use").

11. Stent in Parent Vessel to Contain Embolics within Aneurysm Sac:

The prior art also discloses devices and methods for treating aneurysms comprising the implantation of a stent within the parent vessel of an aneurysm in order to contain embolics within an aneurysm sac. This is sometimes called "jailing." In an example, the stent wall can have an opening through which embolic members (such as coils) are inserted into the aneurysm sac. Prior art which appears to be within this category includes U.S. Pat. No. 5,928,260 (Chin et al., Jul. 27, 1999, "Removable Occlusion System for Aneurysm Neck"); U.S. Pat. No. 5,951,599 (McCrory, Sep. 14, 1999, "Occlusion System for Endovascular Treatment of an Aneurysm"); U.S. Pat. No. 5,980,514 (Kupiecki et al., Nov. 9, 1999, "Aneurysm Closure Device Assembly"); U.S. Pat. No. 6,017,977 (Evans et al., Jan. 25, 2000, "Methods for Embolizing Blood Vessels"); U.S. Pat. No. 6,096,034 (Kupiecki et al., Aug. 1, 2000, "Aneurysm Closure Device Assembly"); U.S. Pat. No. 6,168,592 (Kupiecki et al., Jan. 2, 2001, "Aneurysm Closure Device Assembly"); U.S. Pat. No. 6,281,263 (Evans et al., Aug. 28, 2001, "Methods for Embolizing Blood Vessels"); U.S. Pat. No. 6,335,384 (Evans et al., Jan. 1, 2002, "Methods for Embolizing Blood Vessels"); U.S. Pat. No. 6,344,041 (Kupiecki et al., Feb. 5, 2002, "Aneurysm Closure Device Assembly"); and U.S. Pat. No. 6,344,048 (Chin et al., Feb. 5, 2002, "Removable Occlusion System for Aneurysm Neck").

Prior art which appears to be within this category also includes U.S. Pat. No. 6,375,668 (Gifford et al., Apr. 23, 2002, "Devices and Methods for Treating Vascular Malformations"); U.S. Pat. No. 6,746,468 (Sepetka et al., Jun. 8, 2004, "Devices and Methods for Treating Vascular Malformations"); U.S. Pat. No. 6,780,196 (Chin et al., Aug. 24, 2004, "Removable Occlusion System for Aneurysm Neck"); U.S. Pat. No. 6,913,618 (Denardo et al., Jul. 5, 2005, "Intravascular Flow Modifier and Reinforcement Device"); U.S. Pat. No. 7,001,422 (Escamilla et al., Feb. 21, 2006, "Expandable Stent and Delivery System"); U.S. Pat. No. 7,229,461 (Chin et al., Jun. 12, 2007, "Removable Occlusion System for Aneurysm Neck"); U.S. Pat. No. 7,288,112 (Denardo et al., Oct. 30, 2007, "Intravascular Flow Modifier and Reinforcement Device"); U.S. Pat. No. 7,309,351 (Escamilla et al., Dec. 18, 2007, "Expandable Stent with Markers and Stent Delivery System"); U.S. Pat. No. 7,563,270 (Gumm, Jul. 21, 2009, "Rotating Stent Delivery System for Side Branch Access and Protection and Method of Using Same"); and U.S. Pat. No. 7,569,066 (Gerberding et al., Aug. 4, 2009, "Methods and Devices for the Treatment of Aneurysms").

Prior art which appears to be within this category also includes U.S. Pat. No. 7,875,044 (Feller et al., Jan. 25, 2011, "Remodeling Device for Aneurysms"); U.S. Pat. No. 8,016,853 (Griffen et al., Sep. 13, 2011, "Sacrificial Anode Stent System"); U.S. Pat. No. 8,377,112 (Griffin et al., Feb. 19, 2013, "Sacrificial Anode Stent System"); U.S. Pat. No. 8,444,667 (Porter, May 21, 2013, "Device for Closure of a Vascular Defect and Method for Treating the Same"); U.S. Pat. No. 8,470,013 (Duggal et al., Jun. 25, 2013, "Systems and Methods for Aneurysm Treatment and Vessel Occlusion"); U.S. Pat. No. 8,535,367 (Kim et al., Sep. 17, 2013, "Devices and Methods for Treatment of Vascular Aneurysms"); U.S. Pat. No. 8,597,320 (Sepetka et al., Dec. 3, 2013, "Devices and Methods for Treating Vascular Malformations"); U.S. Pat. No. 8,647,377 (Kim et al., Feb. 11, 2014, "Devices and Methods for Treatment of Vascular Aneurysms"); U.S. Pat. No. 8,747,430 (Porter, Jun. 10, 2014, "Device for Closure of a Vascular Defect and Method for Treating the Same"); U.S. Pat. No. 8,771,341 (Strauss et al., Jul. 8, 2014, "Protuberant Aneurysm Bridging Device and Method of Use"); and U.S. Pat. No. 8,808,361 (Strauss et al., Aug. 19, 2014, "Protuberant Aneurysm Bridging Device and Method of Use").

Prior art which appears to be within this category also includes U.S. patent applications: 20020042628 (Chin et al., Apr. 11, 2002, "Removable Occlusion System for Aneurysm Neck"); 20020169473 (Sepetka et al., Nov. 14, 2002, "Devices and Methods for Treating Vascular Malformations"); 20030014075 (Rosenbluth et al., Jan. 16, 2003, "Methods, Materials and Apparatus for Deterring or Preventing Endoleaks Following Endovascular Graft Implantation"); 20040002752 (Griffin et al., Jan. 1, 2004, "Sacrificial Anode Stent System"); 20040181253 (Sepetka et al., Sep. 16, 2004, "Devices and Methods for Treating Vascular Malformations"); 20040193246 (Ferrera, Sep. 30, 2004, "Methods and Apparatus for Treating Aneurysms and Other Vascular Defects"); 20050004660 (Rosenbluth et al., Jan. 6, 2005, "Methods, Materials and Apparatus for Deterring or Preventing Endoleaks Following Endovascular Graft Implantation"); 20050021077 (Chin et al., Jan. 27, 2005, "Removable Occlusion System for Aneurysm Neck"); and 20050192661 (Griffen et al., Sep. 1, 2005, "Sacrificial Anode Stent System").

Prior art which appears to be within this category also includes U.S. patent applications: 20060206196 (Porter, Sep. 14, 2006, "Device for Closure of a Vascular Defect and Method for Treating the Same"); 20060292206 (Kim et al., Dec. 28, 2006, "Devices and Methods for Treatment of Vascular Aneurysms"); 20070050008 (Kim et al., Mar. 1, 2007, "Devices and Methods for Treatment of Vascular Aneurysms"); 20070055355 (Kim et al., Mar. 8, 2007, "Devices and Methods for Treatment of Vascular Aneurysms"); 20070061005 (Kim et al., Mar. 15, 2007, "Devices and Methods for Treatment of Vascular Aneurysms"); 20070150041 (Evans et al., Jun. 28, 2007, "Methods and Systems for Aneurysm Treatment Using Filling Structures"); 20070150045 (Ferrera, Jun. 28, 2007, "Methods and Apparatus for Treating Aneurysms and Other Vascular Defects"); 20080004692 (Henson et al., Jan. 3, 2008, "Dynamically Adjustable Vascular Stent"); 20080033341 (Grad, Feb. 7, 2008, "Methods and Devices for Reducing or Blocking Blood Flow To a Selected Blood Vessel or Part Thereof"); 20080161936 (Feller et al., Jul. 3, 2008, "Remodeling Device for Aneurysms"); and 20090069880 (Vonderwalde et al., Mar. 12, 2009, "Implantable Graft Assembly and Aneurysm Treatment").

Prior art which appears to be within this category also includes U.S. patent applications: 20090125053 (Ferrera et al., May 14, 2009, "Aneurysm Neck Bridging Processes with Revascularization Systems Methods and Products Thereby"); 20090318948 (Linder et al., Dec. 24, 2009, "Device, System and Method for Aneurysm Embolization"); 20100004671 (Gerberding et al., Jan. 7, 2010, "Methods and Devices for the Treatment of Aneurysms"); 20100023105 (Levy et al., Jan. 28, 2010, "Vascular Remodeling Device"); 20100106240 (Duggal et al., Apr. 29, 2010, "Systems and Methods for Aneurysm Treatment and Vessel Occlusion"); 20100131002 (Connor et al., May 27, 2010, "Stent with a Net Layer to Embolize an Aneurysm"); 20110046716 (Parkinson et al., Feb. 24, 2011, "Stent"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); 20110184453 (Levy et al., Jul. 28, 2011, "Vascular Remodeling Device"); 20110224776 (Sepetka et al., Sep. 15, 2011, "Devices and Methods for Treating Vascular Malformations"); and 20110319928 (Griffin et al., Dec. 29, 2011, "Sacrificial Anode Stent System").

Prior art which appears to be within this category also includes U.S. patent applications: 20120245674 (Molaei et al., Sep. 27, 2012, "Vascular Remodeling Device"); 20120245675 (Molaei et al., Sep. 27, 2012, "Vascular Remodeling Device"); 20120283768 (Cox et al., Nov. 8, 2012, "Method and Apparatus for the Treatment of Large and Giant Vascular Defects"); 20120330343 (Kim et al., Dec. 27, 2012, "Devices and Methods for Treatment of Vascular Aneurysms"); 20130116774 (Strauss et al., May 9, 2013, "Protuberant Aneurysm Bridging Device and Method of Use"); 20130231732 (Vonderwalde et al., Sep. 5, 2013, "Implantable Graft Assembly and Aneurysm Treatment"); 20130238083 (Duggal et al., Sep. 12, 2013, "Systems and Methods for Aneurysm Treatment and Vessel Occlusion"); 20130268053 (Molaei et al., Oct. 10, 2013, "Vascular Remodeling Device"); 20130289714 (Strauss et al., Oct. 31, 2013, "Protuberant Aneurysm Bridging Device and Method of Use"); 20140025151 (Gao, Jan. 23, 2014, "Retrievable Stent for Intracranial Aneurysms"); 20140081374 (Kim et al., Mar. 20, 2014, "Devices and Methods for Treatment of Vascular Aneurysms"); 20140121752 (Losordo et al., May 1, 2014, "Wing Bifurcation Reconstruction Device"); and 20140249616 (Strauss et al., Sep. 4, 2014, "Protuberant Aneurysm Bridging Device Deployment Method").

12. Multiple Stents in Parent Vessel:

The prior art also discloses devices and methods for treating aneurysms comprising the coordinated and concurrent implantation of multiple stents (or stent modules) within the parent vessel of an aneurysm. Prior art which appears to be within this category includes U.S. Pat. No. 7,137,993 (Acosta et al., Nov. 21, 2006, "Apparatus and Methods for Delivery of Multiple Distributed Stents"); U.S. Pat. No. 7,147,655 (Chermoni, Dec. 12, 2006, "Balloon Catheter for Multiple Adjustable Stent Deployment"); U.S. Pat. No. 7,294,146 (Chew et al., Nov. 13, 2007, "Apparatus and Methods for Delivery of Variable Length Stents"); U.S. Pat. No. 7,905,913 (Chew et al., Mar. 15, 2011, "Apparatus and Methods for Delivery of Multiple Distributed Stents"); U.S. Pat. No. 7,922,755 (Acosta et al., Apr. 12, 2011, "Apparatus and Methods for Delivery of Multiple Distributed Stents"); U.S. Pat. No. 7,963,987 (Melsheimer et al., Jun. 21, 2011, "Sequential Implant Delivery System"); U.S. Pat. No. 8,016,870 (Chew et al., Sep. 13, 2011, "Apparatus and Methods for Delivery of Variable Length Stents"); U.S. Pat. No. 8,016,871 (Chew et al., Sep. 13, 2011, "Apparatus and Methods for Delivery of Multiple Distributed Stents"); and U.S. Pat. No. 8,246,672 (Osborne, Aug. 21, 2012, "Endovascular Graft with Separately Positionable and Removable Frame Units").

Prior art which appears to be within this category also includes U.S. patent applications: 20030065375 (Eskuri, Apr. 3, 2003, "Nested Stent Apparatus"); 20040215331 (Chew et al., Oct. 28, 2004, "Apparatus and Methods for Delivery of Variable Length Stents"); 20040249435 (Andreas et al., Dec. 9, 2004, "Stent Deployment Systems and Methods"); 20070088368 (Acosta; Pablo et al., Apr. 19, 2007, "Apparatus and Methods for Delivery of Multiple Distributed Stents"); 20090088832 (Chew et al., Apr. 2, 2009, "Apparatus and Methods for Delivery of Variable Length Stents"); 20100318173 (Kolandaivelu et al., Dec. 16, 2010, "Endovascular Devices/Catheter Platforms and Methods for Achieving Congruency in Sequentially Deployed Devices"); and 20110152996 (Acosta et al., Jun. 23, 2011, "Apparatus and Methods for Delivery of Multiple Distributed Stents").

13. Temporary Balloon in Parent Vessel:

The prior art also discloses devices and methods for treating aneurysms comprising the temporarily insertion and expansion of a balloon within the parent vessel of an aneurysm. In an example, temporary insertion and expansion of such as balloon can help to contain a liquid embolic composition within the aneurysm sac while the embolic composition is congealing. As another example, such a balloon can help to contain embolic coils within the aneurysm sac while the coils are being deployed. Prior art which appears to be within this category also includes U.S. Pat. No. 5,776,097 (Massoud, Jul. 7, 1998, "Method and Device for Treating Intracranial Vascular Aneurysms"); U.S. Pat. No. 5,785,679 (Abolfathi et al., Jul. 28, 1998, "Methods and Apparatus for Treating Aneurysms and Arterio-Venous Fistulas"); U.S. Pat. No. 5,795,331 (Cragg et al., Aug. 18, 1998, "Balloon Catheter for Occluding Aneurysms of Branch Vessels"); U.S. Pat. No. 6,074,407 (Levine et al., Jun. 13, 2000, "Delivery Catheter for Occlusive Implants"); U.S. Pat. No. 6,096,021 (Helm et al., Aug. 1, 2000, "Flow Arrest, Double Balloon Technique for Occluding Aneurysms or Blood Vessels"); U.S. Pat. No. 8,221,447 (Solar et al., Jul. 17, 2012, "Aneurysm Coil Delivery System"); and U.S. Pat. No. 8,361,106 (Solar et al., Jan. 29, 2013, "Aneurysm Coil Delivery System").

Prior art which appears to be within this category also includes U.S. patent applications: 20070219578 (Solar et al., Sep. 20, 2007, "Aneurysm Coil Delivery System"); 20080033341 (Grad, Feb. 7, 2008, "Methods and Devices for Reducing or Blocking Blood Flow To a Selected Blood Vessel or Part Thereof"); 20120078285 (Griffin, Mar. 29, 2012, "Balloon Catheter for Intravascular Therapies"); 20120116352 (Rangi, May 10, 2012, "Balloon Assisted Occlusion of Aneurysms"); 20120283764 (Solar et al., Nov. 8, 2012, "Aneurysm Coil Delivery System"); and 20130310687 (Takizawa et al., Nov. 21, 2013, "Blood Vessel Embolization Method Using Balloon Catheter and Balloon Catheter for Blood Vessel Embolization Method").

14. Multi-Balloon Device:

The prior art also discloses devices and methods for treating aneurysms which comprise multiple balloons and/or balloon chambers. In an example, multiple balloons or balloon chambers can be used to differentially expand different portions of a stent within the parent vessel of an aneurysm in order to create structural asymmetry and/or differences in wall porosity. Prior art which appears to be within this category includes U.S. Pat. No. 5,226,889 (Sheiban, Jul. 13, 1993, "Double Balloon Catheter for Stent Implantation"); U.S. Pat. No. 5,304,132 (Jang, Apr. 19, 1994, "Limacon Geometry Balloon Angioplasty Catheter Systems and Method of Making Same"); U.S. Pat. No. 5,536,252 (Imran et al., Jul. 16, 1996, "Angioplasty Catheter with Multiple Coaxial Balloons"); U.S. Pat. No. 5,833,657 (Reinhardt et al., Nov. 10, 1998, "Single-Walled Balloon Catheter with Non-Linear Compliance Characteristic"); U.S. Pat. No. 6,123,712 (Di Caprio et al., Sep. 26, 2000, "Balloon Catheter with Stent Securement Means"); U.S. Pat. No. 6,136,011 (Stambaugh, Oct. 24, 2000, "Stent Delivery System and Method of Use"); and U.S. Pat. No. 6,419,685 (Di Caprio et al., 2002, "Balloon Catheter with Stent Securement Means").

Prior art which appears to be within this category also includes U.S. Pat. No. 6,471,672 (Brown et al., Oct. 29, 2002, "Selective High Pressure Dilation Balloon"); U.S. Pat. No. 6,506,201 (Di Caprio et al., 2003, "Balloon Catheter with Stent Securement Means"); U.S. Pat. No. 6,605,056 (Eidenschink et al., 2003, "Conformable Balloon"); U.S. Pat. No. 7,052,510 (Richter, May 30, 2006, "Two Balloon Staged Stent Expansion"); U.S. Pat. No. 7,300,459 (Heuser, Nov. 27, 2007, "Stent with Covering and Differential Dilation"); U.S. Pat. No. 7,776,079 (Gumm, Aug. 17, 2010, "Conical Balloon for Deployment into Side Branch"); U.S. Pat. No. 8,460,240 (Towler, Jun. 11, 2013, "Inflatable Toroidal-Shaped Balloons"); U.S. Pat. No. 8,657,865 (Gumm, Feb. 25, 2014, "Conical Balloon for Deployment Into Side Branch"); and U.S. Pat. No. 8,709,062 (Dusbabek et al., Apr. 29, 2014, "Stent Delivery System Having Stent Securement Apparatus").

Prior art which appears to be within this category also includes U.S. patent applications: 20030014007 (Eidenschink et al., Jan. 16, 2003, "Conformable Balloon"); 20050209674 (Kutscher et al., Sep. 22, 2005, "Balloon Assembly (V)"); 20070100301 (Gumm, May 3, 2007, "Conical Balloon for Deployment into Side Branch"); 20100063531 (Rudakov et al., Mar. 11, 2010, "Medical Device with Non-Circumferential Surface Portion"); 20100305681 (Gumm, Dec. 2, 2010, "Conical Balloon for Deployment into Side Branch"); 20110238105 (Gelbart et al., Sep. 29, 2011, "Vivo Inflatable Structures for Example to Expand Stents"); 20120116352 (Rangi, May 10, 2012, "Balloon Assisted Occlusion of Aneurysms"); 20130060317 (Dusbabek et al., Mar. 7, 2013, "Stent Delivery System Having Stent Securement Apparatus"); 20130231695 (Malek, Sep. 5, 2013, "Embolic Coil"); 20140222128 (Dusbabek et al., Aug. 7, 2014, "Stent Delivery System Having Stent Securement Apparatus"); and 20140277361 (Farhat et al., Sep. 18, 2014, "Methods and Apparatus for Luminal Stenting"); and Yet unpublished U.S. patent application Ser. No. 13/889,451 (Connor et al., 2013, "Method of Radially-Asymmetric Stent Expansion").

15. Aneurysm Neck Bridge or Saddle in Relatively-Straight Parent Vessel:

The prior art also discloses devices and methods for treating aneurysms comprising an aneurysm neck bridge (or saddle) which is implanted within a relatively-straight portion of a parent vessel. Prior art which appears to be within this category includes U.S. Pat. No. 6,007,573 (Wallace et al., Dec. 28, 1999, "Intracranial Stent and Method of Use"); U.S. Pat. No. 6,093,199 (Brown et al., Jul. 25, 2000, "Intra-Luminal Device for Treatment of Body Cavities and Lumens and Method of Use"); U.S. Pat. No. 6,139,564 (Teoh, Oct. 31, 2000, "Minimally Occlusive Flow Disruptor Stent for Bridging Aneurysm Necks"); U.S. Pat. No. 6,231,597 (Deem et al., May 15, 2001, "Apparatus and Methods for Selectively Stenting a Portion of a Vessel Wall"); U.S. Pat. No. 6,309,367 (Boock, Oct. 30, 2001, "Aneurysm Shield"); U.S. Pat. No. 6,432,128 (Wallace et al., Aug. 13, 2002, "Intracranial Stent and Method of Use"); U.S. Pat. No. 6,605,111 (Bose et al., Aug. 12, 2003, "Endovascular Thin Film Devices and Methods for Treating and Preventing Stroke"); U.S. Pat. No. 6,613,074 (Mitelberg et al., Sep. 2, 2003, "Endovascular Aneurysm Embolization Device"); U.S. Pat. No. 6,669,719 (Wallace et al., Dec. 30, 2003, "Intracranial Stent and Method of Use"); U.S. Pat. No. 6,802,851 (Jones et al., Oct. 12, 2004, "Stent Aneurysm Embolization Method Using Collapsible Member and Embolic Coils"); U.S. Pat. No. 6,811,560 (Jones et al., Nov. 2, 2004, "Stent Aneurysm Embolization Method and Device"); U.S. Pat. No. 7,231,260 (Wallace et al., Jun. 12, 2007, "Intravascular Self-Anchoring Electrode Body with Arcuate Springs, Spring Loops, or Arms"); U.S. Pat. No. 7,241,301 (Thramann et al., Jul. 10, 2007, "Aneurysm Stent with Growth Factor"); U.S. Pat. No. 7,306,622 (Jones et al., Dec. 11, 2007, "Stent Embolization Device"); and U.S. Pat. No. 7,323,005 (Wallace et al., Jan. 29, 2008, "Intracranial Stent and Method of Use").

Prior art which appears to be within this category also includes U.S. Pat. No. 7,384,426 (Wallace et al., Jun. 10, 2008, "Intracranial Stent and Method of Use"); U.S. Pat. No. 7,572,288 (Cox, Aug. 11, 2009, "Aneurysm Treatment Device and Method of Use"); U.S. Pat. No. 7,608,088 (Jones et al., Oct. 27, 2009, "Stent Aneurysm Embolization Device"); U.S. Pat. No. 7,621,928 (Thramann et al., Nov. 24, 2009, "Aneurysm Stent"); U.S. Pat. No. 7,901,445 (Wallace et al., Mar. 8, 2011, "Intracranial Stent and Method of Use"); U.S. Pat. No. 8,038,706 (Eidenschink et al., Oct. 18, 2011, "Crown Stent Assembly"); U.S. Pat. No. 8,187,315 (Clauson et al., May 29, 2012, "Partial Stent for Treatment of a Vascular Aneurysm"); U.S. Pat. No. 8,252,040 (Cox, Aug. 28, 2012, "Aneurysm Treatment Device and Method of Use"); U.S. Pat. No. 8,267,986 (Berez et al., Sep. 18, 2012, "Vascular Stenting for Aneurysms"); U.S. Pat. No. 8,382,825 (Garcia et al., Feb. 26, 2013, "Flexible Vascular Occluding Device"); U.S. Pat. No. 8,398,701 (Berez et al., Mar. 19, 2013, "Flexible Vascular Occluding Device"); U.S. Pat. No. 8,409,267 (Berez et al., Apr. 2, 2013, "Vascular Stenting for Aneurysms"); U.S. Pat. No. 8,409,269 (Berez et al., Apr. 2, 2013, "Procedures for Vascular Occlusion"); U.S. Pat. No. 8,425,548 (Connor, Apr. 23, 2013, "Occluding Member Expansion and then Stent Expansion for Aneurysm Treatment"); U.S. Pat. No. 8,470,013 (Duggal et al., Jun. 25, 2013, "Systems and Methods for Aneurysm Treatment and Vessel Occlusion"); U.S. Pat. No. 8,500,788 (Berez et al., Aug. 6, 2013, "Vascular Stenting and Other Procedures"); U.S. Pat. No. 8,529,614 (Berez et al., Sep. 10, 2013, "Vascular Stenting and Other Procedures"); U.S. Pat. No. 8,529,614 (Berez et al., Sep. 10, 2013, "Vascular Stenting and Other Procedures"); U.S. Pat. No. 8,556,953 (Berez et al., Oct. 15, 2013, "Vascular Stenting for Aneurysms"); U.S. Pat. No. 8,562,667 (Cox, Oct. 22, 2013, "Aneurysm Treatment Device and Method of Use"); and U.S. Pat. No. 8,715,312 (Burke et al., May 6, 2014, "Aneurysm Treatment Device and Method of Use").

Prior art which appears to be within this category also includes U.S. patent applications: 20030018294 (Cox, Jan. 23, 2003, "Aneurysm Treatment Device and Method of Use"); 20030109917 (Rudin et al., Jun. 12, 2003, "Stent Vascular Intervention Device and Method"); 20030139802 (Wulfman et al., Jul. 24, 2003, "Medical Device"); 20050033349 (Jones et al., Feb. 10, 2005, "Stent Aneurysm Embolization Device"); 20050267568 (Berez et al., Dec. 1, 2005, "Flexible Vascular Occluding Device"); 20060206200 (Garcia et al., Sep. 14, 2006, "Flexible Vascular Occluding Device"); 20060206201 (Garcia et al., Sep. 14, 2006, "Flexible Vascular Occluding Device"); 20070021816 (Rudin, Jan. 25, 2007, "Stent Vascular Intervention Device and Methods for Treating Aneurysms"); 20070219610 (Israel, Sep. 20, 2007, "Stent with Flap"); 20070225794 (Thramann et al., Sep. 27, 2007, "Aneurysm Stent"); 20090228029 (Lee, Sep. 10, 2009, "Aneurysm Shield Anchoring Device"); and 20090270974 (Berez et al., Oct. 29, 2009, "Vascular Stenting for Aneurysms").

Prior art which appears to be within this category also includes U.S. patent applications: 20090287241 (Berez et al., Nov. 19, 2009, "Methods and Apparatus for Luminal Stenting"); 20090287288 (Berez et al., Nov. 19, 2009, "Methods and Apparatus for Luminal Stenting"); 20090292348 (Berez et al., Nov. 26, 2009, "Vascular Stenting and Other Procedures"); 20090319017 (Berez et al., Dec. 24, 2009, "Vascular Stenting for Aneurysms"); 20100010624 (Berez et al., Jan. 14, 2010, "Vascular Stenting for Aneurysms"); 20100063531 (Rudakov et al., Mar. 11, 2010, "Medical Device with Non-Circumferential Surface Portion"); 20100082091 (Berez et al., Apr. 1, 2010, "Vascular Stenting and Other Procedures"); 20100106240 (Duggal et al., Apr. 29, 2010, "Systems and Methods for Aneurysm Treatment and Vessel Occlusion"); 20110022149 (Cox et al., Jan. 27, 2011, "Methods and Devices for Treatment of Vascular Defects"); 20110152998 (Berez et al., Jun. 23, 2011, "Procedures for Vascular Occlusion"); and 20110166592 (Garcia et al., Jul. 7, 2011, "Flexible Vascular Occluding Device").

Prior art which appears to be within this category also includes U.S. patent applications: 20110184451 (Sahl, Jul. 28, 2011, "Membrane Implant for Treatment of Cerebral Artery Aneurysms"); 20120004682 (Connor, Jan. 5, 2012, "Occluding Member Expansion and Then Stent Expansion for Aneurysm Treatment"); 20120165919 (Cox et al., Jun. 28, 2012, "Methods and Devices for Treatment of Vascular Defects"); 20130103074 (Riina et al., Apr. 25, 2013, "Method and Apparatus for Restricting Flow Through an Opening in the Side Wall of a Body Lumen, and/or for Reinforcing a Weakness in the Side Wall of a Body Lumen, While Still Maintaining Substantially Normal Flow Through the Body Lumen"); 20130172975 (Berez et al., Jul. 4, 2013, "Methods and Apparatus for Luminal Stenting"); 20130238083 (Duggal et al., Sep. 12, 2013, "Systems and Methods for Aneurysm Treatment and Vessel Occlusion"); 20130274862 (Cox et al., Oct. 17, 2013, "Methods and Devices for Treatment of Vascular Defects"); and 20130274863 (Cox et al., Oct. 17, 2013, "Methods and Devices for Treatment of Vascular Defects").

Prior art which appears to be within this category also includes U.S. patent applications: 20130274866 (Cox et al., Oct. 17, 2013, "Methods and Devices for Treatment of Vascular Defects"); 20130274868 (Cox et al., Oct. 17, 2013, "Methods and Devices for Treatment of Vascular Defects"); 20130282096 (Berez et al., Oct. 24, 2013, "Procedures for Vascular Occlusion"); 20140018843 (Berez et al., Jan. 16, 2014, "Methods and Apparatus for Luminal Stenting"); 20140052233 (Cox et al., Feb. 20, 2014, "Methods and Devices for Treatment of Vascular Defects"); 20140074149 (Garcia et al., Mar. 13, 2014, "Flexible Vascular Occluding Device"); 20140094896 (Berez et al., Apr. 3, 2014, "Vascular Stenting for Aneurysms"); 20140114342 (Berez et al., Apr. 24, 2014, "Flexible Vascular Occluding Device"); 20140128901 (Kang et al., May 8, 2014, "Implant for Aneurysm Treatment"); 20140172071 (Berez et al., Jun. 19, 2014, "Vascular Stenting for Aneurysms"); and 20140288633 (Burke et al., Sep. 25, 2014, "Aneurysm Treatment Device and Method of Use").

16. Aneurysm Neck Bridge or Saddle in Parent Vessel with Three-Way Junction:

The prior art also discloses devices and methods for treating aneurysms comprising an aneurysm neck bridge (or saddle) which is implanted within a parent vessel with a three-way junction. Prior art which appears to be within this category includes U.S. Pat. No. 5,951,599 (McCrory, Sep. 14, 1999, "Occlusion System for Endovascular Treatment of an Aneurysm"); U.S. Pat. No. 6,309,367 (Boock, Oct. 30, 2001, "Aneurysm Shield"); U.S. Pat. No. 6,969,401 (Marotta et al., Nov. 29, 2005, "Endovascular Prosthesis"); U.S. Pat. No. 7,232,461 (Ramer, Jun. 19, 2007, "Neck Covering Device for an Aneurysm"); U.S. Pat. No. 7,572,288 (Cox, Aug. 11, 2009, "Aneurysm Treatment Device and Method of Use"); U.S. Pat. No. 8,252,040 (Cox, Aug. 28, 2012, "Aneurysm Treatment Device and Method of Use"); U.S. Pat. No. 8,388,650 (Gerberding et al., Mar. 5, 2013, "Systems and Methods for Supporting or Occluding a Physiological Opening or Cavity"); U.S. Pat. No. 8,470,013 (Duggal et al., Jun. 25, 2013, "Systems and Methods for Aneurysm Treatment and Vessel Occlusion"); U.S. Pat. No. 8,562,667 (Cox, Oct. 22, 2013, "Aneurysm Treatment Device and Method of Use"); and U.S. Pat. No. 8,715,312 (Burke et al., May 6, 2014, "Aneurysm Treatment Device and Method of Use").

Prior art which appears to be within this category also includes U.S. patent applications: 20030018294 (Cox, Jan. 23, 2003, "Aneurysm Treatment Device and Method of Use"); 20030109917 (Rudin et al., Jun. 12, 2003, "Stent Vascular Intervention Device and Method"); 20040111112 (Hoffmann, Jun. 10, 2004, "Method and Apparatus for Retaining Embolic Material"); 20050096728 (Ramer, May 5, 2005, "Neck Covering Device for an Aneurysm"); 20070021816 (Rudin, Jan. 25, 2007, "Stent Vascular Intervention Device and Methods for Treating Aneurysms"); 20080114391 (Dieck et al., May 15, 2008, "Aneurysm Covering Devices and Delivery Devices"); 20080114436 (Dieck et al., May 15, 2008, "Aneurysm Covering Devices and Delivery Devices"); 20080221600 (Dieck et al., Sep. 11, 2008, "Isolation Devices for the Treatment of Aneurysms"); 20080319533 (Lehe, Dec. 25, 2008, "Aneurysm Occlusion Assist Device"); and 20100094335 (Gerberding et al., Apr.

15, 2010, "Systems and Methods for Supporting or Occluding a Physiological Opening or Cavity").

Prior art which appears to be within this category also includes U.S. patent applications: 20100106240 (Duggal et al., Apr. 29, 2010, "Systems and Methods for Aneurysm Treatment and Vessel Occlusion"); 20100198250 (Ricci et al., Aug. 5, 2010, "Endovascular Prosthesis Delivery System"); 20110022149 (Cox et al., Jan. 27, 2011, "Methods and Devices for Treatment of Vascular Defects"); 20110245862 (Dieck et al., Oct. 6, 2011, "Isolation Devices for the Treatment of Aneurysms"); 20120143237 (Cam et al., Jun. 7, 2012, "Vascular Remodeling Device"); 20120143317 (Cam et al., Jun. 7, 2012, "Vascular Remodeling Device"); 20120165919 (Cox et al., Jun. 28, 2012, "Methods and Devices for Treatment of Vascular Defects"); 20120245674 (Molaei et al., Sep. 27, 2012, "Vascular Remodeling Device"); 20120245675 (Molaei et al., Sep. 27, 2012, "Vascular Remodeling Device"); 20120296361 (Cam et al., Nov. 22, 2012, "Vascular Remodeling Device"); 20120296362 (Cam et al., Nov. 22, 2012, "Vascular Remodeling Device"); 20120316632 (Gao, Dec. 13, 2012, "Retrievable Covered Stent for Bifurcation Aneurysms"); and 20130090682 (Bachman et al., Apr. 11, 2013, "Devices, Systems and Methods for Enclosing an Anatomical Opening").

Prior art which appears to be within this category also includes U.S. patent applications: 20130103074 (Riina et al., Apr. 25, 2013, "Method and Apparatus for Restricting Flow Through an Opening in the Side Wall of a Body Lumen, and/or for Reinforcing a Weakness in the Side Wall of a Body Lumen, While Still Maintaining Substantially Normal Flow Through the Body Lumen"); 20130204290 (Clarke et al., Aug. 8, 2013, "Systems and Methods for Enclosing an Anatomical Opening"); 20130238083 (Duggal et al., Sep. 12, 2013, "Systems and Methods for Aneurysm Treatment and Vessel Occlusion"); 20130268046 (Gerberding et al., Oct. 10, 2013, "Systems and Methods for Supporting or Occluding a Physiological Opening or Cavity"); 20130268053 (Molaei et al., Oct. 10, 2013, "Vascular Remodeling Device"); 20130274862 (Cox et al., Oct. 17, 2013, "Methods and Devices for Treatment of Vascular Defects"); 20130274863 (Cox et al., Oct. 17, 2013, "Methods and Devices for Treatment of Vascular Defects"); and 20130274866 (Cox et al., Oct. 17, 2013, "Methods and Devices for Treatment of Vascular Defects").

Prior art which appears to be within this category also includes U.S. patent applications: 20130274868 (Cox et al., Oct. 17, 2013, "Methods and Devices for Treatment of Vascular Defects"); 20130304109 (Abrams et al., Nov. 14, 2013, "Systems and Methods for Enclosing an Anatomical Opening, Including Coil-Tipped Aneurysm Devices"); 20140039606 (Rudakov et al., Feb. 6, 2014, "Medical Device"); 20140052233 (Cox et al., Feb. 20, 2014, "Methods and Devices for Treatment of Vascular Defects"); 20140058420 (Hannes et al., Feb. 27, 2014, "Implant, Especially for the Occlusion of Bifurcation Aneurysms"); 20140121752 (Losordo et al., May 1, 2014, "Wing Bifurcation Reconstruction Device"); 20140180377 (Bose et al., Jun. 24, 2014, "Aneurysm Occlusion System and Method"); 20140236216 (Gerberding, Aug. 21, 2014, "Systems and Methods for Enclosing an Anatomical Opening, Including Shock Absorbing Aneurysm Devices"); and 20140288633 (Burke et al., Sep. 25, 2014, "Aneurysm Treatment Device and Method of Use").

17. Aneurysm Neck Bridge or Saddle with Spherical Structure in Parent Vessel:

The prior art also discloses devices and methods for treating aneurysms comprising an aneurysm neck bridge (or saddle) with a relatively-spherical structure which is implanted within the parent vessel of an aneurysm. Prior art which appears to be within this category includes U.S. Pat. No. 5,928,260 (Chin et al., Jul. 27, 1999, "Removable Occlusion System for Aneurysm Neck"); U.S. Pat. No. 6,344,048 (Chin et al., Feb. 5, 2002, "Removable Occlusion System for Aneurysm Neck"); U.S. Pat. No. 6,428,558 (Jones et al., Aug. 6, 2002, "Aneurysm Embolization Device"); U.S. Pat. No. 6,780,196 (Chin et al., Aug. 24, 2004, "Removable Occlusion System for Aneurysm Neck"); and U.S. Pat. No. 7,229,461 (Chin et al., Jun. 12, 2007, "Removable Occlusion System for Aneurysm Neck").

Prior art which appears to be within this category also includes U.S. patent applications: 20020042628 (Chin et al., Apr. 11, 2002, "Removable Occlusion System for Aneurysm Neck"); 20050021077 (Chin et al., Jan. 27, 2005, "Removable Occlusion System for Aneurysm Neck"); 20080221600 (Dieck et al., Sep. 11, 2008, "Isolation Devices for the Treatment of Aneurysms"); 20100023105 (Levy et al., Jan. 28, 2010, "Vascular Remodeling Device"); 20110022149 (Cox et al., Jan. 27, 2011, "Methods and Devices for Treatment of Vascular Defects"); 20110184452 (Huynh et al., Jul. 28, 2011, "Vascular Remodeling Device"); 20110184453 (Levy et al., Jul. 28, 2011, "Vascular Remodeling Device"); 20120165919 (Cox et al., Jun. 28, 2012, "Methods and Devices for Treatment of Vascular Defects"); 20130103074 (Riina et al., Apr. 25, 2013, "Method and Apparatus for Restricting Flow Through an Opening in the Side Wall of a Body Lumen, and/or for Reinforcing a Weakness in the Side Wall of a Body Lumen, While Still Maintaining Substantially Normal Flow Through the Body Lumen"); 20130274862 (Cox et al., Oct. 17, 2013, "Methods and Devices for Treatment of Vascular Defects"); 20130274863 (Cox et al., Oct. 17, 2013, "Methods and Devices for Treatment of Vascular Defects"); 20130274866 (Cox et al., Oct. 17, 2013, "Methods and Devices for Treatment of Vascular Defects"); 20130274868 (Cox et al., Oct. 17, 2013, "Methods and Devices for Treatment of Vascular Defects"); and 20140052233 (Cox et al., Feb. 20, 2014, "Methods and Devices for Treatment of Vascular Defects").

18. Localized Aneurysm Neck Bridge in Parent Vessel:

Although not common, the prior art also discloses devices and methods for treating aneurysms comprising a localized aneurysm neck bridge within the parent vessel of an aneurysm which is attached to the aneurysm neck by non-compressive methods such as adhesion or barbs. Saddle-like devices in the parent vessel which are held in place against the aneurysm neck by more-extensive compressive structures in the parent vessel are included in a different category. Prior art which appears to be within this category includes U.S. Pat. No. 5,941,249 (Maynard, Aug. 24, 1999, "Distributed Activator for a Two-Dimensional Shape Memory Alloy"); U.S. Pat. No. 6,409,749 (Maynard, Jun. 25, 2002, "Aneurism Patch Including Distributed Activator for a Two-Dimensional Shape Memory Alloy"); U.S. Pat. No. 6,746,468 (Sepetka et al., Jun. 8, 2004, "Devices and Methods for Treating Vascular Malformations"); U.S. Pat. No. 7,241,301 (Thramann et al., Jul. 10, 2007, "Aneurysm Stent with Growth Factor"); U.S. Pat. No. 7,569,066 (Gerberding et al., Aug. 4, 2009, "Methods and Devices for the Treatment of Aneurysms"); U.S. Pat. No. 7,621,928 (Thramann et al., Nov. 24, 2009, "Aneurysm Stent"); and U.S. Pat. No.

8,597,320 (Sepetka et al., Dec. 3, 2013, "Devices and Methods for Treating Vascular Malformations").

Prior art which appears to be within this category also includes U.S. patent applications: 20020169473 (Sepetka et al., Nov. 14, 2002, "Devices and Methods for Treating Vascular Malformations"); 20040181253 (Sepetka et al., Sep. 16, 2004, "Devices and Methods for Treating Vascular Malformations"); 20070225794 (Thramann et al., Sep. 27, 2007, "Aneurysm Stent"); 20100004671 (Gerberding et al., Jan. 7, 2010, "Methods and Devices for the Treatment of Aneurysms"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); 20110224776 (Sepetka et al., Sep. 15, 2011, "Devices and Methods for Treating Vascular Malformations"); 20130103074 (Riina et al., Apr. 25, 2013, "Method and Apparatus for Restricting Flow Through an Opening in the Side Wall of a Body Lumen, and/or for Reinforcing a Weakness in the Side Wall of a Body Lumen, While Still Maintaining Substantially Normal Flow Through the Body Lumen"); and 20130197570 (Ebata et al., Aug. 1, 2013, "Device for Closing Luminal Cavity and Method Therefor").

19. Aneurysm Neck Bridge Spanning Aneurysm Sac and Parent Vessel:

The prior art also discloses devices and methods for treating aneurysms comprising an aneurysm neck bridge which compresses the aneurysm neck from both inside and outside the aneurysm sac. In an example, such a device can have a pre-compression hourglass shape, wherein the intrasacular portion of the hourglass shape compresses the aneurysm neck from inside the sac and the parent vessel portion of the hourglass shape compresses the aneurysm neck from outside the sac. In an example, this type of device can act like an internal aneurysm clip or clamp.

Prior art which appears to be within this category includes U.S. Pat. No. 6,168,622 (Mazzocchi, Jan. 2, 2001, "Method and Apparatus for Occluding Aneurysms"); U.S. Pat. No. 6,506,204 (Mazzocchi, Jan. 14, 2003, "Method and Apparatus for Occluding Aneurysms"); U.S. Pat. No. 6,746,468 (Sepetka et al., Jun. 8, 2004, "Devices and Methods for Treating Vascular Malformations"); U.S. Pat. No. 6,855,154 (Abdel-Gawwad, Feb. 15, 2005, "Endovascular Aneurysm Treatment Device and Method"); U.S. Pat. No. 7,195,636 (Avellanet et al., Mar. 27, 2007, "Aneurysm Neck Cover for Sealing an Aneurysm"); U.S. Pat. No. 7,241,301 (Thramann et al., Jul. 10, 2007, "Aneurysm Stent with Growth Factor"); U.S. Pat. No. 7,569,066 (Gerberding et al., Aug. 4, 2009, "Methods and Devices for the Treatment of Aneurysms"); U.S. Pat. No. 7,621,928 (Thramann et al., Nov. 24, 2009, "Aneurysm Stent"); U.S. Pat. No. 7,744,652 (Morsi, Jun. 29, 2010, "Aneurysm Sealing Device"); U.S. Pat. No. 7,993,364 (Morsi, Aug. 9, 2011, "Aneurysm Flow Barrier"); U.S. Pat. No. 8,062,379 (Morsi, Nov. 22, 2011, "Aneurysm Sealing Device"); and U.S. Pat. No. 8,075,585 (Lee et al., Dec. 13, 2011, "Device and Method for Treatment of a Vascular Defect"); U.S. Pat. No. 8,292,914 (Morsi, Oct. 23, 2012, "Aneurysm Flow Barrier").

Prior art which appears to be within this category also includes U.S. Pat. No. 8,357,180 (Feller et al., Jan. 22, 2013, "Thin Film Metallic Device for Plugging Aneurysms or Vessels"); U.S. Pat. No. 8,372,114 (Hines, Feb. 12, 2013, "Over-The-Wire Exclusion Device and System for Delivery"); U.S. Pat. No. 8,398,670 (Amplatz et al., Mar. 19, 2013, "Multi-Layer Braided Structures for Occluding Vascular Defects and for Occluding Fluid Flow Through Portions of the Vasculature of the Body"); U.S. Pat. No. 8,444,667 (Porter, May 21, 2013, "Device for Closure of a Vascular Defect and Method for Treating the Same"); U.S. Pat. No. 8,597,320 (Sepetka et al., Dec. 3, 2013, "Devices and Methods for Treating Vascular Malformations"); U.S. Pat. No. 8,668,716 (Hines, Mar. 11, 2014, "Over-the-Wire Exclusion Device and System for Delivery"); U.S. Pat. No. 8,668,717 (Hines, Mar. 11, 2014, "Over-the-Wire Exclusion Device and System for Delivery"); and U.S. Pat. No. 8,747,430 (Porter, Jun. 10, 2014, "Device for Closure of a Vascular Defect and Method for Treating the Same").

Prior art which appears to be within this category also includes U.S. patent applications: 20010000797 (Mazzocchi, May 3, 2001, "Method and Apparatus for Occluding Aneurysms"); 20020169473 (Sepetka et al., Nov. 14, 2002, "Devices and Methods for Treating Vascular Malformations"); 20030093108 (Avellanet et al., May 15, 2003, "Aneurysm Neck Cover for Sealing an Aneurysm"); 20030195553 (Wallace, et al., Oct. 16, 2003, "System and Method for Retaining Vaso-Occlusive Devices Within an Aneurysm"); 20040181253 (Sepetka et al., Sep. 16, 2004, "Devices and Methods for Treating Vascular Malformations"); 20050228434 (Amplatz et al., Oct. 13, 2005, "Multi-Layer Braided Structures for Occluding Vascular Defects"); and 20060206196 (Porter, Sep. 14, 2006, "Device for Closure of a Vascular Defect and Method for Treating the Same").

Prior art which appears to be within this category also includes U.S. patent applications: 20060241690 (Amplatz et al., Oct. 26, 2006, "Multi-Layer Braided Structures for Occluding Vascular Defects and for Occluding Fluid Flow Through Portions of the Vasculature of the Body"); 20070088387 (Eskridge et al., Apr. 19, 2007, "Implantable Aneurysm Closure Systems and Methods"); 20070106311 (Wallace et al., May 10, 2007, "System and Method for Retaining Vaso-Occlusive Devices Within an Aneurysm"); 20070225794 (Thramann et al., Sep. 27, 2007, "Aneurysm Stent"); 20070265656 (Amplatz et al., Nov. 15, 2007, "Multi-Layer Braided Structures for Occluding Vascular Defects"); 20080097495 (Feller et al., Apr. 24, 2008, "Thin Film Metallic Device for Plugging Aneurysms or Vessels"); and 20080200945 (Amplatz et al., Aug. 21, 2008, "Device for Occluding Vascular Defects").

Prior art which appears to be within this category also includes U.S. patent applications: 20090062841 (Amplatz et al., Mar. 5, 2009, "Device for Occluding Vascular Defects"); 20090299326 (Morsi, Dec. 3, 2009, "Endovascular Aneurysm Treatment Device and Method"); 20100004671 (Gerberding et al., Jan. 7, 2010, "Methods and Devices for the Treatment of Aneurysms"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); 20110196413 (Wallace et al., Aug. 11, 2011, "System and Method for Retaining Vaso-Occlusive Devices Within an Aneurysm"); 20110224776 (Sepetka et al., Sep. 15, 2011, "Devices and Methods for Treating Vascular Malformations"); and 20120046676 (Morsi, Feb. 23, 2012, "Aneurysm Flow Barrier").

Prior art which appears to be within this category also includes U.S. patent applications: 20120253369 (Morsi, Oct. 4, 2012, "Advanced Endovascular Clip and Method of Using Same"); 20130012979 (Amplatz et al., Jan. 10, 2013, "Multi-Layer Braided Structures for Occluding Vascular Defects and for Occluding Fluid Flow Through Portions of the Vasculature of the Body"); 20130197547 (Fukuoka et al., Aug. 1, 2013, "Device for Closing Luminal Cavity and Method Therefor"); 20130267986 (Hines, Oct. 10, 2013, "Over-The-Wire Exclusion Device and System for Delivery"); 20130345738 (Eskridge, Dec. 26, 2013, "Endovascular Closure Device"); and 20140005698 (Eskridge, Jan. 2, 2014, "Endovascular Closure System").

20. Aneurysm Neck Bridge Inside Aneurysm Sac with Radial Protrusions:

The prior art also discloses devices and methods for treating aneurysms comprising an aneurysm neck bridge with radially-extending loops, petals, or undulations which is implanted inside the aneurysm sac. In example, such a neck bridge can be held against the inside surface of the aneurysm neck by pressure from embolic members which are inserted into the sac. In an example, such a neck bridge can be held against the inside surface of the aneurysm neck by one or more tensile members which are in contact with the walls of the aneurysm sac.

Prior art which appears to be within this category includes U.S. Pat. No. 5,733,294 (Forber et al., Mar. 31, 1998, "Self Expanding Cardiovascular Occlusion Device, Method of Using and Method of Making the Same"); U.S. Pat. No. 5,935,148 (Villar et al., Aug. 10, 1999, "Detachable, Varying Flexibility, Aneurysm Neck Bridge"); U.S. Pat. No. 6,036,720 (Abrams et al., Mar. 14, 2000, "Sheet Metal Aneurysm Neck Bridge"); U.S. Pat. No. 6,063,070 (Eder, May 16, 2000, "Detachable Aneurysm Neck Bridge (II)"); U.S. Pat. No. 6,063,104 (Villar et al., May 16, 2000, "Detachable, Varying Flexibility, Aneurysm Neck Bridge"); U.S. Pat. No. 6,383,174 (Eder, May 7, 2002, "Detachable Aneurysm Neck Bridge (II)"); and U.S. Pat. No. 6,746,468 (Sepetka et al., Jun. 8, 2004, "Devices and Methods for Treating Vascular Malformations").

Prior art which appears to be within this category also includes U.S. Pat. No. 7,410,482 (Murphy et al., Aug. 12, 2008, "Detachable Aneurysm Neck Bridge"); U.S. Pat. No. 7,713,264 (Murphy et al., May 11, 2010, "Detachable Aneurysm Neck Bridge"); U.S. Pat. No. 8,267,923 (Murphy et al., Sep. 18, 2012, "Detachable Aneurysm Neck Bridge"); U.S. Pat. No. 8,372,062 (Murphy et al., Feb. 12, 2013, "Detachable Aneurysm Neck Bridge"); U.S. Pat. No. 8,449,532 (Murphy et al., May 28, 2013, "Detachable Aneurysm Neck Bridge"); U.S. Pat. No. 8,529,556 (Murphy et al., Sep. 10, 2013, "Detachable Aneurysm Neck Bridge"); and U.S. Pat. No. 8,597,320 (Sepetka et al., Dec. 3, 2013, "Devices and Methods for Treating Vascular Malformations").

Prior art which appears to be within this category also includes U.S. patent applications: 20020169473 (Sepetka et al., Nov. 14, 2002, "Devices and Methods for Treating Vascular Malformations"); 20040093014 (Ho et al., May 13, 2004, "Bioactive Components for Incorporation with Vaso-Occlusive Members"); 20040098027 (Teoh et al., May 20, 2004, "Expandable Body Cavity Liner Device"); 20040181253 (Sepetka et al., Sep. 16, 2004, "Devices and Methods for Treating Vascular Malformations"); 20070088387 (Eskridge et al., Apr. 19, 2007, "Implantable Aneurysm Closure Systems and Methods"); 20100222804 (Murphy et al., Sep. 2, 2010, "Detachable Aneurysm Neck Bridge"); 20110022149 (Cox et al., Jan. 27, 2011, "Methods and Devices for Treatment of Vascular Defects"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); and 20110224776 (Sepetka et al., Sep. 15, 2011, "Devices and Methods for Treating Vascular Malformations").

Prior art which appears to be within this category also includes U.S. patent applications: 20110282378 (Murphy et al., Nov. 17, 2011, "Detachable Aneurysm Neck Bridge"); 20120165919 (Cox et al., Jun. 28, 2012, "Methods and Devices for Treatment of Vascular Defects"); 20120310270 (Murphy et al., Feb. 12, 2013, "Detachable Aneurysm Neck Bridge"); 20130035712 (Theobald et al., Feb. 7, 2013, "Cerebral Aneurysm Closure Device"); 20130190800 (Murphy et al., Jul. 25, 2013, "Detachable Aneurysm Neck Bridge"); 20130274862 (Cox et al., Oct. 17, 2013, "Methods and Devices for Treatment of Vascular Defects"); 20130274863 (Cox et al., Oct. 17, 2013, "Methods and Devices for Treatment of Vascular Defects"); 20130274866 (Cox et al., Oct. 17, 2013, "Methods and Devices for Treatment of Vascular Defects"); 20130274868 (Cox et al., Oct. 17, 2013, "Methods and Devices for Treatment of Vascular Defects"); 20140052233 (Cox et al., Feb. 20, 2014, "Methods and Devices for Treatment of Vascular Defects"); and 20140207162 (Tran et al., Jul. 24, 2014, "Occlusive Cinching Devices and Methods of Use").

21. Aneurysm Neck Bridge Inside Aneurysm Sac with Convex Shape:

The prior art also discloses devices and methods for treating aneurysms comprising an aneurysm neck bridge with a bowl shape, cup shape, or other generally-convex shape which is implanted inside the aneurysm sac. In example, such a neck bridge can be held against the inside surface of the aneurysm neck by pressure from embolic members which are inserted into the sac. In an example, such a neck bridge can be held against the inside surface of the aneurysm neck by one or more tensile members which are in contact with the walls of the aneurysm sac.

Prior art which appears to be within this category includes U.S. Pat. No. 6,168,615 (Ken et al., Jan. 2, 2001, "Method and Apparatus for Occlusion and Reinforcement of Aneurysms"); U.S. Pat. No. 6,454,780 (Wallace, Sep. 24, 2002, "Aneurysm Neck Obstruction Device"); U.S. Pat. No. 6,605,111 (Bose et al., Aug. 12, 2003, "Endovascular Thin Film Devices and Methods for Treating and Preventing Stroke"); U.S. Pat. No. 6,802,851 (Jones et al., Oct. 12, 2004, "Stent Aneurysm Embolization Method Using Collapsible Member and Embolic Coils"); U.S. Pat. No. 6,811,560 (Jones et al., Nov. 2, 2004, "Stent Aneurysm Embolization Method and Device"); U.S. Pat. No. 7,083,632 (Avellanet et al., Aug. 1, 2006, "Aneurysm Embolic Device with an Occlusive Member"); U.S. Pat. No. 7,128,736 (Abrams et al., Oct. 31, 2006, "Detachable Aneurysm Neck Closure Patch"); and U.S. Pat. No. 7,241,301 (Thramann et al., Jul. 10, 2007, "Aneurysm Stent with Growth Factor").

Prior art which appears to be within this category also includes U.S. Pat. No. 7,306,622 (Jones et al., Dec. 11, 2007, "Stent Embolization Device"); U.S. Pat. No. 7,569,066 (Gerberding et al., Aug. 4, 2009, "Methods and Devices for the Treatment of Aneurysms"); U.S. Pat. No. 7,572,288 (Cox, Aug. 11, 2009, "Aneurysm Treatment Device and Method of Use"); U.S. Pat. No. 7,608,088 (Jones et al., Oct. 27, 2009, "Stent Aneurysm Embolization Device"); U.S. Pat. No. 7,621,928 (Thramann et al., Nov. 24, 2009, "Aneurysm Stent"); U.S. Pat. No. 8,252,040 (Cox, Aug. 28, 2012, "Aneurysm Treatment Device and Method of Use"); U.S. Pat. No. 8,444,667 (Porter, May 21, 2013, "Device for Closure of a Vascular Defect and Method for Treating the Same"); U.S. Pat. No. 8,562,667 (Cox, Oct. 22, 2013, "Aneurysm Treatment Device and Method of Use"); U.S. Pat. No. 8,715,312 (Burke et al., May 6, 2014, "Aneurysm Treatment Device and Method of Use"); and U.S. Pat. No. 8,747,430 (Porter, Jun. 10, 2014, "Device for Closure of a Vascular Defect and Method for Treating the Same").

Prior art which appears to be within this category also includes U.S. patent applications: 20030018294 (Cox, Jan. 23, 2003, "Aneurysm Treatment Device and Method of Use"); 20030083676 (Wallace, May 1, 2003, "Aneurysm Neck Obstruction Device"); 20030093097 (Avellanet et al., May 15, 2003, "Aneurysm Embolic Device with an Occlusive Member"); 20030181927 (Wallace, Sep. 25, 2003, "Aneurysm Neck Obstruction Device"); 20030195553 (Wallace, et al., Oct. 16, 2003, "System and Method for Retaining Vaso-Occlusive Devices Within an Aneurysm"); 20040098027 (Teoh et al., May 20, 2004, "Expandable Body Cavity Liner Device"); 20050033349 (Jones et al., Feb. 10, 2005, "Stent Aneurysm Embolization Device"); 20060155323 (Porter et al., Jul. 13, 2006, "Intra-Aneurysm Devices"); and 20060206196 (Porter, Sep. 14, 2006, "Device for Closure of a Vascular Defect and Method for Treating the Same").

Prior art which appears to be within this category also includes U.S. patent applications: 20060235464 (Avellanet et al., Oct. 19, 2006, "Aneurysm Embolic Device with an Occlusive Member"); 20070088387 (Eskridge et al., Apr. 19, 2007, "Implantable Aneurysm Closure Systems and Methods"); 20070106311 (Wallace et al., May 10, 2007, "System and Method for Retaining Vaso-Occlusive Devices Within an Aneurysm"); 20070225794 (Thramann et al., Sep. 27, 2007, "Aneurysm Stent"); 20080147100 (Wallace, Jun. 19, 2008, "Aneurysm Neck Obstruction Device"); 20080281350 (Sepetka et al., Nov. 13, 2008, "Aneurysm Occlusion Devices"); 20100004671 (Gerberding et al., Jan. 7, 2010, "Methods and Devices for the Treatment of Aneurysms"); 20110022149 (Cox et al., Jan. 27, 2011, "Methods and Devices for Treatment of Vascular Defects"); 20110144669 (Becking et al., Jun. 16, 2011, "Aneurysm Cover Device for Embolic Delivery and Retention"); and 20110196413 (Wallace et al., Aug. 11, 2011, "System and Method for Retaining Vaso-Occlusive Devices Within an Aneurysm").

Prior art which appears to be within this category also includes U.S. patent applications: 20120143237 (Cam et al., Jun. 7, 2012, "Vascular Remodeling Device"); 20120143317 (Cam et al., Jun. 7, 2012, "Vascular Remodeling Device"); 20120165919 (Cox et al., Jun. 28, 2012, "Methods and Devices for Treatment of Vascular Defects"); 20130274862 (Cox et al., Oct. 17, 2013, "Methods and Devices for Treatment of Vascular Defects"); 20130274863 (Cox et al., Oct. 17, 2013, "Methods and Devices for Treatment of Vascular Defects"); 20130274866 (Cox et al., Oct. 17, 2013, "Methods and Devices for Treatment of Vascular Defects"); 20130274868 (Cox et al., Oct. 17, 2013, "Methods and Devices for Treatment of Vascular Defects"); 20130325053 (Porter et al., Dec. 5, 2013, "Intra-Aneurysm Devices"); 20140052233 (Cox et al., Feb. 20, 2014, "Methods and Devices for Treatment of Vascular Defects"); 20140135810 (Divino et al., May 15, 2014, "Occlusive Devices"); 20140135811 (Divino et al., May 15, 2014, "Occlusive Devices"); 20140135812 (Divino et al., May 15, 2014, "Occlusive Devices"); and 20140288633 (Burke et al., Sep. 25, 2014, "Aneurysm Treatment Device and Method of Use").

22. Single-Chamber Woven/Mesh Structure in Aneurysm Sac:

The prior art also discloses devices and methods for treating aneurysms comprising single-chamber woven and/or mesh structures which are expanded within the aneurysm sac. In an example, such structures can be formed from arcuate metal wires or filaments. Generally, such structures are expanded into a hollow, but compression-resilient, geometric shape within the aneurysm sac. Relatively spherical, ellipsoid, and toroidal shapes are common. To paraphrase Jerry Lee Lewis—"Goodness. Gracious. Great balls of wire!"

Prior art which appears to be within this category includes U.S. Pat. No. 5,766,219 (Horton, Jun. 16, 1998, "Anatomically Shaped Vasoocclusive Device and Method for Deploying Same"); U.S. Pat. No. 5,911,731 (Pham et al., Jun. 15, 1999, "Anatomically Shaped Vasoocclusive Devices"); U.S. Pat. No. 6,346,117 (Greenhalgh, Feb. 12, 2002, "Bag for Use in the Intravascular Treatment of Saccular Aneurysms"); U.S. Pat. No. 6,375,668 (Gifford et al., Apr. 23, 2002, "Devices and Methods for Treating Vascular Malformations"); U.S. Pat. No. 6,391,037 (Greenhalgh, May 21, 2002, "Bag for Use in the Intravascular Treatment of Saccular Aneurysms"); U.S. Pat. No. 6,746,468 (Sepetka et al., Jun. 8, 2004, "Devices and Methods for Treating Vascular Malformations"); U.S. Pat. No. 8,142,456 (Rosqueta et al., Mar. 27, 2012, "Braid-Ball Embolic Devices"); U.S. Pat. No. 8,597,320 (Sepetka et al., Dec. 3, 2013, "Devices and Methods for Treating Vascular Malformations"); U.S. Pat. No. 8,597,323 (Plaza et al., Dec. 3, 2013, "Delivery and Detachment Systems and Methods for Vascular Implants"); U.S. Pat. No. 8,696,701 (Becking et al., Apr. 15, 2014, "Braid-Ball Embolic Devices"); and U.S. Pat. No. 8,747,597 (Rosqueta et al., Jun. 10, 2014, "Methods for Making Braid-Ball Occlusion Devices").

Prior art which appears to be within this category also includes U.S. patent applications: 20020169473 (Sepetka et al., Nov. 14, 2002, "Devices and Methods for Treating Vascular Malformations"); 20040098027 (Teoh et al., May 20, 2004, "Expandable Body Cavity Liner Device"); 20040181253 (Sepetka et al., Sep. 16, 2004, "Devices and Methods for Treating Vascular Malformations"); 20060052816 (Bates et al., Mar. 9, 2006, "Device for Treating an Aneurysm"); 20060155323 (Porter et al., Jul. 13, 2006, "Intra-Aneurysm Devices"); 20090275974 (Marchand et al., Nov. 5, 2009, "Filamentary Devices for Treatment of Vascular Defects"); 20090287291 (Becking et al., Nov. 19, 2009, "Embolic Device Delivery Systems"); 20090287294 (Rosqueta et al., Nov. 19, 2009, "Braid-Ball Embolic Devices"); 20090318941 (Sepetka et al., Dec. 24, 2009, "Self-Expandable Endovascular Device for Aneurysm Occlusion"); and 20100069948 (Veznedaroglu et al., Mar. 18, 2010, "Self-Expandable Aneurysm Filling Device System and Method of Placement").

Prior art which appears to be within this category also includes U.S. patent applications: 20110022149 (Cox et al., Jan. 27, 2011, "Methods and Devices for Treatment of Vascular Defects"); 20110082491 (Sepetka et al., Apr. 7, 2011, "Devices and Methods for Treating Vascular Malformations"); 20110137332 (Sepetka et al., Jun. 9, 2011, "Devices and Methods for Treating Vascular Malformations"); 20110152993 (Marchand et al., Jun. 23, 2011, "Multiple Layer Filamentary Devices for Treatment of Vascular Defects"); 20110202085 (Loganathan et al., Aug. 18, 2011, "Braid Ball Embolic Device Features"); 20110208227 (Becking, Aug. 25, 2011, "Filamentary Devices for Treatment of Vascular Defects"); 20110224776 (Sepetka et al., Sep. 15, 2011, "Devices and Methods for Treating Vascular Malformations"); 20110265943 (Rosqueta et al., Nov. 3, 2011, "Methods for Making Braid-Ball Occlusion Devices"); 20110319926 (Becking et al., Dec. 29, 2011, "Braid Ball Embolic Device Features"); and 20120071911 (Sadasivan et al., Mar. 22, 2012, "Spherical Helix Embolic Coils for the Treatment of Cerebral Aneurysms").

Prior art which appears to be within this category also includes U.S. patent applications: 20120165919 (Cox et al., Jun. 28, 2012, "Methods and Devices for Treatment of Vascular Defects"); 20120197283 (Marchand et al., Aug. 2, 2012, "Multiple Layer Filamentary Devices for Treatment of Vascular Defects"); 20120283768 (Cox et al., Nov. 8, 2012, "Method and Apparatus for the Treatment of Large and Giant Vascular Defects"); 20120316598 (Becking et al., Dec. 13, 2012, "Multiple Layer Filamentary Devices for Treatment of Vascular Defects"); 20120330347 (Becking et al., Dec. 27, 2012, "Multiple Layer Filamentary Devices for Treatment of Vascular Defects"); 20130066360 (Becking et al., Mar. 14, 2013, "Braid-Ball Embolic Devices"); 20130085522 (Becking et al., Apr. 4, 2013, "Braid-Ball Embolic Devices"); and 20130103074 (Riina et al., Apr. 25, 2013, "Method and Apparatus for Restricting Flow Through an Opening in the Side Wall of a Body Lumen, and/or for Reinforcing a Weakness in the Side Wall of a Body Lumen, While Still Maintaining Substantially Normal Flow Through the Body Lumen").

Prior art which appears to be within this category also includes U.S. patent applications: 20130123830 (Becking et al., May 16, 2013, "Multiple Layer Filamentary Devices for Treatment of Vascular Defects"); 20130245667 (Marchand et al., Sep. 19, 2013, "Filamentary Devices and Treatment of Vascular Defects"); 20130274862 (Cox et al., Oct. 17, 2013, "Methods and Devices for Treatment of Vascular Defects"); 20130274863 (Cox et al., Oct. 17, 2013, "Methods and Devices for Treatment of Vascular Defects"); 20130274866 (Cox et al., Oct. 17, 2013, "Methods and Devices for Treatment of Vascular Defects"); 20130274868 (Cox et al., Oct. 17, 2013, "Methods and Devices for Treatment of Vascular Defects"); 20130325053 (Porter et al., Dec. 5, 2013, "Intra-Aneurysm Devices"); 20140012307 (Franano et al., Jan. 9, 2014, "Detachable Metal Balloon Delivery Device and Method"); 20140012363 (Franano et al., Jan. 9, 2014, "Ballstent Device and Methods of Use"); and 20140052233 (Cox et al., Feb. 20, 2014, "Methods and Devices for Treatment of Vascular Defects").

Prior art which appears to be within this category also includes U.S. patent applications: 20140135810 (Divino et al., May 15, 2014, "Occlusive Devices"); 20140135811 (Divino et al., May 15, 2014, "Occlusive Devices"); 20140135812 (Divino et al., May 15, 2014, "Occlusive Devices"); 20140142611 (Plaza et al., May 22, 2014, "Delivery and Detachment Systems and Methods for Vascular Implants"); 20140172001 (Becking et al., Jun. 19, 2014, "Two-Stage Deployment Aneurysm Embolization Devices"); and 20140200607 (Sepetka et al., Jul. 17, 2014, "Occlusive Device").

23. Multi-Chamber Woven/Mesh Structure in Aneurysm Sac:

The prior art also discloses devices and methods for treating aneurysms comprising multi-chamber woven and/or mesh structures which are expanded within the aneurysm sac. In an example, such structures can be formed from arcuate metal wires or filaments. Generally, such structures are expanded into one or more hollow, but compression-resilient, geometric shapes within the aneurysm sac. Prior art which appears to be within this category includes U.S. Pat. No. 6,168,622 (Mazzocchi, Jan. 2, 2001, "Method and Apparatus for Occluding Aneurysms"); U.S. Pat. No. 6,375,668 (Gifford et al., Apr. 23, 2002, "Devices and Methods for Treating Vascular Malformations"); U.S. Pat. No. 6,506,204 (Mazzocchi, Jan. 14, 2003, "Method and Apparatus for Occluding Aneurysms"); U.S. Pat. No. 6,746,468 (Sepetka et al., Jun. 8, 2004, "Devices and Methods for Treating Vascular Malformations"); U.S. Pat. No. 7,993,364 (Morsi, Aug. 9, 2011, "Aneurysm Flow Barrier"); U.S. Pat. No. 8,066,036 (Monetti et al., Nov. 29, 2011, "Three-Dimensional Complex Coil"); U.S. Pat. No. 8,292,914 (Morsi, Oct. 23, 2012, "Aneurysm Flow Barrier"); and U.S. Pat. No. 8,597,320 (Sepetka et al., Dec. 3, 2013, "Devices and Methods for Treating Vascular Malformations").

Prior art which appears to be within this category also includes U.S. patent applications: 20010000797 (Mazzocchi, May 3, 2001, "Method and Apparatus for Occluding Aneurysms"); 20020169473 (Sepetka et al., Nov. 14, 2002, "Devices and Methods for Treating Vascular Malformations"); 20040181253 (Sepetka et al., Sep. 16, 2004, "Devices and Methods for Treating Vascular Malformations"); 20060052816 (Bates et al., Mar. 9, 2006, "Device for Treating an Aneurysm"); 20070175536 (Monetti et al., Aug. 2, 2007, "Three-Dimensional Complex Coil"); 20090297582 (Meyer et al., Dec. 3, 2009, "Vascular Occlusion Devices and Methods"); 20090299326 (Morsi, Dec. 3, 2009, "Endovascular Aneurysm Treatment Device and Method"); 20110082491 (Sepetka et al., Apr. 7, 2011, "Devices and Methods for Treating Vascular Malformations"); 20110098814 (Monstadt et al., Apr. 28, 2011, "Medical Implant"); 20110137332 (Sepetka et al., Jun. 9, 2011, "Devices and Methods for Treating Vascular Malformations"); and 20110224776 (Sepetka et al., Sep. 15, 2011, "Devices and Methods for Treating Vascular Malformations").

Prior art which appears to be within this category also includes U.S. patent applications: 20120046676 (Morsi, Feb. 23, 2012, "Aneurysm Flow Barrier"); 20120071911 (Sadasivan et al., Mar. 22, 2012, "Spherical Helix Embolic Coils for the Treatment of Cerebral Aneurysms"); 20120283768 (Cox et al., Nov. 8, 2012, "Method and Apparatus for the Treatment of Large and Giant Vascular Defects"); 20120330341 (Becking et al., Dec. 27, 2012, "Folded-Flat Aneurysm Embolization Devices"); 20130089576 (Maitland et al., Apr. 11, 2013, "Implantable Embolic Scaffolds that Promote Healing"); 20130204289 (Dasnurkar et al., Aug. 8, 2013, "Devices and Methods for Occluding Vascular Abnormalities"); 20140012303 (Heipl, Jan. 9, 2014, "Braided Medical Device and Manufacturing Method Thereof"); 20140047694 (Monstadt et al., Feb. 20, 2014, "Medical Implant"); 20140135810 (Divino et al., May 15, 2014, "Occlusive Devices"); 20140135811 (Divino et al., May 15, 2014, "Occlusive Devices"); 20140135812 (Divino et al., May 15, 2014, "Occlusive Devices"); and 20140296358 (Maitland et al., Oct. 2, 2014, "Implantable Embolic Scaffolds That Promote Healing").

24. Embolic Coils with Relatively-Traditional Structures in Aneurysm Sac:

The prior art also includes some relatively-early embolic coils and also embolic coils with relatively-traditional structures which are implanted within an aneurysm sac. Some of these examples in the prior art represent early, pioneering use of embolic coils for occluding aneurysms. Some of these examples in the prior art use relatively-traditional embolic coils, but use them in novel ways or in novel combinations with other device components. Prior art which appears to be within this category includes U.S. Pat. No. 4,994,069 (Ritchart et al., Feb. 19, 1991, "Vaso-Occlusion Coil and Method"); U.S. Pat. No. 5,423,829 (Pham et al., Jun. 13, 1995, "Electrolytically Severable Joint for Endovascular Embolic Devices"); U.S. Pat. No. 5,624,449 (Pham et al., Apr. 29, 1997, "Electrolytically Severable Joint for Endovascular Embolic Devices"); U.S. Pat. No. 5,639,277 (Mariant et al., Jun. 17, 1997, "Embolic Coils with Offset Helical and Twisted Helical Shapes"); U.S. Pat. No. 5,690,666 (Berenstein et al., Nov. 25, 1997, "Ultrasoft Embolism Coils and Process for Using Them"); U.S. Pat. No. 5,718,711 (Berenstein et al., Feb. 17, 1998, "Ultrasoft Embolism Devices and Process for Using Them"); U.S. Pat. No. 5,743,905 (Eder et al., Apr. 28, 1998, "Partially Insulated Occlusion Device"); U.S. Pat. No. 5,749,894 (Engelson, May 12, 1998, "Aneurysm Closure Method"); U.S. Pat. No. 5,800,453 (Gia, Sep. 1, 1998, "Detachable Embolic Coil Assembly Using Interlocking Hooks and Slots"); U.S. Pat. No. 5,826,587 (Berenstein et al., Oct. 27, 1998, "Ultrasoft Embolism Coils and Process for Using Them"); and U.S. Pat. No. 5,916,235 (Guglielmi, Jun. 29, 1999, "Apparatus and Method for the Use of Detachable Coils in Vascular Aneurysms and Body Cavities").

Prior art which appears to be within this category also includes U.S. Pat. No. 6,024,754 (Engelson, Feb. 15, 2000, "Aneurysm Closure Method"); U.S. Pat. No. 6,099,546 (Gia, Aug. 8, 2000, "Detachable Embolic Coil Assembly Using Interlocking Hooks and Slots"); U.S. Pat. No. 6,123,714 (Gia et al., Sep. 26, 2000, "System for Detaching an Occlusive Device Within a Body Using a Solderless, Electrolytically Severable Joint"); U.S. Pat. No. 6,350,270 (Roue, Feb. 26, 2002, "Aneurysm Liner"); U.S. Pat. No. 6,409,721 (Wheelock et al., Jun. 25, 2002, "Process for Forming an Occlusion in a Body Cavity"); U.S. Pat. No. 6,458,119 (Berenstein et al., Oct. 1, 2002, "Ultrasoft Embolism Devices and Process for Using Them"); U.S. Pat. No. 6,585,748 (Jeffree, Jul. 1, 2003, "Device for Treating Aneurysms"); U.S. Pat. No. 6,589,230 (Gia et al., Jul. 8, 2003, "System for Detaching an Occlusive Device Within a Mammalian Body Using a Solderless, Electrolytically Severable Joint"); U.S. Pat. No. 6,855,153 (Saadat, Feb. 15, 2005, "Embolic Balloon"); U.S. Pat. No. 7,153,323 (Teoh et al., Dec. 26, 2006, "Aneurysm Liner with Multi-Segment Extender"); U.S. Pat. No. 7,238,194 (Monstadt et al., Jul. 3, 2007, "Device for Implanting Occlusion Spirals"); U.S. Pat. No. 7,294,137 (Rivelli et al., Nov. 13, 2007, "Device for Multi-Modal Treatment of Vascular Lesions"); U.S. Pat. No. 7,410,482 (Murphy et al., Aug. 12, 2008, "Detachable Aneurysm Neck Bridge"); and U.S. Pat. No. 7,691,124 (Balgobin, Apr. 6, 2010, "Delivery of Therapeutic Devices").

Prior art which appears to be within this category also includes U.S. Pat. No. 7,695,488 (Berenstein et al., Apr. 13, 2010, "Expandable Body Cavity Liner Device"); U.S. Pat. No. 7,708,754 (Balgobin et al., May 4, 2010, "Stretch Resistant Embolic Coil Delivery System with Mechanical Release Mechanism"); U.S. Pat. No. 7,713,264 (Murphy et al., May 11, 2010, "Detachable Aneurysm Neck Bridge"); U.S. Pat. No. 7,799,052 (Balgobin et al., Sep. 21, 2010, "Stretch Resistant Embolic Coil Delivery System with Mechanical Release Mechanism"); U.S. Pat. No. 7,811,305 (Balgobin et al., Oct. 12, 2010, "Stretch Resistant Embolic Coil Delivery System with Spring Release Mechanism"); U.S. Pat. No. 7,819,891 (Balgobin et al., Oct. 26, 2010, "Stretch Resistant Embolic Coil Delivery System with Spring Release Mechanism"); U.S. Pat. No. 7,819,892 (Balgobin et al., Oct. 26, 2010, "Embolic Coil Delivery System with Spring Wire Release Mechanism"); U.S. Pat. No. 7,985,238 (Balgobin et al., Jul. 26, 2011, "Embolic Coil Delivery System with Spring Wire Release Mechanism"); U.S. Pat. No. 8,021,416 (Abrams, Sep. 20, 2011, "Methods for Delivering a Prosthesis to a Site in a Body"); and U.S. Pat. No. 8,221,447 (Solar et al., Jul. 17, 2012, "Aneurysm Coil Delivery System").

Prior art which appears to be within this category also includes U.S. Pat. No. 8,267,923 (Murphy et al., Sep. 18, 2012, "Detachable Aneurysm Neck Bridge"); U.S. Pat. No. 8,361,106 (Solar et al., Jan. 29, 2013, "Aneurysm Coil Delivery System"); U.S. Pat. No. 8,372,062 (Murphy et al., Feb. 12, 2013, "Detachable Aneurysm Neck Bridge"); U.S. Pat. No. 8,425,542 (Moftakhar et al., Apr. 23, 2013, "Aneurysm Occlusion Device Containing Bioactive and Biocompatible Copolymer Shell and Biocompatible Metallic Frame Member"); U.S. Pat. No. 8,449,532 (Murphy et al., May 28, 2013, "Detachable Aneurysm Neck Bridge"); U.S. Pat. No. 8,529,556 (Murphy et al., Sep. 10, 2013, "Detachable Aneurysm Neck Bridge"); U.S. Pat. No. 8,529,619 (Abrams, Sep. 10, 2013, "Methods for Delivering a Prosthesis to a Site in a Body"); and U.S. Pat. No. 8,597,321 (Monstadt et al., Dec. 3, 2013, "Device for the Implantation of Occlusion Spirals").

Prior art which appears to be within this category also includes U.S. patent applications: 20030187473 (Berenstein et al., Oct. 2, 2003, "Expandable Body Cavity Liner Device"); 20040098027 (Teoh et al., May 20, 2004, "Expandable Body Cavity Liner Device"); 20070219578 (Solar et al., Sep. 20, 2007, "Aneurysm Coil Delivery System"); 20080281350 (Sepetka et al., Nov. 13, 2008, "Aneurysm Occlusion Devices"); 20090062834 (Moftakhar et al., Mar. 5, 2009, "Aneurysm Occlusion Device Containing Bioactive and Biocompatible Copolymer Shell and Biocompatible Metallic Frame Member"); 20100168781 (Berenstein et al., Jul. 1, 2010, "Expandable Body Cavity Liner Device"); 20100222804 (Murphy et al., Sep. 2, 2010, "Detachable Aneurysm Neck Bridge"); and 20110282378 (Murphy et al., Nov. 17, 2011, "Detachable Aneurysm Neck Bridge").

Prior art which appears to be within this category also includes U.S. patent applications: 20120283764 (Solar et al., Nov. 8, 2012, "Aneurysm Coil Delivery System"); 20120310270 (Murphy et al., Feb. 12, 2013, "Detachable Aneurysm Neck Bridge"); 20120310271 (Kwon, Dec. 6, 2012, "Embolus-Forming In-Vivo Indwelling Coil and Method for Manufacturing an Embolus-Forming In-Vivo Indwelling Coil"); 20130190800 (Murphy et al., Jul. 25, 2013, "Detachable Aneurysm Neck Bridge"); 20130261730 (Bose et al., Oct. 3, 2013, "Aneurysm Occlusion System and Method"); 20140081313 (Elliott, J., Mar. 20, 2014, "Embolic Coils and Related Components, Systems, and Methods"); and 20140180377 (Bose et al., Jun. 24, 2014, "Aneurysm Occlusion System and Method").

25. Embolic Coils with Complex Structures in Aneurysm Sac:

There are a large number of coil structures and configurations which are disclosed in the prior art. Some of these are not easily matched to a reasonable number of general device categories. Accordingly, this category is a general one for prior art which discloses coils with complex structures which do not fit well into other coil categories. Prior art which appears to be within this category includes U.S. Pat. No. 5,350,397 (Palermo et al., Sep. 27, 1994, "Axially Detachable Embolic Coil Assembly"); U.S. Pat. No. 5,382,259 (Phelps et al., Jan. 17, 1995, "Vasoocclusion Coil with Attached Tubular Woven or Braided Fibrous Covering"); U.S. Pat. No. 5,522,822 (Phelps et al., Jun. 4, 1996, "Vasoocclusion Coil with Attached Tubular Woven or Braided Fibrous Covering"); U.S. Pat. No. 5,582,619 (Ken, Dec. 10, 1996, "Stretch Resistant Vaso-Occlusive Coils"); U.S. Pat. No. 5,624,461 (Mariant, Apr. 29, 1997, "Three Dimensional In-Filling Vaso-Occlusive Coils"); U.S. Pat. No. 5,649,949 (Wallace et al., Jul. 22, 1997, "Variable Cross-Section Conical Vasoocclusive Coils"); U.S. Pat. No. 5,733,329 (Wallace et al., Mar. 31, 1998, "Vaso-Occlusive Coil with Conical End"); U.S. Pat. No. 5,749,891 (Ken et al., May 12, 1998, "Multiple Layered Vaso-Occlusive Coils"); U.S. Pat. No. 5,766,160 (Samson et al., Jun. 16, 1998, "Variable Stiffness Coils"); U.S. Pat. No. 5,800,455 (Palermo et al., Sep. 1, 1998, "Detachable Embolic Coil Assembly"); U.S. Pat. No. 5,833,705 (Ken et al., Nov. 10, 1998, "Stretch Resistant Vaso-Occlusive Coils"); U.S. Pat. No. 5,853,418 (Ken et al., Dec. 29, 1998, "Stretch Resistant Vaso-Occlusive Coils (II)"); U.S. Pat. No. 5,891,130 (Palermo et al., Apr. 6, 1999, "Axially Detachable Embolic Coil Assembly"); and U.S. Pat. No. 5,911,731 (Pham et al., Jun. 15, 1999, "Anatomically Shaped Vasoocclusive Devices").

Prior art which appears to be within this category also includes U.S. Pat. No. 5,925,059 (Palermo et al., Jul. 20, 1999, "Detachable Embolic Coil Assembly"); U.S. Pat. No. 5,941,888 (Wallace et al., Aug. 24, 1999, "Vaso-Occlusive Member Assembly with Multiple Detaching Points"); U.S. Pat. No. 5,957,948 (Mariant, Sep. 28, 1999, "Three Dimensional In-Filling Vaso-Occlusive Coils"); U.S. Pat. No. 5,980,514 (Kupiecki et al., Nov. 9, 1999, "Aneurysm Closure Device Assembly"); U.S. Pat. No. 6,004,338 (Ken et al., Dec. 21, 1999, "Stretch Resistant Vaso-Occlusive Coils"); U.S. Pat. No. 6,013,084 (Ken et al., Jan. 11, 2000, "Stretch Resistant Vaso-Occlusive Coils (II)"); U.S. Pat. No. 6,024,765 (Wallace et al., Feb. 15, 2000, "Vaso-Occlusive Coil with Conical End"); U.S. Pat. No. 6,033,423 (Ken et al., Mar. 7, 2000, "Multiple Layered Vaso-Occlusive Coils"); U.S. Pat. No. 6,096,034 (Kupiecki et al., Aug. 1, 2000, "Aneurysm Closure Device Assembly"); U.S. Pat. No. 6,143,007 (Mariant et al., Nov. 7, 2000, "Method for Making an Occlusive Device"); U.S. Pat. No. 6,159,165 (Ferrera et al., Dec. 12, 2000, "Three Dimensional Spherical Micro-Coils Manufactured from Radiopaque Nickel-Titanium Microstrand"); U.S. Pat. No. 6,168,592 (Kupiecki et al., Jan. 2, 2001, "Aneurysm Closure Device Assembly"); U.S. Pat. No. 6,187,027 (Mariant et al., Feb. 13, 2001, "Vaso-Occlusive Devices with Heat Secured Polymer Fiber"); and U.S. Pat. No. 6,193,728 (Ken et al., Feb. 27, 2001, "Stretch Resistant Vaso-Occlusive Coils (II)").

Prior art which appears to be within this category also includes U.S. Pat. No. 6,221,066 (Ferrera et al., Apr. 24, 2001, "Shape Memory Segmented Detachable Coil"); U.S. Pat. No. 6,231,586 (Mariant, May 15, 2001, "Three Dimensional In-Filling Vaso-Occlusive Coils"); U.S. Pat. No. 6,254,592 (Samson et al., Jul. 3, 2001, "Variable Stiffness Coils"); U.S. Pat. No. 6,280,457 (Wallace et al., Aug. 28, 2001, "Polymer Covered Vaso-Occlusive Devices and Methods of Producing Such Devices"); U.S. Pat. No. 6,344,041 (Kupiecki et al., Feb. 5, 2002, "Aneurysm Closure Device Assembly"); U.S. Pat. No. 6,371,972 (Wallace et al., Apr. 16, 2002, "Vaso-Occlusive Member Assembly with Multiple Detaching Points"); U.S. Pat. No. 6,533,801 (Wallace et al., Mar. 18, 2003, "Vaso-Occlusive Member Assembly with Multiple Detaching Points"); U.S. Pat. No. 6,551,305 (Ferrera et al., Apr. 22, 2003, "Shape Memory Segmented Detachable Coil"); U.S. Pat. No. 6,605,101 (Schaefer et al., Aug. 12, 2003, "Microcoil Vaso-Occlusive Device with Multi-Axis Secondary Configuration"); and U.S. Pat. No. 6,616,617 (Ferrera et al., Sep. 9, 2003, "Vasoocclusive Device for Treatment of Aneurysms").

Prior art which appears to be within this category also includes U.S. Pat. No. 6,623,493 (Wallace et al., Sep. 23, 2003, "Vaso-Occlusive Member Assembly with Multiple Detaching Points"); U.S. Pat. No. 6,660,020 (Wallace et al., Dec. 9, 2003, "Vaso-Occlusive Coil with Conical End"); U.S. Pat. No. 6,723,108 (Jones et al., Apr. 20, 2004, "Foam Matrix Embolization Device"); U.S. Pat. No. 6,979,344 (Jones et al., Dec. 27, 2005, "Foam Matrix Embolization Device"); U.S. Pat. No. 6,984,240 (Ken et al., Jan. 10, 2006, "Detachable Multidiameter Vasoocclusive Coil"); U.S. Pat. No. 7,029,486 (Schaefer et al., Apr. 18, 2006, "Microcoil Vaso-Occlusive Device with Multi-Axis Secondary Configuration"); U.S. Pat. No. 7,033,374 (Schaefer et al., Apr. 25, 2006, "Microcoil Vaso-Occlusive Device with Multi-Axis Secondary Configuration"); U.S. Pat. No. 7,326,225 (Ferrera et al., Feb. 5, 2008, "Vasoocclusive Device for Treatment of Aneurysms"); U.S. Pat. No. 7,331,974 (Schaefer et al., Feb. 19, 2008, "Microcoil Vaso-Occlusive Device with Multi-Axis Secondary Configuration"); U.S. Pat. No. 7,485,123 (Porter, Feb. 3, 2009, "Complex Vaso-Occlusive Coils"); and U.S. Pat. No. 7,695,484 (Wallace et al., Apr. 13, 2010, "Polymer Covered Vaso-Occlusive Devices and Methods of Producing Such Devices").

Prior art which appears to be within this category also includes U.S. Pat. No. 7,896,899 (Patterson et al., Mar. 1, 2011, "Metallic Coils Enlaced with Biological or Biodegradable or Synthetic Polymers or Fibers for Embolization of a Body Cavity"); U.S. Pat. No. 8,002,789 (Ramzipoor et al., Aug. 23, 2011, "Stretch-Resistant Vaso-Occlusive Devices with Flexible Detachment Junctions"); U.S. Pat. No. 8,066,036 (Monetti et al., Nov. 29, 2011, "Three-Dimensional Complex Coil"); U.S. Pat. No. 8,172,862 (Wallace et al., May 8, 2012, "Polymer Covered Vaso-Occlusive Devices and Methods of Producing Such Devices"); U.S. Pat. No. 8,202,292 (Kellett, Jun. 19, 2012, "Vaso-Occlusive Coil Delivery System"); U.S. Pat. No. 8,226,660 (Teoh et al., Jul. 24, 2012, "Vaso-Occlusive Coils with Non-Overlapping Sections"); U.S. Pat. No. 8,267,955 (Patterson et al., Sep. 18, 2012, "Metallic Coils Enlaced with Fibers for Embolization of a Body Cavity"); U.S. Pat. No. 8,308,751 (Gerberding, Nov. 13, 2012, "Foldable Vaso-Occlusive Member"); U.S. Pat. No. 8,323,306 (Schaefer et al., Dec. 4, 2012, "Microcoil Vaso-Occlusive Device with Multi-Axis Secondary Configuration"); U.S. Pat. No. 8,361,104 (Jones et al., Jan. 29, 2013, "Vascular Occlusion Device with an Embolic Mesh Ribbon"); and U.S. Pat. No. 8,444,668 (Jones et al., May 21, 2013, "Expandable Vascular Occlusion Device").

Prior art which appears to be within this category also includes U.S. patent applications: 20010009996 (Ferrera et al., Jul. 26, 2001, "Shape Memory Segmented Detachable Coil"); 20010056281 (Wallace et al., Dec. 27, 2001, "Vaso-Occlusive Member Assembly with Multiple Detaching Points"); 20020002382 (Wallace et al., Jan. 3, 2002, "Polymer Covered Vaso-Occlusive Devices and Methods of Producing Such Devices"); 20020058962 (Wallace et al., May 16, 2002, "Vaso-Occlusive Member Assembly with Multiple Detaching Points"); 20020107534 (Schaefer et al., Aug. 8, 2002, "Microcoil Vaso-Occlusive Device with Multi-Axis Secondary Configuration"); 20020128671 (Wallace et al., Sep. 12, 2002, "Polymer Covered Vaso-Occlusive Devices and Methods of Producing Such Devices"); 20020151926 (Wallace et al., Oct. 17, 2002, "Vasco-Occlusive Coil with Conical End"); 20030018356 (Schaefer et al., Jan. 23, 2003, "Microcoil Vaso-Occlusive Device with Multi-Axis Secondary Configuration"); and 20030130689 (Wallace et al., Jul. 10, 2003, "Vaso-Occlusive Member Assembly with Multiple Detaching Points").

Prior art which appears to be within this category also includes U.S. patent applications: 20040045554 (Schaefer et al., Mar. 11, 2004, "Microcoil Vaso-Occlusive Device with Multi-Axis Secondary Configuration"); 20040158282

(Jones et al., Aug. 12, 2004, "Foam Matrix Embolization Device"); 20040243168 (Ferrera et al., Dec. 2, 2004, "Vasoocclusive Device for Treatment of Aneurysms"); 20050033350 (Ken et al., Feb. 10, 2005, "Detachable Multidiameter Vasoocclusive Coil"); 20050192618 (Porter, Sep. 1, 2005, "Complex Vaso-Occlusive Coils"); 20050192621 (Wallace et al., Sep. 1, 2005, "Polymer Covered Vaso-Occlusive Devices and Methods of Producing Such Devices"); 20050277978 (Greenhalgh, Dec. 15, 2005, "Three-Dimensional Coils for Treatment of Vascular Aneurysms"); 20060036281 (Patterson; William R. et al., Feb. 16, 2006, "Metallic Coils Enlaced with Biological or Biodegradable or Synthetic Polymers or Fibers for Embolization of a Body Cavity"); and 20060184195 (Schaefer et al., Aug. 17, 2006, "Microcoil Vaso-Occlusive Device with Multi-Axis Secondary Configuration").

Prior art which appears to be within this category also includes U.S. patent applications: 20060184196 (Schaefer et al., Aug. 17, 2006, "Microcoil Vaso-Occlusive Device with Multi-Axis Secondary Configuration"); 20070016233 (Ferrera et al., Jan. 18, 2007, "Vasoocclusive Device for Treatment of Aneurysms"); 20070175536 (Monetti et al., Aug. 2, 2007, "Three-Dimensional Complex Coil"); 20080103585 (Monstadt et al., May 1, 2008, "Micro-Spiral Implantation Device"); 20090149864 (Porter, Jun. 11, 2009, "Complex Vaso-Occlusive Coils"); 20090254111 (Monstadt et al., Oct. 8, 2009, "Device for Implanting Occlusion Spirals Comprising an Interior Securing Element"); 20100036412 (Porter et al., Feb. 11, 2010, "Vaso-Occlusive Devices with Textured Surfaces"); 20100174301 (Wallace et al., Jul. 8, 2010, "Polymer Covered Vaso-Occlusive Devices and Methods of Producing Such Devices"); 20110092997 (Kang, Apr. 21, 2011, "Micro-Coil Assembly"); and 20110098814 (Monstadt et al., Apr. 28, 2011, "Medical Implant").

Prior art which appears to be within this category also includes U.S. patent applications: 20110118777 (Patterson et al., May 19, 2011, "Metallic Coils Enlaced with Fibers for Embolization of a Body Cavity"); 20110184454 (Barry et al., Jul. 28, 2011, "Embolic Implants"); 20110184455 (Keeley et al., Jul. 28, 2011, "Embolization Device Constructed from Expansile Polymer"); 20120089174 (Chen et al., Apr. 12, 2012, "Vaso-Occlusive Device"); 20120116441 (Yamanaka et al., May 10, 2012, "Embolization Coil"); 20120116442 (Monstadt et al., May 10, 2012, "Micro-Spiral Implantation Device"); 20120172921 (Yamanaka et al., Jul. 5, 2012, "Embolization Coil"); 20120209309 (Chen et al., Aug. 16, 2012, "Vaso-Occlusive Device"); 20120239074 (Aboytes et al., Sep. 20, 2012, "Devices and Methods for the Treatment of Vascular Defects"); 20120259354 (Kellett, Oct. 11, 2012, "Vaso-Occlusive Coil Delivery System"); 20130018409 (Le et al., Jan. 17, 2013, "Packing Coil"); and 20130066357 (Aboytes et al., Mar. 14, 2013, "Devices and Methods for the Treatment of Vascular Defects").

Prior art which appears to be within this category also includes U.S. patent applications: 20130116722 (Aboytes et al., May 9, 2013, "Devices and Methods for the Treatment of Vascular Defects"); 20130131711 (Bowman, May 23, 2013, "Embolic Device with Shaped Wire"); 20130253572 (Molaei et al., Sep. 26, 2013, "Occlusive Devices and Methods of Use"); 20140031858 (Bhagchandani et al., Jan. 30, 2014, "Systems and Methods for Delivering Multiple Embolization Coils"); 20140047694 (Monstadt et al., Feb. 20, 2014, "Medical Implant"); 20140128907 (Hui et al., May 8, 2014, "Occlusive Coil"); 20140163604 (Monstadt, Jun. 12, 2014, "Device for Implanting Electrically Isolated Occlusion Helixes"); 20140207180 (Ferrera, Jul. 24, 2014, "Systems and Devices for Cerebral Aneurysm Repair"); and 20140277100 (Kang, Sep. 18, 2014, "Micro-Coil Assembly").

26. Embolic Coils with Inter-Connecting Members in Aneurysm Sac:

The prior art also discloses devices and methods comprising embolic coils with inter-connecting members which are implanted within an aneurysm sac. In an example, a longitudinal coil can be inter-connected by relatively-inelastic strands at different locations along its longitudinal axis. Accordingly, the coil is constrained by these strands when it is deployed within the aneurysm sac and forms specific desired configurations which differ from those formed by an unconstrained coil. Prior art which appears to be within this category includes U.S. Pat. No. 5,443,478 (Purdy, Aug. 22, 1995, "Multi-Element Intravascular Occlusion Device"); U.S. Pat. No. 5,582,619 (Ken, Dec. 10, 1996, "Stretch Resistant Vaso-Occlusive Coils"); U.S. Pat. No. 5,766,219 (Horton, Jun. 16, 1998, "Anatomically Shaped Vasoocclusive Device and Method for Deploying Same"); U.S. Pat. No. 5,833,705 (Ken et al., Nov. 10, 1998, "Stretch Resistant Vaso-Occlusive Coils"); U.S. Pat. No. 5,853,418 (Ken et al., Dec. 29, 1998, "Stretch Resistant Vaso-Occlusive Coils (II)"); U.S. Pat. No. 5,935,145 (Villar et al., Aug. 10, 1999, "Vaso-Occlusive Device with Attached Polymeric Materials"); U.S. Pat. No. 6,004,338 (Ken et al., Dec. 21, 1999, "Stretch Resistant Vaso-Occlusive Coils"); U.S. Pat. No. 6,013,084 (Ken et al., Jan. 11, 2000, "Stretch Resistant Vaso-Occlusive Coils (II)"); and U.S. Pat. No. 6,193,728 (Ken et al., Feb. 27, 2001, "Stretch Resistant Vaso-Occlusive Coils (II)").

Prior art which appears to be within this category also includes U.S. Pat. No. 6,287,318 (Villar et al., Sep. 11, 2001, "Vaso-Occlusive Device with Attached Polymeric Materials"); U.S. Pat. No. 6,616,617 (Ferrera et al., Sep. 9, 2003, "Vasoocclusive Device for Treatment of Aneurysms"); U.S. Pat. No. 7,326,225 (Ferrera et al., Feb. 5, 2008, "Vasoocclusive Device for Treatment of Aneurysms"); U.S. Pat. No. 7,708,755 (Davis et al., May 4, 2010, "Stretch Resistant Embolic Coil Delivery System with Combined Mechanical and Pressure Release Mechanism"); U.S. Pat. No. 7,749,242 (Tran et al., Jul. 6, 2010, "Expanding Vaso-Occlusive Device"); U.S. Pat. No. 7,766,933 (Davis et al., Aug. 3, 2010, "Stretch Resistant Design for Embolic Coils with Stabilization Bead"); U.S. Pat. No. 7,883,526 (Jones et al., Feb. 8, 2011, "Embolic Coil Having Stretch Resistant Member with an Attached End and an End with Movement Freedom"); U.S. Pat. No. 7,896,899 (Patterson et al., Mar. 1, 2011, "Metallic Coils Enlaced with Biological or Biodegradable or Synthetic Polymers or Fibers for Embolization of a Body Cavity"); U.S. Pat. No. 7,938,845 (Aganon et al., May 10, 2011, "Anchor Assemblies in Stretch-Resistant Vaso-Occlusive Coils"); and U.S. Pat. No. 8,034,073 (Davis et al., Oct. 11, 2011, "Stretch Resistant Embolic Coil").

Prior art which appears to be within this category also includes U.S. Pat. No. 8,211,141 (Davis et al., Jul. 3, 2012, "Stretch Resistant Design for Embolic Coils with Stabilization Bead"); U.S. Pat. No. 8,267,955 (Patterson et al., Sep. 18, 2012, "Metallic Coils Enlaced with Fibers for Embolization of a Body Cavity"); U.S. Pat. No. 8,308,751 (Gerberding, Nov. 13, 2012, "Foldable Vaso-Occlusive Member"); U.S. Pat. No. 8,328,860 (Strauss et al., Dec. 11, 2012, "Implant Including a Coil and a Stretch-Resistant Member"); and U.S. Pat. No. 8,486,101 (Tran et al., Jul. 16, 2013, "Expanding Vaso-Occlusive Device").

Prior art which appears to be within this category also includes U.S. patent applications: 20060036281 (Patterson;

William R. et al., Feb. 16, 2006, "Metallic Coils Enlaced with Biological or Biodegradable or Synthetic Polymers or Fibers for Embolization of a Body Cavity"); 20070016233 (Ferrera et al., Jan. 18, 2007, "Vasoocclusive Device for Treatment of Aneurysms"); 20110118777 (Patterson et al., May 19, 2011, "Metallic Coils Enlaced with Fibers for Embolization of a Body Cavity"); 20110213406 (Aganon et al., Sep. 1, 2011, "Anchor Assemblies in Stretch-Resistant Vaso-Occlusive Coils"); 20110313443 (Lorenzo et al., Dec. 22, 2011, "Occlusive Device with Stretch Resistant Member and Anchor Filament"); and 20130331883 (Strauss et al., Dec. 12, 2013, "Implant Including a Coil and a Stretch-Resistant Member").

27. Embolic Coils with Special Coatings in Aneurysm Sac:

The prior art also discloses devices and methods for treating aneurysms which comprise embolic coils with special coatings for implantation within an aneurysm sac. Since this review focuses primarily on the mechanical and structural features of aneurysm treatment devices, this category focuses primarily on coil coatings which have special mechanical properties. There is a large body of prior art featuring stent and coil coatings with special pharmaceutical properties (apart from interesting mechanical properties) which are not included in this review.

Prior art which appears to be within this category includes U.S. Pat. No. 5,690,667 (Gia, Nov. 25, 1997, "Vasoocclusion Coil Having a Polymer Tip"); U.S. Pat. No. 5,702,361 (Evans et al., Dec. 30, 1997, "Method for Embolizing Blood Vessels"); U.S. Pat. No. 7,244,261 (Lorenzo et al., Jul. 17, 2007, "Activatable Bioactive Vascular Occlusive Device"); U.S. Pat. No. 7,247,159 (Lorenzo et al., Jul. 24, 2007, "Activatable Bioactive Vascular Occlusive Device"); U.S. Pat. No. 7,294,123 (Jones et al., Nov. 13, 2007, "Activatable Bioactive Vascular Occlusive Device and Method of Use"); U.S. Pat. No. 7,300,661 (Henson et al., Nov. 27, 2007, "Adding Microscopic Porosity to the Surface of a Microcoil to be Used for Medical Implantation"); U.S. Pat. No. 7,361,367 (Henson et al., Apr. 22, 2008, "Adding Microscopic Porosity to the Surface of a Microcoil to be Used for Medical Implantation"); U.S. Pat. No. 7,442,382 (Henson et al., Oct. 28, 2008, "Adding Microscopic Porosity to the Surface of a Microcoil to be Used for Medical Implantation"); U.S. Pat. No. 8,273,100 (Martinez, Sep. 25, 2012, "Three Element Coaxial Vaso-Occlusive Device"); and U.S. Pat. No. 8,764,788 (Martinez, Jul. 1, 2014, "Multi-Layer Coaxial Vaso-Occlusive Device").

Prior art which appears to be within this category also includes U.S. patent applications: 20030093111 (Ken et al., May 15, 2003, "Device for Vaso-Occlusion and Interventional Therapy"); 20040093014 (Ho et al., May 13, 2004, "Bioactive Components for Incorporation with Vaso-Occlusive Members"); 20040098028 (Martinez, May 20, 2004, "Three Element Coaxial Vaso-Occlusive Device"); 20050171572 (Martinez, Aug. 4, 2005, "Multi-Layer Coaxial Vaso-Occlusive Device"); 20060251695 (Henson et al., Nov. 9, 2006, "Adding Microscopic Porosity to the Surface of a Microcoil to be Used for Medical Implantation"); 20060251700 (Henson et al., Nov. 9, 2006, "Adding Microscopic Porosity to the Surface of a Microcoil to be Used for Medical Implantation"); 20080031919 (Henson et al., Feb. 7, 2008, "Adding Microscopic Porosity to the Surface of a Microcoil to be Used for Medical Implantation"); 20080152686 (Henson et al., Jun. 26, 2008, "Adding Microscopic Porosity to the Surface of a Microcoil to be Used for Medical Implantation"); 20110054511 (Henson et al., Mar. 3, 2011, "Adding Microscopic Porosity to the Surface of a Microcoil to be Used for Medical Implantation"); 20110245863 (Martinez, Oct. 6, 2011, "Multi-Layer Coaxial Vaso-Occlusive Device"); 20120323268 (Martinez, Dec. 20, 2012, "Three Element Coaxial Vaso-Occlusive Device"); 20130066359 (Murphy et al., Mar. 14, 2013, "Vaso-Occlusive Device"); and 20130072959 (Wu et al., Mar. 21, 2013, "Non-Fragmenting Low Friction Bioactive Absorbable Coils for Brain Aneurysm Therapy").

28. Polymer or Hydrogel Longitudinal Embolic Members in Aneurysm Sac:

The prior art also includes devices and methods comprising longitudinal embolic members (such as coils, filaments, or meshes) which are made from polymers or hydrogels and implanted within an aneurysm sac. These embolic members can be advantageously more flexible, more compressive, more expansive, and/or more bulky than metal embolic members. Prior art which appears to be within this category includes U.S. Pat. No. 5,749,894 (Engelson, May 12, 1998, "Aneurysm Closure Method"); U.S. Pat. No. 6,015,424 (Rosenbluth et al., Jan. 18, 2000, "Apparatus and Method for Vascular Embolization"); U.S. Pat. No. 6,024,754 (Engelson, Feb. 15, 2000, "Aneurysm Closure Method"); U.S. Pat. No. 6,312,421 (Boock, Nov. 6, 2001, "Aneurysm Embolization Material and Device"); U.S. Pat. No. 6,375,669 (Rosenbluth et al., Apr. 23, 2002, "Apparatus and Method for Vascular Embolization"); U.S. Pat. No. 6,423,085 (Murayama et al., Jul. 23, 2002, "Biodegradable Polymer Coils for Intraluminal Implants"); U.S. Pat. No. 6,602,269 (Wallace et al., Aug. 5, 2003, "Embolic Devices Capable of In-Situ Reinforcement"); and U.S. Pat. No. 6,723,108 (Jones et al., Apr. 20, 2004, "Foam Matrix Embolization Device").

Prior art which appears to be within this category also includes U.S. Pat. No. 6,979,344 (Jones et al., Dec. 27, 2005, "Foam Matrix Embolization Device"); U.S. Pat. No. 8,002,789 (Ramzipoor et al., Aug. 23, 2011, "Stretch-Resistant Vaso-Occlusive Devices with Flexible Detachment Junctions"); U.S. Pat. No. 8,273,100 (Martinez, Sep. 25, 2012, "Three Element Coaxial Vaso-Occlusive Device"); U.S. Pat. No. 8,313,504 (Do et al., Nov. 20, 2012, "Foam Matrix Embolization Device"); U.S. Pat. No. 8,377,091 (Cruise et al., Feb. 19, 2013, "Embolization Device Constructed from Expansile Polymer"); U.S. Pat. No. 8,470,035 (Cruise et al., Jun. 25, 2013, "Hydrogel Filaments for Biomedical Uses"); U.S. Pat. No. 8,764,788 (Martinez, Jul. 1, 2014, "Multi-Layer Coaxial Vaso-Occlusive Device"); and U.S. Pat. No. 8,771,294 (Sepetka et al., Jul. 8, 2014, "Aneurysm Treatment Devices and Methods").

Prior art which appears to be within this category also includes U.S. patent applications: 20020143348 (Wallace et al., Oct. 3, 2002, "Embolic Devices Capable of In-Situ Reinforcement"); 20040098028 (Martinez, May 20, 2004, "Three Element Coaxial Vaso-Occlusive Device"); 20040115164 (Pierce et al., Jun. 17, 2004, "Soft Filament Occlusive Device Delivery System"); 20040158282 (Jones et al., Aug. 12, 2004, "Foam Matrix Embolization Device"); 20040161451 (Pierce et al., Aug. 19, 2004, "Soft Filament Occlusive Device Delivery System"); and 20050119687 (Dacey et al., Jun. 2, 2005, "Methods of, and Materials for, Treating Vascular Defects with Magnetically Controllable Hydrogels").

Prior art which appears to be within this category also includes U.S. patent applications: 20050171572 (Martinez, Aug. 4, 2005, "Multi-Layer Coaxial Vaso-Occlusive Device"); 20060058834 (Do et al., Mar. 16, 2006, "Foam Matrix Embolization Device"); 20060116709 (Sepetka et al., Jun. 1, 2006, "Aneurysm Treatment Devices and Methods"); 20060116709 (Sepetka et al., Jun. 1, 2006, "Aneurysm Treatment Devices and Methods"); 20060116712

(Sepetka et al., Jun. 1, 2006, "Aneurysm Treatment Devices and Methods"); 20060116713 (Sepetka et al., Jun. 1, 2006, "Aneurysm Treatment Devices and Methods"); 20060276831 (Porter et al., Dec. 7, 2006, "Porous Materials for Use in Aneurysms"); 20070299464 (Cruise; Gregory M. et al., Dec. 27, 2007, "Embolization Device Constructed from Expansile Polymer"); 20080249608 (Dave, Oct. 9, 2008, "Bioabsorbable Polymer Bioabsorbable Composite Stents"); 20090164013 (Cruise et al., Jun. 25, 2009, "Hydrogel Filaments for Biomedical Uses"); and 20090227976 (Calabria et al., Sep. 10, 2009, "Multiple Biocompatible Polymeric Strand Aneurysm Embolization System and Method").

Prior art which appears to be within this category also includes U.S. patent applications: 20110184455 (Keeley et al., Jul. 28, 2011, "Embolization Device Constructed from Expansile Polymer"); 20110245863 (Martinez, Oct. 6, 2011, "Multi-Layer Coaxial Vaso-Occlusive Device"); 20120283769 (Cruise et al., Nov. 8, 2012, "Embolization Device Constructed from Expansile Polymer"); 20120289995 (Constant et al., Nov. 15, 2012, "Embolic Devices"); 20120323268 (Martinez, Dec. 20, 2012, "Three Element Coaxial Vaso-Occlusive Device"); 20130085518 (Trommeter et al., Apr. 4, 2013, "Multi-Fiber Shape Memory Device"); 20130131716 (Cruise et al., May 23, 2013, "Embolization Device Constructed from Expansile Polymer"); and 20130302251 (Constant et al., Nov. 14, 2013, "Embolic Devices").

29. Longitudinal Embolic Members with String-of-Pearls Structure in Aneurysm Sac:

The prior art also discloses devices and methods for treating aneurysms which comprise longitudinal embolic members with structure similar to a "string-of-pearls" for implantation within an aneurysm sac. In various examples, "string-of-pearls" structures can comprise an (evenly-spaced) series of wider (spherical, oblong, or rectangular) embolic members which are connected by a thinner (central) coil or string. Prior art which appears to be within this category includes U.S. Pat. No. 6,238,403 (Greene et al., May 29, 2001, "Filamentous Embolic Device with Expansible Elements"); U.S. Pat. No. 6,299,619 (Greene et al., Oct. 9, 2001, "Methods for Embolizing a Target Vascular Site"); U.S. Pat. No. 6,602,261 (Greene et al., Aug. 5, 2003, "Filamentous Embolic Device with Expansile Elements"); U.S. Pat. No. 6,616,617 (Ferrera et al., Sep. 9, 2003, "Vasoocclusive Device for Treatment of Aneurysms"); U.S. Pat. No. 7,014,645 (Greene et al., Mar. 21, 2006, "Method of Manufacturing Expansile Filamentous Embolization Devices"); U.S. Pat. No. 7,070,609 (West, Jul. 4, 2006, "Aneurysm Embolization Device and Deployment System"); U.S. Pat. No. 7,326,225 (Ferrera et al., Feb. 5, 2008, "Vasoocclusive Device for Treatment of Aneurysms"); U.S. Pat. No. 7,481,821 (Fogarty et al., Jan. 27, 2009, "Embolization Device and a Method of Using the Same"); U.S. Pat. No. 7,491,214 (Greene et al., Feb. 17, 2009, "Filamentous Embolization Device with Expansible Elements"); and U.S. Pat. No. 7,842,054 (Greene et al., Nov. 30, 2010, "Method of Manufacturing Expansile Filamentous Embolization Devices").

Prior art which appears to be within this category also includes U.S. Pat. No. 8,262,686 (Fogarty et al., Sep. 11, 2012, "Embolization Device and a Method of Using the Same"); U.S. Pat. No. 8,562,636 (Fogarty et al., Oct. 22, 2013, "Embolization Device and a Method of Using the Same"); U.S. Pat. No. 8,715,317 (Janardhan et al., May 6, 2014, "Flow Diverting Devices"); U.S. Pat. No. 8,747,432 (Janardhan et al., Jun. 10, 2014, "Woven Vascular Treatment Devices"); U.S. Pat. No. 8,753,371 (Janardhan et al., Jun. 17, 2014, "Woven Vascular Treatment Systems"); U.S. Pat. No. 8,771,294 (Sepetka et al., Jul. 8, 2014, "Aneurysm Treatment Devices and Methods"); U.S. Pat. No. 8,784,446 (Janardhan et al., Jul. 22, 2014, "Circumferentially Offset Variable Porosity Devices"); U.S. Pat. No. 8,813,625 (Janardhan et al., Aug. 26, 2014, "Methods of Manufacturing Variable Porosity Flow Diverting Devices"); and U.S. Pat. No. 8,845,679 (Janardhan et al., Sep. 30, 2014, "Variable Porosity Flow Diverting Devices").

Prior art which appears to be within this category also includes U.S. patent applications: 20020120276 (Greene et al., Aug. 29, 2002, "Filamentous Embolic Device with Expansile Elements"); 20020177855 (Greene et al., Nov. 28, 2002, "Method of Manufacturing Expansile Filamentous Embolization Devices"); 20040059370 (Greene et al., Mar. 25, 2004, "Filamentous Embolization Device with Expansible Elements"); 20040193246 (Ferrera, Sep. 30, 2004, "Methods and Apparatus for Treating Aneurysms and Other Vascular Defects"); 20040210249 (Fogarty et al., Oct. 21, 2004, "Embolization Device and a Method of Using the Same"); 20050015110 (Fogarty et al., Jan. 20, 2005, "Embolization Device and a Method of Using the Same"); and 20050267510 (Razack, Dec. 1, 2005, "Device for the Endovascular Treatment of Intracranial Aneurysms").

Prior art which appears to be within this category also includes U.S. patent applications: 20060116709 (Sepetka et al., Jun. 1, 2006, "Aneurysm Treatment Devices and Methods"); 20060116709 (Sepetka et al., Jun. 1, 2006, "Aneurysm Treatment Devices and Methods"); 20060116712 (Sepetka et al., Jun. 1, 2006, "Aneurysm Treatment Devices and Methods"); 20060116713 (Sepetka et al., Jun. 1, 2006, "Aneurysm Treatment Devices and Methods"); 20060149299 (Greene et al., Jul. 6, 2006, "Method of Manufacturing Expansile Filamentous Embolization Devices"); 20070016233 (Ferrera et al., Jan. 18, 2007, "Vasoocclusive Device for Treatment of Aneurysms"); 20070150045 (Ferrera, Jun. 28, 2007, "Methods and Apparatus for Treating Aneurysms and Other Vascular Defects"); 20090105748 (Fogarty et al., Apr. 23, 2009, "Embolization Device and a Method of Using the Same"); 20090232869 (Greene et al., Sep. 17, 2009, "Filamentous Embolization Device with Expansible Elements"); and 20120179192 (Fogarty et al., Jul. 12, 2012, "Embolization Device and a Method of Using the Same").

Prior art which appears to be within this category also includes U.S. patent applications: 20120239074 (Aboytes et al., Sep. 20, 2012, "Devices and Methods for the Treatment of Vascular Defects"); 20120303108 (Fogarty et al., Nov. 29, 2012, "Embolization Device and a Method of Using the Same"); 20130066357 (Aboytes et al., Mar. 14, 2013, "Devices and Methods for the Treatment of Vascular Defects"); 20130116722 (Aboytes et al., May 9, 2013, "Devices and Methods for the Treatment of Vascular Defects"); 20130231695 (Malek, Sep. 5, 2013, "Embolic Coil"); 20140088690 (Fogarty et al., Mar. 27, 2014, "Embolization Device and a Method of Using the Same"); 20140135810 (Divino et al., May 15, 2014, "Occlusive Devices"); 20140135811 (Divino et al., May 15, 2014, "Occlusive Devices"); 20140135812 (Divino et al., May 15, 2014, "Occlusive Devices"); 20140260928 (Janardhan et al., Sep. 18, 2014, "Methods of Using Non-Cylindrical Mandrels"); and 20140265096 (Janardhan et al., Sep. 18, 2014, "Non-Cylindrical Mandrels").

30. Accumulation of Mass in Aneurysm Sac by Spooling and/or Axial Rotation:

Although not common, the prior art also includes a few examples of devices and methods for treating aneurysms comprising accumulating embolic mass in the aneurysm sac by the rotational spooling or dispensation of a longitudinal embolic member within the aneurysm sac. In an example, the accumulation of mass can occur as a longitudinal embolic member is spooled around a rotating central member within the sac. In an example, the accumulation of mass can occur as a longitudinal embolic member is dispensed within the sac from a rotating central member. Prior art which appears to be within this category includes U.S. patent applications 20110166588 (Connor et al., Jul. 7, 2011, "Aneurysm Embolization by Rotational Accumulation of Mass") and 20120303052 (Connor, Nov. 29, 2012, "Aneurysm Occlusion by Rotational Dispensation of Mass").

31. Liner or Balloon with Non-Porous Walls in Aneurysm Sac:

The prior art also discloses devices and methods for treating aneurysms including the use of a flexible occluding intrasacular aneurysm liner or balloon which has non-porous walls and which is deployed within the aneurysm sac. Such a flexible liner or balloon can be filled with solid embolic members, a gelatinous embolic composition, or a liquid embolic composition—which can contribute to its expansion within the aneurysm sac. Prior art which appears to be within this category includes U.S. Pat. No. 5,334,210 (Gianturco, Aug. 2, 1994, "Vascular Occlusion Assembly"); U.S. Pat. No. 6,350,270 (Roue, Feb. 26, 2002, "Aneurysm Liner"); U.S. Pat. No. 6,511,468 (Cragg et al., Jan. 28, 2003, "Device and Method for Controlling Injection of Liquid Embolic Composition"); U.S. Pat. No. 7,338,511 (Mirigian et al., Mar. 4, 2008, "Solid Embolic Material with Variable Expansion"); U.S. Pat. No. 7,695,488 (Berenstein et al., Apr. 13, 2010, "Expandable Body Cavity Liner Device"); U.S. Pat. No. 7,976,527 (Cragg et al., Jul. 12, 2011, "Device and Method for Controlling Injection of Liquid Embolic Composition"); U.S. Pat. No. 8,021,416 (Abrams, Sep. 20, 2011, "Methods for Delivering a Prosthesis to a Site in a Body"); U.S. Pat. No. 8,425,541 (Masters et al., Apr. 23, 2013, "Aneurysm Occlusion Device Containing Bioactive and Biocompatible Copolymer Shell and a Liquid Embolic Agent"); U.S. Pat. No. 8,425,542 (Moftakhar et al., Apr. 23, 2013, "Aneurysm Occlusion Device Containing Bioactive and Biocompatible Copolymer Shell and Biocompatible Metallic Frame Member"); U.S. Pat. No. 8,454,649 (Cragg et al., Jun. 4, 2013, "Device and Method for Controlling Injection of Liquid Embolic Composition"); and U.S. Pat. No. 8,529,619 (Abrams, Sep. 10, 2013, "Methods for Delivering a Prosthesis to a Site in a Body").

Prior art which appears to be within this category also includes U.S. patent applications: 20030187473 (Berenstein et al., Oct. 2, 2003, "Expandable Body Cavity Liner Device"); 20090062834 (Moftakhar et al., Mar. 5, 2009, "Aneurysm Occlusion Device Containing Bioactive and Biocompatible Copolymer Shell and Biocompatible Metallic Frame Member"); 20090118761 (Masters et al., May 7, 2009, "Aneurysm Occlusion Device Containing Bioactive and Biocompatible Copolymer Shell and a Liquid Embolic Agent"); 20100168781 (Berenstein et al., Jul. 1, 2010, "Expandable Body Cavity Liner Device"); 20130211443 (Cragg et al., Aug. 15, 2013, "Device and Method for Controlling Injection of Liquid Embolic Composition"); and 20140039536 (Cully et al., Feb. 6, 2014, "Space-Filling Device").

32. Liner, Balloon, Net, or Mesh with Porous Walls in Aneurysm Sac:

The prior art also includes devices and methods for treating aneurysms comprising a flexible occluding intrasacular aneurysm liner, balloon, net, or mesh with relatively-porous walls which is deployed within the aneurysm sac. Such a flexible liner, balloon, net, or mesh can be filled with solid embolic members or compositions, which can contribute to its expansion within the aneurysm sac. In an example, the walls of an aneurysm liner, balloon, net, or mesh can be permeable to inflow of blood from the sac or to outflow from liquid (e.g. saline or contrast media) which is injected within it, but be impermeable to outflow of embolic members. Prior art which appears to be within this category includes U.S. Pat. No. 4,364,392 (Strother et al., Dec. 21, 1982, "Detachable Balloon Catheter"); U.S. Pat. No. 6,346,117 (Greenhalgh, Feb. 12, 2002, "Bag for Use in the Intravascular Treatment of Saccular Aneurysms"); U.S. Pat. No. 6,391,037 (Greenhalgh, May 21, 2002, "Bag for Use in the Intravascular Treatment of Saccular Aneurysms"); U.S. Pat. No. 6,547,804 (Porter et al., Apr. 15, 2003, "Selectively Permeable Highly Distensible Occlusion Balloon"); U.S. Pat. No. 6,585,748 (Jeffree, Jul. 1, 2003, "Device for Treating Aneurysms"); U.S. Pat. No. 6,855,153 (Saadat, Feb. 15, 2005, "Embolic Balloon"); U.S. Pat. No. 7,153,323 (Teoh et al., Dec. 26, 2006, "Aneurysm Liner with Multi-Segment Extender"); U.S. Pat. No. 7,695,488 (Berenstein et al., Apr. 13, 2010, "Expandable Body Cavity Liner Device"); U.S. Pat. No. 8,021,416 (Abrams, Sep. 20, 2011, "Methods for Delivering a Prosthesis to a Site in a Body"); and U.S. Pat. No. 8,529,619 (Abrams, Sep. 10, 2013, "Methods for Delivering a Prosthesis to a Site in a Body").

Prior art which appears to be within this category also includes U.S. patent applications: 20030187473 (Berenstein et al., Oct. 2, 2003, "Expandable Body Cavity Liner Device"); 20040098027 (Teoh et al., May 20, 2004, "Expandable Body Cavity Liner Device"); 20060079923 (Chhabra et al., Apr. 13, 2006, "Aneurysm Treatment Using Semi-Compliant Balloon"); 20090112249 (Miles et al., Apr. 30, 2009, "Medical Device for Modification of Left Atrial Appendage and Related Systems and Methods"); 20100168781 (Berenstein et al., Jul. 1, 2010, "Expandable Body Cavity Liner Device"); 20110046658 (Connor et al., Feb. 24, 2011, "Aneurysm Occlusion Device"); 20140135810 (Divino et al., May 15, 2014, "Occlusive Devices"); 20140135811 (Divino et al., May 15, 2014, "Occlusive Devices"); and 20140135812 (Divino et al., May 15, 2014, "Occlusive Devices"); and also PCT/US2009/002537 (Connor et al, 2009, "Aneurysm Occlusion Device").

33. Liquid Embolic Composition into Aneurysm Sac:

The prior art also discloses devices and methods for treating aneurysms comprising injection of a liquid embolic composition into an aneurysm sac. Most of the time, unless contained within a liner or balloon, this liquid embolic composition is formulated to congeal within the sac. Often this congealing process is accelerated by the concurrent delivery of a congealing agent or energy. Sometimes a balloon is temporarily expanded within the parent vessel to prevent the liquid embolic composition from leaking out of the aneurysm sac before it congeals. Prior art which appears to be within this category includes U.S. Pat. No. 5,776,097 (Massoud, Jul. 7, 1998, "Method and Device for Treating Intracranial Vascular Aneurysms"); U.S. Pat. No. 5,785,679 (Abolfathi et al., Jul. 28, 1998, "Methods and Apparatus for Treating Aneurysms and Arterio-Venous Fistulas"); U.S. Pat. No. 5,795,331 (Cragg et al., Aug. 18, 1998, "Balloon Catheter for Occluding Aneurysms of Branch Vessels"); U.S. Pat. No. 6,096,021 (Helm et al., Aug. 1, 2000, "Flow Arrest, Double Balloon Technique for Occluding Aneurysms or Blood Vessels"); U.S. Pat. No. 6,140,452 (Felt et al., Oct. 31, 2000, "Biomaterial for In Situ Tissue Repair"); U.S. Pat. No. 6,306,177 (Felt et al., Oct. 23, 2001, "Biomaterial System for In Situ Tissue Repair"); U.S. Pat. No. 6,454,738 (Tran et al., Sep. 24, 2002, "Methods for Delivering In Vivo Uniform Dispersed Embolic Compositions of High Viscosity"); and U.S. Pat. No. 6,511,468 (Cragg et al., Jan. 28, 2003, "Device and Method for Controlling Injection of Liquid Embolic Composition").

Prior art which appears to be within this category also includes U.S. Pat. No. 6,547,804 (Porter et al., Apr. 15, 2003, "Selectively Permeable Highly Distensible Occlusion Balloon"); U.S. Pat. No. 6,569,190 (Whalen et al., May 27, 2003, "Methods for Treating Aneurysms"); U.S. Pat. No. 6,629,947 (Sahatjian et al., Oct. 7, 2003, "Systems and Methods for Delivering Flowable Substances for Use as Implants and Surgical Sealants"); U.S. Pat. No. 6,958,061 (Truckai et al., Oct. 25, 2005, "Microspheres with Sacrificial Coatings for Vaso-Occlusive Systems"); U.S. Pat. No. 6,964,657 (Cragg et al., Nov. 15, 2005, "Catheter System and Method for Injection of a Liquid Embolic Composition and a Solidification Agent"); U.S. Pat. No. 7,083,632 (Avellanet et al., Aug. 1, 2006, "Aneurysm Embolic Device with an Occlusive Member"); U.S. Pat. No. 7,083,643 (Whalen et al., Aug. 1, 2006, "Methods for Treating Aneurysms"); and U.S. Pat. No. 7,294,137 (Rivelli et al., Nov. 13, 2007, "Device for Multi-Modal Treatment of Vascular Lesions").

Prior art which appears to be within this category also includes U.S. Pat. No. 7,338,511 (Mirigian et al., Mar. 4, 2008, "Solid Embolic Material with Variable Expansion"); U.S. Pat. No. 7,374,568 (Whalen et al., May 20, 2008, "Methods for Embolizing Aneurysmal Sites with a High Viscosity Embolizing Composition"); U.S. Pat. No. 7,414,038 (Kinugasa et al., Aug. 19, 2008, "Embolic Materials"); U.S. Pat. No. 7,666,220 (Evans et al., Feb. 23, 2010, "System and Methods for Endovascular Aneurysm Treatment"); U.S. Pat. No. 7,976,527 (Cragg et al., Jul. 12, 2011, "Device and Method for Controlling Injection of Liquid Embolic Composition"); U.S. Pat. No. 8,262,607 (Porter, Sep. 11, 2012, "Liquid Embolic Composition Delivery Devices and Methods"); U.S. Pat. No. 8,425,541 (Masters et al., Apr. 23, 2013, "Aneurysm Occlusion Device Containing Bioactive and Biocompatible Copolymer Shell and a Liquid Embolic Agent"); and U.S. Pat. No. 8,454,649 (Cragg et al., Jun. 4, 2013, "Device and Method for Controlling Injection of Liquid Embolic Composition").

Prior art which appears to be within this category also includes U.S. patent applications: 20020018752 (Krall et al., Feb. 14, 2002, "Polymerizable Compositions and Methods of Use"); 20020082620 (Lee, Jun. 27, 2002, "Bioactive Materials for Aneurysm Repair"); 20030093097 (Avellanet et al., May 15, 2003, "Aneurysm Embolic Device with an Occlusive Member"); 20030135264 (Whalen et al., Jul. 17, 2003, "Methods for Treating Aneurysms"); 20030223955 (Whalen et al., Dec. 4, 2003, "Methods for Embolizing Aneurysmal Sites with a High Viscosity Embolizing Composition"); 20040098027 (Teoh et al., May 20, 2004, "Expandable Body Cavity Liner Device"); 20060235464 (Avellanet et al., Oct. 19, 2006, "Aneurysm Embolic Device with an Occlusive Member"); and 20090118761 (Masters et al., May 7, 2009, "Aneurysm Occlusion Device Containing Bioactive and Biocompatible Copolymer Shell and a Liquid Embolic Agent").

Prior art which appears to be within this category also includes U.S. patent applications: 20090318949 (Ganpath et al., Dec. 24, 2009, "Sealing Apparatus and Methods of Use"); 20130108574 (Chevalier et al., May 2, 2013, "Radiopaque, Non-Biodegradable, Water-Insoluble Iodinated Benzyl Ethers of Poly(Vinyl Alcohol), Preparation Method Thereof, Injectable Embolizing Compositions Containing Thereof and Use Thereof"); 20130211443 (Cragg et al., Aug. 15, 2013, "Device and Method for Controlling Injection of Liquid Embolic Composition"); and 20130310687 (Takizawa et al., Nov. 21, 2013, "Blood Vessel Embolization Method Using Balloon Catheter and Balloon Catheter for Blood Vessel Embolization Method").

34. Gelatinous Embolic Composition into Aneurysm Sac:

The prior art also discloses devices and methods for treating aneurysms comprising injection of a gelatinous embolic composition into an aneurysm sac. Often, this gelatinous embolic composition is formulated to further solidify within the aneurysm sac. Sometimes this solidification process is accelerated by the concurrent delivery of a solidifying agent or energy. Prior art which appears to be within this category includes U.S. Pat. No. 5,624,685 (Takahashi et al., Apr. 29, 1997, "High Polymer Gel and Vascular Lesion Embolizing Material Comprising the Same"); U.S. Pat. No. 5,702,361 (Evans et al., Dec. 30, 1997, "Method for Embolizing Blood Vessels"); U.S. Pat. No. 5,749,894 (Engelson, May 12, 1998, "Aneurysm Closure Method"); U.S. Pat. No. 5,888,546 (Ji et al., Mar. 30, 1999, "Embolic Material for Endovascular Occlusion of Abnormal Vasculature and Method for Using the Same"); U.S. Pat. No. 5,894,022 (Ji et al., Apr. 13, 1999, "Embolic Material for Endovascular Occlusion of Abnormal Vasculature and Method of Using the Same"); U.S. Pat. No. 6,017,977 (Evans et al., Jan. 25, 2000, "Methods for Embolizing Blood Vessels"); U.S. Pat. No. 6,024,754 (Engelson, Feb. 15, 2000, "Aneurysm Closure Method"); and U.S. Pat. No. 6,238,403 (Greene et al., May 29, 2001, "Filamentous Embolic Device with Expansible Elements").

Prior art which appears to be within this category also includes U.S. Pat. No. 6,281,263 (Evans et al., Aug. 28, 2001, "Methods for Embolizing Blood Vessels"); U.S. Pat. No. 6,299,619 (Greene et al., Oct. 9, 2001, "Methods for Embolizing a Target Vascular Site"); U.S. Pat. No. 6,335,384 (Evans et al., Jan. 1, 2002, "Methods for Embolizing Blood Vessels"); U.S. Pat. No. 6,379,373 (Sawhney et al., Apr. 30, 2002, "Methods and Apparatus for Intraluminal Deposition of Hydrogels"); U.S. Pat. No. 6,463,317 (Kucharczyk et al., Oct. 8, 2002, "Device and Method for the Endovascular Treatment of Aneurysms"); U.S. Pat. No. 6,602,261 (Greene et al., Aug. 5, 2003, "Filamentous Embolic Device with Expansile Elements"); U.S. Pat. No. 6,689,148 (Sawhney et al., Feb. 10, 2004, "Methods and Apparatus for Intraluminal Deposition of Hydrogels"); U.S. Pat. No. 6,818,018 (Sawhney, Nov. 16, 2004, "In Situ Polymerizable Hydrogels"); and U.S. Pat. No. 7,014,645 (Greene et al., Mar. 21, 2006, "Method of Manufacturing Expansile Filamentous Embolization Devices").

Prior art which appears to be within this category also includes U.S. Pat. No. 7,220,270 (Sawhney et al., May 22, 2007, "Methods and Apparatus for Intraluminal Deposition of Hydrogels"); U.S. Pat. No. 7,491,214 (Greene et al., Feb. 17, 2009, "Filamentous Embolization Device with Expansible Elements"); U.S. Pat. No. 7,842,054 (Greene et al., Nov. 30, 2010, "Method of Manufacturing Expansile Filamentous Embolization Devices"); U.S. Pat. No. 8,439,942 (Moran et al., May 14, 2013, "Embolization Device"); U.S. Pat. No. 8,535,367 (Kim et al., Sep. 17, 2013, "Devices and Methods for Treatment of Vascular Aneurysms"); U.S. Pat. No. 8,647,377 (Kim et al., Feb. 11, 2014, "Devices and Methods for Treatment of Vascular Aneurysms"); and U.S. Pat. No. 8,840,867 (Sophie et al., Sep. 23, 2014, "Embolizing Sclerosing Hydrogel").

Prior art which appears to be within this category also includes U.S. patent applications: 20020082636 (Sawhney et al., Jun. 27, 2002, "Methods and Apparatus for Intraluminal Deposition of Hydrogels"); 20020120276 (Greene et al., Aug. 29, 2002, "Filamentous Embolic Device with Expansile Elements"); 20020177855 (Greene et al., Nov. 28, 2002, "Method of Manufacturing Expansile Filamentous Embolization Devices"); 20030014075 (Rosenbluth et al., Jan. 16, 2003, "Methods, Materials and Apparatus for Deterring or Preventing Endoleaks Following Endovascular Graft Implantation"); 20040059370 (Greene et al., Mar. 25, 2004, "Filamentous Embolization Device with Expansible Elements"); 20050004660 (Rosenbluth et al., Jan. 6, 2005, "Methods, Materials and Apparatus for Deterring or Preventing Endoleaks Following Endovascular Graft Implantation"); 20050080445 (Sawhney et al., Apr. 14, 2005, "Methods and Apparatus for Intraluminal Deposition of Hydrogels"); and 20050133046 (Becker et al., Jun. 23, 2005, "Compositions and Methods for Improved Occlusion of Vascular Defects").

Prior art which appears to be within this category also includes U.S. patent applications: 20060149299 (Greene et al., Jul. 6, 2006, "Method of Manufacturing Expansile Filamentous Embolization Devices"); 20060292206 (Kim et al., Dec. 28, 2006, "Devices and Methods for Treatment of Vascular Aneurysms"); 20070050008 (Kim et al., Mar. 1, 2007, "Devices and Methods for Treatment of Vascular Aneurysms"); 20070055355 (Kim et al., Mar. 8, 2007, "Devices and Methods for Treatment of Vascular Aneurysms"); 20070061005 (Kim et al., Mar. 15, 2007, "Devices and Methods for Treatment of Vascular Aneurysms"); 20070150041 (Evans et al., Jun. 28, 2007, "Methods and Systems for Aneurysm Treatment Using Filling Structures"); and 20070167747 (Borgert et al., Jul. 19, 2007, "Catheter, Apparatus and Method for Therapeutic Embolization").

Prior art which appears to be within this category also includes U.S. patent applications: 20090232869 (Greene et al., Sep. 17, 2009, "Filamentous Embolization Device with Expansible Elements"); 20100063472 (Becker et al., Mar. 11, 2010, "Compositions and Methods for Improved Occlusion of Vascular Defects"); 20110182998 (Reb et al., Jul. 28, 2011, "Microspheres Useful for Therapeutic Vascular Embolization"); 20110286925 (Lerouge et al., Nov. 24, 2011, "Embolizing Sclerosing Hydrogel"); 20120238644 (Gong et al., Sep. 20, 2012, "Fragmented Hydrogels"); 20120265287 (Sharma et al., Oct. 18, 2012, "In-Situ Forming Foams for Treatment of Aneurysms"); 20120330343 (Kim et al., Dec. 27, 2012, "Devices and Methods for Treatment of Vascular Aneurysms"); and 20130045182 (Gong et al., Feb. 21, 2013, "Polysaccharide Based Hydrogels").

Prior art which appears to be within this category also includes U.S. patent applications: 20130095087 (Shalaby et al., Apr. 18, 2013, "Absorbable In Situ Gel-Forming System, Method of Making and Use Thereof"); 20130131711 (Bowman, May 23, 2013, "Embolic Device with Shaped Wire"); 20130245606 (Stam et al., Sep. 19, 2013, "Hydrogel Based Occlusion Systems"); 20130252900 (Reb et al., Sep. 26, 2013, "Microspheres Useful for Therapeutic Vascular Embolization"); 20130344159 (Moine et al., Dec. 26, 2013, "Implantable Swellable Bio-Resorbable Polymer"); 20140052168 (Sawhney, Feb. 20, 2014, "Methods of Using In Situ Hydration of Hydrogel Articles for Sealing or Augmentation of Tissue or Vessels"); and 20140081374 (Kim et al., Mar. 20, 2014, "Devices and Methods for Treatment of Vascular Aneurysms").

35. Embolic Spheres and/or Particles into Aneurysm Sac:

The prior art also includes devices and methods for treating aneurysms which comprise the delivery of a plurality of separate embolic spherical, polygonal, and/or other generally-convex shaped members into the sac of an aneurysm. These spheres, polygons, and/or other convex particles can be inserted into an aneurysm liner, net, or mesh which helps to contain them within the sac. These spheres, polygons, and/or other convex embolic members can be soft or hard, compressible or resilient, solid or hollow. Expandable intrasacular woven wire devices (e.g. ball-shaped stents) are included in a different category. Prior art which appears to be within this category includes U.S. Pat. No. 4,364,392 (Strother et al., Dec. 21, 1982, "Detachable Balloon Catheter"); U.S. Pat. No. 6,958,061 (Truckai et al., Oct. 25, 2005, "Microspheres with Sacrificial Coatings for Vaso-Occlusive Systems"); U.S. Pat. No. 7,311,861 (Lanphere et al., Dec. 25, 2007, "Embolization"); U.S. Pat. No. 7,449,236 (Lanphere et al., Nov. 11, 2008, "Porous Polymeric Particle Comprising Polyvinyl Alcohol and Having Interior to Surface Porosity-Gradient"); U.S. Pat. No. 7,588,780 (Buiser et al., Sep. 15, 2009, "Embolization"); U.S. Pat. No. 7,588,825 (Bell et al., Sep. 15, 2009, "Embolic Compositions"); U.S. Pat. No. 7,666,333 (Lanphere et al., Feb. 23, 2010, "Embolization"); U.S. Pat. No. 7,695,488 (Berenstein et al., Apr. 13, 2010, "Expandable Body Cavity Liner Device"); U.S. Pat. No. 7,736,671 (DiCarlo et al., Jun. 15, 2010, "Embolization"); U.S. Pat. No. 7,842,377 (Lanphere et al., Nov. 30, 2010, "Porous Polymeric Particle Comprising Polyvinyl Alcohol and Having Interior to Surface Porosity-Gradient"); U.S. Pat. No. 7,976,823 (Lanphere et al., Jul. 12, 2011, "Ferromagnetic Particles and Methods"); and U.S. Pat. No. 8,617,132 (Golzarian et al., Dec. 31, 2013, "Bioresorbable Embolization Microspheres").

Prior art which appears to be within this category also includes U.S. patent applications: 20030187473 (Berenstein et al., Oct. 2, 2003, "Expandable Body Cavity Liner Device"); 20040091543 (Bell et al., May 13, 2004, "Embolic Compositions"); 20040098027 (Teoh et al., May 20, 2004, "Expandable Body Cavity Liner Device"); 20060276831 (Porter et al., Dec. 7, 2006, "Porous Materials for Use in Aneurysms"); 20080033366 (Matson et al., Feb. 7, 2008, "Compressible Intravascular Embolization Particles and Related Methods and Delivery Systems"); 20090112249 (Miles et al., Apr. 30, 2009, "Medical Device for Modification of Left Atrial Appendage and Related Systems and Methods"); 20090318948 (Linder et al., Dec. 24, 2009, "Device, System and Method for Aneurysm Embolization"); and 20100168781 (Berenstein et al., Jul. 1, 2010, "Expandable Body Cavity Liner Device").

Prior art which appears to be within this category also includes U.S. patent applications: a20110046658 (Connor et al., Feb. 24, 2011, "Aneurysm Occlusion Device"); 20110082427 (Golzarian et al., Apr. 7, 2011, "Bioresorbable Embolization Microspheres"); 20110182998 (Reb et al., Jul. 28, 2011, "Microspheres Useful for Therapeutic Vascular Embolization"); 20130190795 (Matson et al., Jul. 25, 2013, "Compressible Intravascular Embolization Particles and Related Methods and Delivery Systems"); 20130252900 (Reb et al., Sep. 26, 2013, "Microspheres Useful for Therapeutic Vascular Embolization"); 20140099374 (Golzarian et al., Apr. 10, 2014, "Bioresorbable Embolization Microspheres"); 20140135810 (Divino et al., May 15, 2014, "Occlusive Devices"); 20140135811 (Divino et al., May 15, 2014, "Occlusive Devices"); and 20140135812 (Divino et al., May 15, 2014, "Occlusive Devices"); and also PCT/US2009/002537 (Connor et al, 2009, "Aneurysm Occlusion Device").

36. Customized Pre-Molded Member into Aneurysm Sac:

The prior art also discloses devices and methods for treating aneurysms which comprise customized (e.g. pre-molded or pre-shaped) occlusion devices which are specifically configured to match the configuration of a specific aneurysm (in a specific patient). Such customized occlusion devices are often designed based on the results of three-dimensional imaging of the aneurysm. Prior art which appears to be within this category includes U.S. Pat. No. 6,165,193 (Greene et al., Dec. 26, 2000, "Vascular Embolization with an Expansible Implant"); U.S. Pat. No. 6,165,193 (Greene et al., Dec. 26, 2000, "Vascular Embolization with an Expansible Implant"); U.S. Pat. No. 6,500,190 (Greene et al., Dec. 31, 2002, "Vascular Embolization with an Expansible Implant"); U.S. Pat. No. 7,029,487 (Greene et al., Apr. 18, 2006, "Vascular Embolization with an Expansible Implant"); U.S. Pat. No. 7,201,762 (Greene et al., Apr. 10, 2007, "Vascular Embolization with an Expansible Implant"); and U.S. Pat. No. 7,483,558 (Greene et al., Jan. 27, 2009, "Vascular Embolization with an Expansible Implant").

Prior art which appears to be within this category also includes U.S. Pat. No. 7,799,047 (Greene et al., Sep. 21, 2010, "Vascular Embolization with an Expansible Implant"); U.S. Pat. No. 8,067,071 (Farnsworth et al., Nov. 29, 2011, "Composite Self-Cohered Web Materials"); U.S. Pat. No. 8,133,256 (Wilson et al., Mar. 13, 2012, "Shape Memory Polymer Foams for Endovascular Therapies"); U.S. Pat. No. 8,377,241 (Farnsworth et al., Feb. 19, 2013, "Method of Making Porous Self-Cohered Web Materials"); U.S. Pat. No. 8,449,592 (Wilson et al., May 28, 2013, "Stent with Expandable Foam"); U.S. Pat. No. 8,473,030 (Greenan et al., Jun. 25, 2013, "Vessel Position and Configuration Imaging Apparatus and Methods"); and U.S. Pat. No. 8,597,745 (Farnsworth et al., Dec. 3, 2013, "Composite Self-Cohered Web Materials").

Prior art which appears to be within this category also includes U.S. patent applications: 20010001835 (Greene et al., May 24, 2001, "Vascular Embolization with an Expansible Implant"); 20030083737 (Greene et al., May 1, 2003, "Vascular Embolization with an Expansible Implant"); 20030088311 (Greene et al., May 8, 2003, "Vascular Embolization with an Expansible Implant"); 20050075405 (Wilson et al., Apr. 7, 2005, "Shape Memory Polymer Foams for Endovascular Therapies"); 20050095428 (Dicarlo et al., May 5, 2005, "Embolic Compositions"); 20060036045 (Wilson et al., Feb. 16, 2006, "Shape Memory Polymers"); 20070135907 (Wilson et al., Jun. 14, 2007, "Stent with Expandable Foam"); 20070176333 (Greene et al., Aug. 2, 2007, "Vascular Embolization with an Expansible Implant"); and 20090112250 (Greene et al., Apr. 30, 2009, "Vascular Embolization with an Expansible Implant").

Prior art which appears to be within this category also includes U.S. patent applications: 20090318941 (Sepetka et al., Dec. 24, 2009, "Self-Expandable Endovascular Device for Aneurysm Occlusion"); 20110005062 (Greene et al., Jan. 13, 2011, "Vascular Embolization with an Expansible Implant"); 20110039967 (Wilson et al., Feb. 17, 2011, "Shape Memory Polymers"); 20110089592 (Farnsworth et al., Apr. 21, 2011, "Method of Making Porous Self-Cohered Web Materials"); 20110137405 (Wilson et al., Jun. 9, 2011, "Stent with Expandable Foam"); 20110144686 (Wilson et al., Jun. 16, 2011, "Shape Memory Polymer Foams for Endovascular Therapies"); 20130045182 (Gong et al., Feb. 21, 2013, "Polysaccharide Based Hydrogels"); 20130253086 (Wilson et al., Sep. 26, 2013, "Shape Memory Polymers"); 20130253634 (Wilson et al., Sep. 26, 2013, "Stent with Expandable Foam"); 20130289690 (Thapliyal, Oct. 31, 2013, "Personalized Prosthesis and Methods of Use"); and 20140018902 (Myr, Jan. 16, 2014, "Tailor-Made Stent Graft and Procedure for Minimally Invasive Aneurysm Repair with Novel Tailor-Made Balloon, Novel Guidewire, and Novel Capsulated Bioglue").

37. Extravascular Sleeve Around Aneurysm Sac and Parent Vessel:

The prior art also discloses devices and methods for treating aneurysms comprising an extravascular sleeve which is implanted around an aneurysm sac and the parent vessel of the aneurysm. Prior art which appears to be within this category includes U.S. Pat. No. 7,818,084 (Boyden et al., Oct. 19, 2010, "Methods and Systems for Making a Blood Vessel Sleeve"); U.S. Pat. No. 8,095,382 (Boyden et al., Jan. 10, 2012, "Methods and Systems for Specifying a Blood Vessel Sleeve"); U.S. Pat. No. 8,147,537 (Boyden et al., Apr. 3, 2012, "Rapid-Prototyped Custom-Fitted Blood Vessel Sleeve"); U.S. Pat. No. 8,163,003 (Boyden et al., Apr. 24, 2012, "Active Blood Vessel Sleeve Methods and Systems"); U.S. Pat. No. 8,478,437 (Boyden et al., Jul. 2, 2013, "Methods and Systems for Making a Blood Vessel Sleeve"); and U.S. Pat. No. 8,491,459 (Yun, Jul. 23, 2013, "Expandable Vessel Harness for Treating Vessel Aneurysms"); and U.S. patent application 20130218191 (Heltai, Aug. 22, 2013, "Method for Deploying a Sleeve and Tubing Device for Restricting and Constricting Aneurysms and a Sleeve and Tubing Device and System").

38. Other Devices for Aneurysm Treatment:

Finally, there are a variety of devices and methods for treating aneurysms which are relevant to this application, but which do not fit neatly into the above categories. I have included them in this miscellaneous category for completeness. Prior art which appears to be within this miscellaneous category includes U.S. Pat. No. 6,603,994 (Wallace et al., Aug. 5, 2003, "Apparatus and Method for Internally Inducing a Magnetic Field in an Aneurysm to Embolize Aneurysm with Magnetically-Controllable Substance"); U.S. Pat. No. 7,182,744 (Yamasaki et al., Feb. 27, 2007, "Method and Apparatus for Aneurismal Treatment"); U.S. Pat. No. 7,294,137 (Rivelli et al., Nov. 13, 2007, "Device for Multi-Modal Treatment of Vascular Lesions"); U.S. Pat. No. 7,744,610 (Hausen, Jun. 29, 2010, "System for Closing a Tissue Structure from Inside"); and U.S. Pat. No. 8,728,094 (Roorda et al., May 20, 2014, "Percutaneous Aneurysm Inversion and Ligation"). Prior art which appears to be within this category also includes U.S. patent applications: 20020087077 (Wallace et al., Jul. 4, 2002, "Apparatus and Method for Internally Inducing a Magnetic Field in an Aneurysm to Embolize Aneurysm with Magnetically-Controllable Substance"); 20090299448 (Timko et al., Dec. 3, 2009, "Aneurysm Treatment System"); 20120310611 (Sadasivan et al., Dec. 6, 2012, "System and Method for Simulating Deployment Configuration of an Expandable Device"); and 20130023903 (Roorda et al., Jan. 24, 2013, "Percutaneous Aneurysm Inversion and Ligation").

SUMMARY OF THIS INVENTION

This invention can be embodied in a device for occluding a cerebral aneurysm comprising a series of proximally-anddistally-connected coil loops. This invention can further comprise a stretchable mesh which spans the interiors of these loops. These loops (and the stretchable mesh) overlap to create a mass (such as a coil-and-mesh ball) within the aneurysm sac which occludes the aneurysm.

BRIEF INTRODUCTION TO THE FIGURES

FIGS. 1 through 6 show two examples of how this invention can be embodied in devices and methods for occluding an aneurysm, but they do not limit the full generalizability of the claims.

FIGS. 1 through 3 show three sequential views (during deployment) of an embolic coil which forms interconnected contiguous loops within an aneurysm sac.

FIGS. 4 through 6 show three sequential views (during deployment) of an example like the one in FIGS. 1 through 3, except that there is a stretchable mesh within the loops.

DETAILED DESCRIPTION OF THE FIGURES

Figure 4:
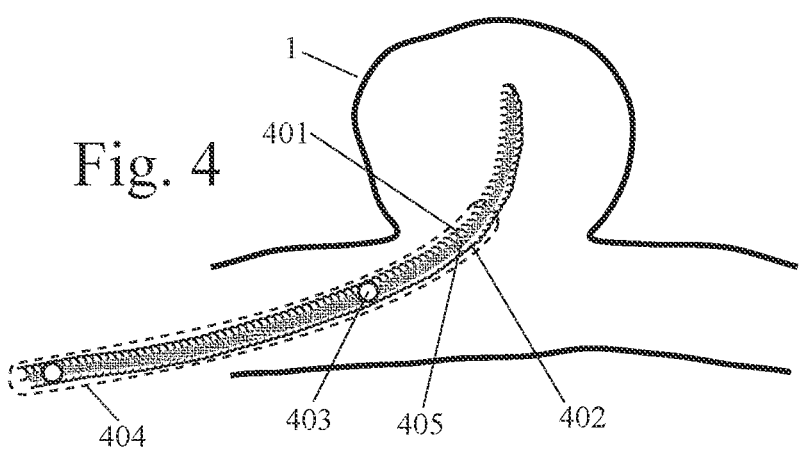

FIGS. 1 through 3 show an example of a device and method to occlude an aneurysm which can be described as an embolic coil for forming interconnected contiguous loops in an aneurysm. More specifically, FIGS. 1 through 3 show an example of a device to occlude an aneurysm comprising: (a) a first longitudinal section of a flexible longitudinal embolic member that is configured to be inserted into an aneurysm; (b) a second longitudinal section of a flexible longitudinal embolic member that is configured to be inserted into the aneurysm; (c) a plurality of connections between the first and second longitudinal sections, wherein these connections connect the first and second longitudinal sections at a plurality of selected locations along their longitudinal axes; and (d) a longitudinal lumen that is configured to be inserted into a blood vessel, wherein the first and second longitudinal sections travel through the lumen in order to be inserted into the aneurysm; wherein at least portions of the first and second longitudinal sections are configured in parallel within the lumen; wherein portions of the first and second longitudinal sections which are not connected by connections move apart from each other after exiting the lumen and the connections move closer to each other after exiting the lumen in order to form a plurality of loops within the aneurysm; wherein part of the perimeter of a loop is comprised of a portion of the first longitudinal section and part of the perimeter of a loop is comprised of a portion of the second longitudinal section; wherein a loop has a contiguous 360-degree perimeter with ends which are connected to each other; and wherein loops are interconnected at the connections.

FIGS. 1 through 3 also show an example of a device to occlude an aneurysm comprising: (a) a longitudinal lumen that is configured to be inserted into a blood vessel, wherein this blood vessel is the parent vessel from which an aneurysm has formed; (b) a first flexible longitudinal embolic member that is configured to travel through the longitudinal lumen and be inserted into the aneurysm sac; (c) a second flexible longitudinal embolic member that is configured to travel through the longitudinal lumen and be inserted into the aneurysm sac; wherein the longitudinal axes of the first and second flexible longitudinal embolic members are substantially parallel as these flexible longitudinal embolic members travel through the longitudinal lumen; and (d) a plurality of connections which connect the first and second flexible longitudinal embolic members at a plurality of locations along the lengths of the flexible longitudinal embolic members; wherein the segments of the first and second flexible longitudinal embolic members that are not connected by the connections move away from each other after they exit the longitudinal lumen, thereby forming loops within the aneurysm sac; wherein these loops are connected by the connections; and wherein accumulation of these loops within the aneurysm sac substantially occludes the aneurysm.

In an example, a longitudinal lumen can be a removable catheter. In an example, flexible longitudinal embolic members can be coils. In an example, connections can connect flexible longitudinal embolic members at uniformly-spaced locations along their lengths so as to form equal-size loops within the aneurysm sac and wherein these equal-size loops substantially span the circumference of the aneurysm sac. In an example, connections can connect flexible longitudinal embolic members at uniformly-spaced locations along their lengths so as to form equal-size loops within the aneurysm sac and these equal-size loops substantially span the circumference of the aneurysm sac without protruding into the parent vessel. In an example, connections can connect flexible longitudinal embolic members at non-uniformly-spaced locations along their lengths so as to form loops of different sizes within the aneurysm sac and these different size loops substantially occlude the interior as well as the circumference of the aneurysm sac.

We now discuss the specific components of FIGS. 1 through 3 in detail. FIGS. 1 through 3 show three sequential views of the same example of a device and method to occlude an aneurysm. To provide anatomical context, FIG. 1 shows a longitudinal cross-sectional view of an aneurysm sac 1 which has formed on a longitudinal blood vessel. FIG. 1 also shows an occlusive device comprising: a longitudinal lumen 104 that has been inserted into the longitudinal blood vessel; a first flexible longitudinal embolic member 101 that travels through lumen 104 into aneurysm sac 1; a second flexible longitudinal embolic member 102 that travels through lumen 104 into aneurysm sac 1; and a plurality of connections (including 103) which connect first and second embolic members 101 and 102 at a plurality of locations along their longitudinal lengths. In this example, flexible longitudinal embolic members 101 and 102 are two different segments (or sides) of the same continuous flexible longitudinal embolic member. In this example, this continuous member has two parallel segments or sides (comprising flexible longitudinal embolic members 101 and 102) within longitudinal lumen 104. In another example, embolic member 101 and embolic 102 can be different embolic members that are connected in some other manner at their distal ends.

In this example, flexible longitudinal embolic members 101 and 102 are substantially parallel as they travel through longitudinal lumen 104. However, as shown in FIG. 2, portions of embolic members 101 and 102 which are not connected to each other separate from each other after they exit longitudinal lumen 104 within aneurysm sac 1. In an example, this separation can be partly caused by pressure from contact with the wall of aneurysm sac 1. In an example, this separation can be partly caused by embolic members 101 and 102 having a shape memory with a shape that is restored after these embolic members exit longitudinal lumen 104. In the example that is shown in FIGS. 1 and 2, segments of embolic members 101 and 102 which are not connected by connections (such as 103) move away from each other after they exit longitudinal lumen 104.

FIG. 3 shows the accumulation of a plurality of interconnected, contiguous loops within aneurysm sac 1 as flexible longitudinal embolic members 101 and 102 continue to be pushed into aneurysm sac 1. These loops are pair-wise connected to each other by the plurality of connections (including connection 103). As shown in FIG. 3, accumulation of this plurality of loops within aneurysm sac 1 forms an embolic mass which substantially occludes the aneurysm. In this example, the interconnected and contiguous nature of these loops helps to prevent loops from prolapsing out of aneurysm sac 1 into the parent blood vessel. This can result in less prolapse of coils into the parent vessel than is the case with coils in the prior art which disperse and accumulate in a free-form spiraling manner within the aneurysm sac. Also, FIG. 3 shows longitudinal lumen 104 as having been removed.

In the example shown in FIGS. 1 through 3, the connections (such as 103) between embolic members 101 and 102 are relatively evenly-spaced along the longitudinal lengths of embolic members 101 and 102. In an example, the spacing of these connections can be selected for a specific aneurysm with a specific size and shape in order to most efficiently occlude that specific aneurysm. In an example, the spacing of connections can differ between devices which are configured to occlude narrow-neck aneurysms and devices which are configured to occlude wide-neck aneurysms. In an example, the spacing of these connections can be pre-selected to vary along the length of embolic members 101 and 102 in order to most efficiently occlude an aneurysm at different times or stages during the occlusion procedure. For example, connections can be separated by longer distances at the most distal portions of embolic members 101 and 102 and become progressively shorter at more proximal portions of embolic members 101 and 102. In an example, the most distal connections can be spaced to form loops which span the entire circumference of the aneurysm sac but successive loops can become smaller and smaller to better fill the central space of the aneurysm sac.

Figure 5:
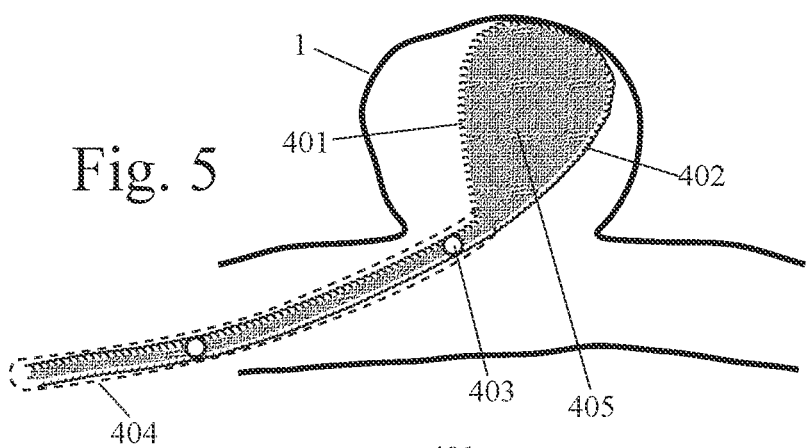
Figure 6:
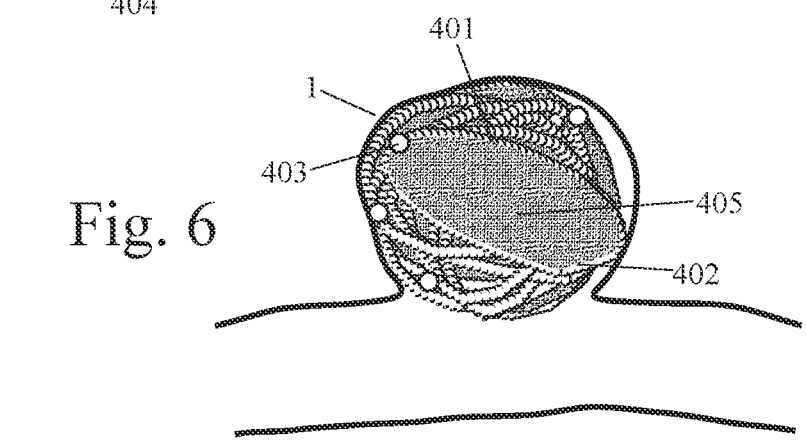

FIGS. 4 through 6 show another example of a device and method to occlude an aneurysm which is like the example shown in FIGS. 1 through 3, except that there is also a stretchable mesh within the loops. FIGS. 4 through 6 show three sequential views of a device and method to occlude an aneurysm which can be described as embolic coils which form interconnected contiguous loops within an aneurysm sac, wherein the interiors of these loops are spanned by a stretchable mesh.

More specifically, FIGS. 4 through 6 show an example of a device to occlude an aneurysm comprising: (a) a first longitudinal section of a flexible longitudinal embolic member that is configured to be inserted into an aneurysm; (b) a second longitudinal section of a flexible longitudinal embolic member that is configured to be inserted into the aneurysm; (c) a stretchable mesh which spans between the first and second longitudinal sections; (d) a plurality of connections between the first and second longitudinal sections, wherein these connections connect the first and second longitudinal sections at a plurality of selected locations along their longitudinal axes; and (e) a longitudinal lumen that is configured to be inserted into a blood vessel; wherein the first and second longitudinal sections travel through the lumen in order to be inserted into the aneurysm; wherein at least portions of the first and second longitudinal sections are configured in parallel within the lumen; wherein portions of the first and second longitudinal sections which are not connected by connections move apart from each other after exiting the lumen and connections move closer to each other after exiting the lumen in order to form a plurality of loops within the aneurysm; wherein part of the perimeter of a loop is comprised of a portion of the first longitudinal section and part of the perimeter of a loop is comprised of a portion of the second longitudinal section; wherein a loop has a contiguous 360-degree perimeter with ends which are connected to each other; and wherein loops are interconnected at the connections.

FIGS. 4 through 6 also show an example of a device to occlude an aneurysm comprising: (a) a flexible longitudinal lumen that is configured to be inserted into a blood vessel, wherein this blood vessel is the parent vessel from which an aneurysm has formed; (b) a first flexible longitudinal embolic member that is configured to travel through the flexible longitudinal lumen and be inserted into the aneurysm sac; (c) a second flexible longitudinal embolic member that is configured to travel through the flexible longitudinal lumen and be inserted into the aneurysm sac; wherein the flexible longitudinal axes of the first and second longitudinal embolic members are substantially parallel as these longitudinal embolic members travel through the flexible longitudinal lumen; (d) a stretchable mesh which spans between the first and second flexible longitudinal sections; and (e) a plurality of connections which connect the first and second longitudinal embolic members at a plurality of locations along the lengths of the longitudinal embolic members; wherein the segments of the first and second longitudinal embolic members that are not connected by the connections move away from each other after they exit the flexible longitudinal lumen, thereby forming loops within the aneurysm sac; wherein these loops are connected by the connections; and wherein accumulation of these loops and the stretchable mesh within the aneurysm sac substantially occludes the aneurysm.

In an example, a longitudinal lumen can be a removable catheter. In an example, flexible longitudinal embolic members can be coils. In an example, connections can connect flexible longitudinal embolic members at uniformly-spaced locations along their lengths so as to form equal-size loops within the aneurysm sac and wherein these equal-size loops substantially span the circumference of the aneurysm sac. In an example, connections can connect flexible longitudinal embolic members at uniformly-spaced locations along their lengths so as to form equal-size loops within the aneurysm sac and these equal-size loops substantially span the circumference of the aneurysm sac without protruding into the parent vessel. In an example, connections can connect flexible longitudinal embolic members at non-uniformly-spaced locations along their lengths so as to form loops of different sizes within the aneurysm sac and these different size loops substantially occlude the interior as well as the circumference of the aneurysm sac. In an example, the embolic members can criss-cross each other at their connections, wherein the embolic members switch sides from one loop to the next. In an example, sinusoidal embolic members can criss-cross each other at their connections, wherein the embolic members switch sides from one loop to the next.

In an example, a stretchable mesh can be an elastic mesh. In an example, a stretchable mesh can be made from a polymer. In an example, a stretchable mesh can be made from metal. In an example, a stretchable mesh can be attached to the first and second flexible longitudinal embolic members. In an example, a stretchable mesh can loop around the first and second flexible longitudinal embolic members. In an example, a stretchable mesh can span the entire interiors of loops. In an example, a stretchable mesh can span at least 50% of the interiors of loops. In an example, a stretchable mesh can be impermeable to blood flow. In an example, a stretchable mesh can resist blood flow.

We now discuss the specific components of FIGS. 4 through 6 in detail. FIGS. 4 through 6 show three sequential views of the same example of a device and method to occlude an aneurysm. To provide anatomical context, FIG. 4 shows a longitudinal cross-sectional view of an aneurysm sac 1 which has formed on a longitudinal blood vessel. FIG. 4 also shows an occlusive device comprising: a longitudinal lumen 404 that has been inserted into the longitudinal blood vessel; a first flexible longitudinal embolic member 401 that travels through lumen 404 into aneurysm sac 1; a second flexible longitudinal embolic member 402 that travels through lumen 404 into aneurysm sac 1; a stretchable mesh 405 which spans between first flexible longitudinal embolic member 401 and second flexible longitudinal embolic member 402; and a plurality of connections (including 403) which connect first and second flexible longitudinal embolic members 401 and 402 at a plurality of locations along their longitudinal lengths. In this example, flexible longitudinal embolic members 401 and 402 are two different segments (or sides) of the same continuous embolic member. In this example, this continuous embolic member has two parallel segments or sides (comprising flexible longitudinal embolic members 401 and 402) within longitudinal lumen 404. In another example, flexible longitudinal embolic member 401 and flexible longitudinal embolic member 402 can be different flexible longitudinal embolic members that are connected in some other manner at their distal ends.

In this example, flexible longitudinal embolic members 401 and 402 are substantially parallel as they travel through longitudinal lumen 404. However, as shown in FIG. 5, portions of flexible longitudinal embolic members 401 and 402 which are not connected to each other separate from each other after they exit longitudinal lumen 404 within aneurysm sac 1. In an example, this separation can be partly caused by pressure from contact with the wall of aneurysm sac 1. In an example, this separation can be partly caused by flexible longitudinal embolic members 401 and 402 having a shape memory with a shape that is restored after these embolic members exit longitudinal lumen 404. In the example that is shown in FIGS. 1 and 2, segments of flexible longitudinal embolic members 401 and 402 which are not connected by connections (such as 403) move away from each other after they exit longitudinal lumen 404.

FIG. 6 shows the accumulation of a plurality of interconnected, contiguous loops within aneurysm sac 1 as flexible longitudinal embolic members 401 and 402 continue to be pushed into aneurysm sac 1. These loops are pair-wise connected to each other by the plurality of connections (including connection 403). As shown in FIG. 6, the stretchable mesh stretches to span the arcuate interiors of these loops. As shown in FIG. 6, accumulation of this plurality of loops and the stretchable mesh within aneurysm sac 1 forms an embolic coil-and-mesh mass (such as a coil-and-mesh ball) which substantially occludes the aneurysm. In this example, the interconnected and contiguous nature of these loops helps to prevent loops from prolapsing out of aneurysm sac 1 into the parent blood vessel. This can result in less prolapse of coils into the parent vessel than is the case with coils in the prior art which disperse and accumulate in a free-form spiraling manner within the aneurysm sac. Also, FIG. 6 shows longitudinal lumen 404 as having been removed.

In the example shown in FIGS. 4 through 6, the connections (such as 403) between embolic members 401 and 402 are relatively evenly-spaced along the longitudinal lengths of embolic members 401 and 402. In an example, the spacing of these connections can be selected for a specific aneurysm with a specific size and shape in order to most efficiently occlude that specific aneurysm. In an example, the spacing of connections can differ between devices which are configured to occlude narrow-neck aneurysms and devices which are configured to occlude wide-neck aneurysms. In an example, the spacing of these connections can be pre-selected to vary along the length of embolic members 401 and 402 in order to most efficiently occlude an aneurysm at different times or stages during the occlusion procedure. For example, connections can be separated by longer distances at the most distal portions of embolic members 401 and 402 and become progressively shorter at more proximal portions of embolic members 401 and 402. In an example, the most distal connections can be spaced to form loops which span the entire circumference of the aneurysm sac but successive loops can become smaller and smaller to better fill the central space of the aneurysm sac. In an example, connections which connect flexible longitudinal embolic members can be at non-uniform distances along their lengths in order to better occlude an aneurysm sac.

In an example, the device shown in FIGS. 4 through 6 can be described as a device to occlude an aneurysm comprising a series of proximally-and-distally-connected mesh-filled loops. In an example, the device shown in FIGS. 4 through 6 can be described as a device to occlude an aneurysm comprising a series of proximally-and-distally-connected mesh-filled loops which overlap within an aneurysm sac to create a coil-and-mesh mass (such as a coil-and-mesh ball). In an example, the device shown in FIGS. 4 through 6 can be described as a device to occlude an aneurysm comprising a series of proximally-and-distally-connected mesh-filled loops whose sides are relatively parallel as they travel through a lumen and whose sides become concave after they exit the lumen into an aneurysm sac in order to create a coil-and-mesh mass (such as a coil-and-mesh ball).

In an example, FIGS. 4 through 6 show a device for occluding an aneurysm comprising: a catheter; a first segment of a longitudinal embolic coil; a second segment of a longitudinal embolic coil, wherein the first and second segments are connected to each other at a proximal location along their length and are connected to each other at a distal location along their length, wherein the first and second segments have a first configuration when they are within the catheter, wherein there is a first average distance between the first and second segments when they are in the first configuration, wherein the first and second segments have a second configuration after they exit the catheter into an aneurysm sac, wherein there is a second average distance between the first and second segments when they are in the second configuration, and wherein the second distance is greater than the first distance; and a stretchable mesh which spans between the first and second segments.

In an example, FIGS. 4 through 6 show a device for occluding an aneurysm comprising: a catheter; a first longitudinal embolic coil; a second longitudinal embolic coil, wherein the first and second longitudinal embolic coils are connected to each other at a plurality of locations along their lengths, forming a plurality of loops whose sides comprise segments of the first longitudinal embolic coil and segments of the second longitudinal embolic coil, wherein the first and second longitudinal embolic coils have a first configuration when they are within the catheter and a second configuration after they exit the catheter into an aneurysm sac, wherein the sides of the loops are further apart in the second configuration than in the first configuration; and a stretchable mesh which spans the interiors of the loops between the first and second longitudinal embolic coils.

In an example, this invention can be embodied in a device to occlude an aneurysm comprising: a longitudinal lumen that is configured to be inserted into a blood vessel, wherein this blood vessel is the parent vessel from which an aneurysm has formed; a first flexible longitudinal embolic member that is configured to travel through the longitudinal lumen and be inserted into the aneurysm sac; a second flexible longitudinal embolic member that is configured to travel through the longitudinal lumen and be inserted into the aneurysm sac; wherein the longitudinal axes of the first and second flexible longitudinal embolic members are substantially parallel as these embolic members travel through the longitudinal lumen; and a plurality of connections which connect the first and second embolic members at a plurality of locations along their lengths; wherein segments of the first and second flexible longitudinal embolic members that are not connected by the connections move away from each other after they exit the longitudinal lumen, thereby forming loops within the aneurysm sac; wherein these loops are connected by the connections; and wherein accumulation of these loops within the aneurysm sac substantially occludes the aneurysm.

In an example, a longitudinal lumen can be a catheter. In an example, flexible longitudinal embolic members can be coils. In an example, connections can connect flexible longitudinal embolic members at uniformly-spaced locations along their lengths. In an example, connections which connect flexible longitudinal embolic members can be at non-uniform distances along their lengths in order to better occlude an aneurysm sac.

In an example, this invention can be embodied in a device to occlude an aneurysm comprising: a longitudinal lumen that is configured to be inserted into a blood vessel, wherein this blood vessel is the parent vessel from which an aneurysm has formed; a first flexible longitudinal embolic member that is configured to travel through the longitudinal lumen and be inserted into the aneurysm sac; a second flexible longitudinal embolic member that is configured to travel through the longitudinal lumen and be inserted into the aneurysm sac; wherein the longitudinal axes of the first and second embolic members are substantially parallel as these embolic members travel through the longitudinal lumen; a stretchable mesh which spans between the first flexible longitudinal embolic member and the second flexible longitudinal embolic member; and a plurality of connections which connect the first and second embolic members at a plurality of locations along the lengths of the embolic members; wherein the segments of the first and second embolic members that are not connected by the connections move away from each other after they exit the longitudinal lumen, thereby forming loops within the aneurysm sac; wherein these loops are connected by the connections; and wherein accumulation of these loops within the aneurysm sac substantially occludes the aneurysm.

In an example, a longitudinal lumen can be a catheter. In an example, flexible longitudinal embolic members can be coils. In an example, connections can connect flexible longitudinal embolic members at uniformly-spaced locations along their lengths. In an example, a stretchable mesh can be an elastic mesh. In an example, a stretchable mesh can be impermeable to blood flow. In an example, a stretchable mesh can resist blood flow. In an example, a stretchable mesh can fill the entire interior of a loop. In an example, a stretchable mesh can fill at least 50% of the interior of a loop.

In an example, this invention can be embodied in a device for occluding a cerebral aneurysm comprising: a longitudinal lumen that is configured to be inserted into a blood vessel; a first segment of a longitudinal embolic coil; a second segment of a longitudinal embolic coil, wherein the first and second segments are connected to each other at a proximal location along their length and are connected to each other at a distal location along their length, wherein the first and second segments have a first configuration when they are within the longitudinal lumen, wherein there is a first average distance between the first and second segments when they are in the first configuration, wherein the first and second segments have a second configuration after they exit the longitudinal lumen into an aneurysm sac, wherein there is a second average distance between the first and second segments when they are in the second configuration, and wherein the second distance is greater than the first distance; and a stretchable mesh which spans between the first and second segments.

In an example, the first and second segments can form a loop. In an example, this loop can be more circular in the second configuration than in the first configuration. In an example, this loop can have a greater interior area in the second configuration than in the first configuration. In an example, the stretchable mesh can fill the entire interior of a loop. In an example, the stretchable mesh can fill at least 50% of the interior of a loop. In an example, the stretchable mesh can resist blood flow.

I claim:

1. A device to occlude an aneurysm comprising:
    a longitudinal lumen that is configured to be inserted into a blood vessel, wherein this blood vessel is the parent vessel from which an aneurysm has formed;
    a first flexible longitudinal embolic member that is configured to travel through the longitudinal lumen and be inserted into the aneurysm sac;
    a second flexible longitudinal embolic member that is configured to travel through the longitudinal lumen and be inserted into the aneurysm sac; wherein the longitudinal axes of the first and second embolic members are substantially parallel as these embolic members travel through the longitudinal lumen;
    a stretchable mesh which spans between the first flexible longitudinal embolic member and the second flexible longitudinal embolic member; and
    a plurality of connections which connect the first and second embolic members at a plurality of locations along the lengths of the embolic members; wherein segments of the first and second embolic members that are not connected by the connections move away from each other after they exit the longitudinal lumen, thereby forming loops within the aneurysm sac; wherein part of the perimeter of a loop is comprised of a segment of the first flexible longitudinal embolic member and part of the perimeter of a loop is comprised of a segment of the second flexible longitudinal embolic member; wherein a loop has a contiguous 360-degree perimeter; wherein the stretchable mesh fills at least 50% of the interior of the loop; wherein these loops are connected by the connections; wherein accumulation of these loops within the aneurysm sac substantially occludes the aneurysm; and wherein the most distal connections are spaced to form loops which are configured to span the circumference of the aneurysm sac but successive contiguous loops become smaller to fill the central space of the aneurysm sac.

2. The device in claim 1 wherein the longitudinal lumen is a catheter.

3. The device in claim 1 wherein the flexible longitudinal embolic members are coils.

4. The device in claim 1 wherein the stretchable mesh is an elastic mesh.

5. The device in claim 1 wherein the stretchable mesh is impermeable to blood flow.

6. The device in claim 1 wherein the stretchable mesh resists blood flow.

7. The device in claim 1 wherein the stretchable mesh fills the entire interior of a loop.

* * * * *